United States Patent
Kleemann et al.

(10) Patent No.: US 7,078,428 B2
(45) Date of Patent: Jul. 18, 2006

(54) ISOINDOLONE DERIVATIVES, PREPARATION PROCESS AND INTERMEDIATES OF THIS PROCESS, THEIR USE AS MEDICAMENTS, AND PHARMACEUTICAL COMPOSITIONS COMPRISING THEM

(75) Inventors: Heinz-Werner Kleemann, Bischofsheim (DE); Armin Hofmeister, Nierstein (DE); Jean-Christophe Carry, Saint Maur des Fosses (FR); Baptiste Ronan, Clamart (FR); Serge Mignani, Chatenay-Malabry (FR); Antony Bigot, Massy (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 55 days.

(21) Appl. No.: 10/445,618

(22) Filed: May 27, 2003

(65) Prior Publication Data
US 2004/0048916 A1 Mar. 11, 2004

Related U.S. Application Data
(60) Provisional application No. 60/396,001, filed on Jul. 16, 2002.

(30) Foreign Application Priority Data
Jun. 3, 2002 (FR) .............................. 02 06783

(51) Int. Cl.
*A61K 31/4035* (2006.01)
*C07D 209/44* (2006.01)

(52) U.S. Cl. ................... 514/416; 548/469; 548/472
(58) Field of Classification Search ............... 548/472, 548/469; 514/416, 445
See application file for complete search history.

(56) References Cited
U.S. PATENT DOCUMENTS

| 5,866,610 | A | 2/1999 | Lang |
| 6,114,393 | A | 9/2000 | Lang |
| 6,348,476 | B1 | 2/2002 | Scholz |
| 6,399,824 | B1 | 6/2002 | Hofmeister |
| 6,420,430 | B1 | 7/2002 | Linz |
| 6,462,024 | B1 | 10/2002 | Lang |
| 6,492,401 | B1 | 12/2002 | Mamanaka et al. |

FOREIGN PATENT DOCUMENTS
WO  WO 01/77075  10/2001
WO  WO 02/081443  10/2002

OTHER PUBLICATIONS

Cavalleri, et al., Synthesis of 5–Trifluoromethyl–1,4–dihydrazinophthalazine, Notes; Jan. 1970; 13; pp. 148–149.
Hinde, et al., Kinetics and mechanism of the formation of mono– and di–phthalate esters catalayeed by titanium and tin alkoxides, J. Chem. Soc. Perkin Trans. 2, 1998; pp. 1249–1256.
Jeong. et al., Novel Hetrerocylic Ring–Expansion and/or Dehydration Reactions of Propargylio and Allenylic Hydroxy gamma–lactama in the Presence of Strong Base of Lewis Acid, Tetrahedron; 54; 1998; pp. 14437–14454.
Shah, et al.+, Synthesis and Enantiomario Separation of 2–Phthalimidino–glutaric Acid Analogoues: Potent Inhibitors of Tumor Metastasis, J. Med. Chem.; 1999; 42; pp. 3014–3017.
Kawamoto et al, Potent and Selective Inhibition of hte Human Na+/H+ exchanger isoform NHE1 by a Novel Aminoguanidine Derivative T–162559, European Journal of Pharmacology, Amsterdam, NL; vol. 420; No. 1, (2001): pp. 1–8.
Konig W. et al., Perchioric Acid in Peptide Chemistry, Peptides, (1990), Proc. European Peptide Symp., 21st (1991), pp. 143–145.
March J., Aliphatic Nucleophilic Substitution, Advanced Organic Chemistry. 3rd Edition, John Wiley & Sons, 1985, p. 350.
Staab H.A., Syntheses Using Heterocyclic Amides (Azolides) [★], Chem. Int. Ed. Engl. 1, pp. 351–367.
U.S. Appl. No. 09/836,035, filed Apr. 17, 2001, Chen et al.

*Primary Examiner*—Golam M. M. Shameem
(74) *Attorney, Agent, or Firm*—Joseph D. Rossi

(57) ABSTRACT

The present invention relates to the novel isoindolone derivatives of the formula I

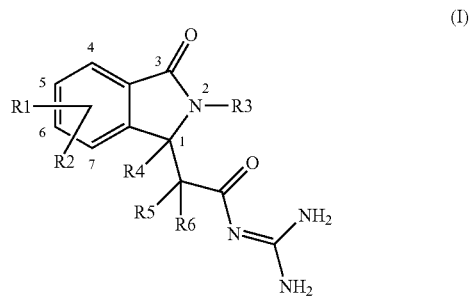

in which R1 to R6 have the meanings stated in the claims. The inventive compounds are suitable as antiarrhythmic medicaments with a cardioprotective component for infarction prophylaxis and infarction treatment and for the treatment of angina pectoris. They also inhibit in a preventive manner the pathophysiological processes associated with the development of ischemia-induced damage, in particular in the triggering of ischemia-induced cardiac arrhythmias and of heart failure.

18 Claims, No Drawings

ISOINDOLONE DERIVATIVES, PREPARATION PROCESS AND INTERMEDIATES OF THIS PROCESS, THEIR USE AS MEDICAMENTS, AND PHARMACEUTICAL COMPOSITIONS COMPRISING THEM

This application claims the benefit of U.S. Provisional Application No. 60/396,001, filed Jul. 16, 2002, and incorporated herein by reference.

The present invention relates to the novel isoindolone compounds of the formula I.

$$\text{(I)}$$

The inventive compounds are suitable as antiarrhythmic medicaments with a cardioprotective component for infarction prophylaxis and infarction treatment and for the treatment of angina pectoris. They also inhibit in a preventive manner the pathophysiological processes associated with the development of ischemia-induced damage, in particular in the triggering of ischemia-induced cardiac arrhythmias and of heart failure.

The invention relates to compounds of the formula I, in which

R1 and R2
are, independently of one another, hydrogen, alkyl having 1, 2, 3 or 4 carbon atoms, alkenyl having 2, 3, 4, 5 or 6 carbon atoms, alkynyl having 2, 3, 4, 5 or 6 carbon atoms, aryl, heteroaryl, F, Cl, Br, I, $NO_2$, $NH_2$, alkylamino having 1, 2, 3 or 4 carbon atoms, NRaRb, alkylcarbonylamino having 1, 2, 3 or 4 carbon atoms, OH, alkoxy having 1, 2, 3 or 4 carbon atoms, $S(O)_nR^7$, $CO_2H$, alkoxycarbonyl having 1, 2, 3 or 4 carbon atoms, alkylcarbonyl having 1, 2, 3 or 4 carbon atoms, $CONH_2$, CONRaRb, CN, polyfluoroalkyl having 1, 2, 3 or 4 carbon atoms, polyfluoroalkoxy having 1, 2 or 3 carbon atoms or $SO_3H$;
R1 and R2 themselves optionally being substituted by a linear or branched alkyl group having 1, 2, 3 or 4 carbon atoms;
n zero, 1 or 2

R3 is hydrogen, aryl, heteroaryl, a group of the Alk-R8 type or cycloalkyl having 3, 4, 5, 6, 7 or 8 carbon atoms,
in which cycloalkyl is optionally substituted by one or more substituents selected from the group F, Cl, Br or I,
Alk is alkyl having of 1, 2, 3, 4 or 5 carbon atoms in a linear or branched chain,
R8 is hydrogen, cycloalkyl having 3, 4, 5, 6, 7 or 8 carbon atoms, polyfluoroalkyl having 1, 2, 3 or 4 carbon atoms, aryl, heteroaryl, OH, alkoxy having 1, 2, 3 or 4 carbon atoms, $CO_2H$, $CONH_2$, CONRaRb, $NH_2$, alkylamino having 1, 2, 3 or 4 carbon atoms or NRaRb;

R4, R5 and R6
are, independently of one another, hydrogen or a linear or branched alkyl having 1, 2, 3 or 4 carbon atoms;
R7 is a linear or branched alkyl having 1, 2, 3 or 4 carbon atoms;
Ra and Rb
are, independently of one another, is a linear or branched alkyl having 1, 2, 3 or 4 carbon atoms or alternatively Ra and Rb form, together with the nitrogen atom to which they are attached, a 5- or 6-membered heterocycle optionally containing another hetero atom chosen from O, S or N;
and racemic mixtures, enantiomers and diastereomers thereof and mixtures thereof, tautomers thereof and pharmaceutically acceptable salts thereof.

Preference is given to compounds of the formula I, in which the meanings are:

R1 and R2
are, independently of one another, hydrogen, alkyl having 1, 2, 3 or 4 carbon atoms, F, Cl, Br, I, $NH_2$, alkylamino having 1, 2, 3 or 4 carbon atoms, NRaRb, alkylcarbonylamino having 1, 2, 3 or 4 carbon atoms, OH, alkoxy having 1, 2, 3 or 4 carbon atoms, $CO_2H$, alkoxycarbonyl having 1, 2, 3 or 4 carbon atoms, polyfluoroalkyl having 1, 2, 3 or 4 carbon atoms, polyfluoroalkoxy having 1, 2 or 3 carbon atoms or $SO_3H$,
R1 and R2 themselves optionally being substituted by a linear or branched alkyl group having 1, 2, 3 or 4 carbon atoms;

R3 is a group of the Alk-R8 type or cycloalkyl having 3, 4, 5, 6, 7 or 8 carbon atoms,
in which cycloalkyl is optionally substituted by one or more substituents selected from the group F, Cl or Br,
Alk is an alkyl having 1, 2, 3, 4 or 5 carbon atoms in a linear or branched chain,
R8 is hydrogen, cycloalkyl having 3, 4, 5, 6, 7 or 8 carbon atoms, polyfluoroalkyl having 1, 2, 3 or 4 carbon atoms, aryl or heteroaryl;

R4, R5 and R6
are, independently of one another, hydrogen or a linear or branched alkyl having 1, 2, 3 or 4 carbon atoms;
Ra and Rb
are, independently of one another, a linear or branched alkyl having 1, 2, 3 or 4 carbon atoms, or Ra and Rb form, together with the nitrogen atom to which they are attached, a 5- or 6-membered heterocycle optionally containing another hetero atom chosen from O, S and N;
and racemic mixtures, enantiomers and diastereomers thereof and mixtures thereof, tautomers thereof and pharmaceutically acceptable salts thereof.

Particular preference is given to compounds of the formula I, in which the meanings are:

R1 and R2
are, independently of one another, hydrogen, alkyl having 1, 2, 3 or 4 carbon atoms, F, Cl, Br, I, OH, alkoxy having 1, 2, 3 or 4 carbon atoms, polyfluoroalkyl having 1, 2, 3 or 4 carbon atoms or polyfluoroalkoxy having 1, 2 or 3 carbon atoms,
R1 and R2 themselves optionally being substituted by a linear or branched alkyl having 1, 2, 3 or 4 carbon atoms;

R3 is a group of the Alk-R8 type or cycloalkyl having 3, 4, 5, 6, 7 or 8 carbon atoms, in which cycloalkyl is optionally substituted by one or more substituents selected from the group F or Cl, Alk is an alkyl having 1, 2, 3,4 or 5 carbon atoms in a linear or branched chain, R8 is hydrogen, cycloalkyl having 3, 4, 5, 6, 7 or 8 carbon atoms or polyfluoroalkyl having 1, 2, 3 or 4 carbon atoms;

R4, R5 and R6 are, independently of one another, hydrogen or a linear or branched alkyl having 1, 2, 3 or 4 carbon atoms; and racemic mixtures, enantiomers and diastereomers thereof and mixtures thereof, tautomers thereof and pharmaceutically acceptable salts thereof.

In one embodiment compounds of the formula I are defined as above and R3 represents a hydrogen atom, an aryl or heteroaryl group or a chain of the Alk-R8 type, where Alk represents a chain of 1 to 5 carbon atoms in a linear or branched chain and R8 represents a hydrogen atom, a cycloalkyl group (C3–C8), polyfluoroalkyl group (C1–C4), aryl group, heteroaryl group, hydroxyl group, alkoxy group (C1–C4), carboxyl group, carboxamide group, amino group, alkylamino group (C1–C4) or group NRaRb, In one embodiment compounds of the formula I are defined as above and R4 represents a hydrogen atom. In another embodiment R5 represents a hydrogen atom.

Specific preference is given to compounds of the formula I, characterized in that it is chosen from the group of:
N-[2-(2-isobutyl-3-oxo-2,3-dihydro-1H-isoindol-1-yl)-2-methylpropionyl]guanidine,
N-[2-(2-cyclopropylmethyl-3-oxo-2,3-dihydro-1H-isoindol-1-yl)-2-methylpropionyl]guanidine,
N-[(3-oxo-2-(3,3,3-trifluoropropyl)-2,3-dihydro-1H-isoindol-1-yl)acetyl]guanidine,
N-[(3-oxo-2-(4,4,4-trifluorobutyl)-2,3-dihydro-1H-isoindol-1-yl)acetyl]guanidine,
N-[(3-oxo-2,3-dihydro-1H-isoindol-1-yl)acetyl]guanidine,
N-[(2-isobutyl-7-methyl-3-oxo-2,3-dihydro-1H-isoindol-1-yl)acetyl]guanidine,
N-[(4-amino-2-isobutyl-3-oxo-2,3-dihydro-1H-isoindol-1-yl)acetyl]guanidine,
N-[(5-amino-2-isobutyl-3-oxo-2,3-dihydro-1H-isoindol-1-yl)acetyl]guanidine,
N-[(6-amino-2-isobutyl-3-oxo-2,3-dihydro-1H-isoindol-1-yl)acetyl]guanidine,
N-[(7-amino-2-isobutyl-3-oxo-2,3-dihydro-1H-isoindol-1-yl)acetyl]guanidine,
N-[(4-hydroxy-2-isobutyl-3-oxo-2,3-dihydro-1H-isoindol-1-yl)acetyl]guanidine,
N-[(5-hydroxy-2-isobutyl-3-oxo-2,3-dihydro-1H-isoindol-1-yl)acetyl]guanidine,
N-[(6-hydroxy-2-isobutyl-3-oxo-2,3-dihydro-1H-isoindol-1-yl)acetyl]guanidine,
N-[(7-hydroxy-2-isobutyl-3-oxo-2,3-dihydro-1H-isoindol-1-yl)acetyl]guanidine,
N-[(4,7-dichloro-2-isobutyl-3-oxo-2,3-dihydro-1H-isoindol-1-yl)acetyl]guanidine,
N-[(4-fluoro-2-isobutyl-3-oxo-2,3-dihydro-1H-isoindol-1-yl)acetyl]guanidine,
N-[(5-fluoro-2-isobutyl-3-oxo-2,3-dihydro-1H-isoindol-1-yl)acetyl]guanidine,
N-[(6-fluoro-2-isobutyl-3-oxo-2,3-dihydro-1H-isoindol-1-yl)acetyl]guanidine,
N-[(4,5-difluoro-2-isobutyl-3-oxo-2,3-dihydro-1H-isoindol-1-yl)acetyl]guanidine,
N-[(6,7-difluoro-2-isobutyl-3-oxo-2,3-dihydro-1H-isoindol-1-yl)acetyl]guanidine,
N-[(4-carboxy-2-isobutyl-3-oxo-2,3-dihydro-1H-isoindol-1-yl)acetyl]guanidine,
N-[(5-carboxy-2-isobutyl-3-oxo-2,3-dihydro-1H-isoindol-1-yl)acetyl]guanidine,
N-[(6-carboxy-2-isobutyl-3-oxo-2,3-dihydro-1H-isoindol-1-yl)acetyl]guanidine,
N-[(7-carboxy-2-isobutyl-3-oxo-2,3-dihydro-1H-isoindol-1-yl)acetyl]guanidine,
N-[(2-isobutyl-1-methyl-3-oxo-2,3-dihydro-1H-isoindol-1-yl)acetyl]guanidine
and racemic mixtures, enantiomers and diastereomers thereof, and mixtures thereof, tautomers thereof and pharmaceutically acceptable salts thereof.

Another preference is given to compounds of the formula I, characterized in that it is chosen from the group of:
N-[(2-methyl-3-oxo-2,3-dihydro-1H-isoindol-1-yl)acetyl]guanidine,
N-[(2-ethyl-3-oxo-2,3-dihydro-1H-isoindol-1-yl)acetyl]guanidine,
N-[(3-oxo-2-propyl-2,3-dihydro-1H-isoindol-1-yl)acetyl]guanidine,
N-[2-(3-oxo-2-propyl-2,3-dihydro-1H-isoindol-1-yl)propionyl]guanidine,
N-[(2-isopropyl-3-oxo-2,3-dihydro-1H-isoindol-1-yl)acetyl]guanidine,
N-[2-(2-butyl-3-oxo-2,3-dihydro-1H-isoindol-1-yl)propionyl]guanidine,
N-[(2-isobutyl-3-oxo-2,3-dihydro-1H-isoindol-1-yl)acetyl]guanidine,
N-[2-(2-isobutyl-3-oxo-2,3-dihydro-1H-isoindol-1-yl)propionyl]guanidine,
N-[(2-cyclopropylmethyl-3-oxo-2,3-dihydro-1H-isoindol-1-yl)acetyl]guanidine,
N-[(2-benzyl-3-oxo-2,3-dihydro-1H-isoindol-1-yl)acetyl]guanidine,
N-[(3-oxo-2-(2,2,2-trifluoroethyl)-2,3-dihydro-1H-isoindol-1-yl)acetyl]guanidine,
N-[(2-isobutyl-4-methyl-3-oxo-2,3-dihydro-1H-isoindol-1-yl)acetyl]guanidine,
N-[(2-isobutyl-5-methyl-3-oxo-2,3-dihydro-1H-isoindol-1-yl)acetyl]guanidine,
N-[(2-isobutyl-6-methyl-3-oxo-2,3-dihydro-1H-isoindol-1-yl)acetyl]guanidine,
N-[(5-tert-butyl-2-isobutyl-3-oxo-2,3-dihydro-1H-isoindol-1-yl)acetyl]guanidine,
N-[(6-tert-butyl-2-isobutyl-3-oxo-2,3-dihydro-1H-isoindol-1-yl)acetyl]guanidine,
N-[(2-isobutyl-5-isopropoxy-3-oxo-2,3-dihydro-1H-isoindol-1-yl)acetyl]guanidine,
N-[(5-chloro-2-isobutyl-3-oxo-2,3-dihydro-1H-isoindol-1-yl)acetyl]guanidine,
N-[(6-chloro-2-isobutyl-3-oxo-2,3-dihydro-1H-isoindol-1-yl)acetyl]guanidine,
N-[(5-chloro-2-cyclopropylmethyl-3-oxo-2,3-dihydro-1H-isoindol-1-yl)acetyl]guanidine,
N-[(6-chloro-2-cyclopropylmethyl-3-oxo-2,3-dihydro-1H-isoindol-1-yl)acetyl]guanidine,
N-[(5-chloro-3-oxo-2-(2,2,2-trifluoroethyl)-2,3-dihydro-1H-isoindol-1-yl)acetyl]guanidine,
N-[(6-chloro-3-oxo-2-(2,2,2-trifluoroethyl)-2,3-dihydro-1H-isoindol-1-yl)acetyl]guanidine,
N-[(5-chloro-3-oxo-2-(3,3,3-trifluoropropyl)-2,3-dihydro-1H-isoindol-1-yl)acetyl]guanidine,
N-[(6-chloro-3-oxo-2-(3,3,3-trifluoropropyl)-2,3-dihydro-1H-isoindol-1-yl)acetyl]guanidine,
N-[(5-chloro-3-oxo-2-(4,4,4-trifluorobutyl)-2,3-dihydro-1H-isoindol-1-yl)acetyl]guanidine,
N-[(6-chloro-3-oxo-2-(4,4,4-trifluorobutyl)-2,3-dihydro-1H-isoindol-1-yl)acetyl]guanidine, N-[(5,6-dichloro-2-isobutyl-3-oxo-2,3-dihydro-1H-isoindol-1-yl)acetyl]guanidine,
N-[(7-fluoro-2-isobutyl-3-oxo-2,3-dihydro-1H-isoindol-1-yl)acetyl]guanidine,
N-[(4,7-difluoro-2-isobutyl-3-oxo-2,3-dihydro-1H-isoindol-1-yl)acetyl]guanidine,
N-[(5-bromo-2-isobutyl-3-oxo-2,3-dihydro-1H-isoindol-1-yl)acetyl]guanidine,
N-[(6-bromo-2-isobutyl-3-oxo-2,3-dihydro-1H-isoindol-1-yl)acetyl]guanidine,
N-[(2-isobutyl-3-oxo-5-trifluoromethyl-2,3-dihydro-1H-isoindol-1-yl)acetyl]guanidine,
N-[(2-isobutyl-3-oxo-6-trifluoromethyl-2,3-dihydro-1H-isoindol-1-yl)acetyl]guanidine,
N-[(2-cyclopropylmethyl-3-oxo-5-trifluoromethyl-2,3-dihydro-1H-isoindol-1-yl)acetyl]guanidine,
N-[(2-cyclopropylmethyl-3-oxo-6-trifluoromethyl-2,3-dihydro-1H-isoindol-1-yl)acetyl]guanidine,
N-[(3-oxo-2-(2,2,2-trifluoroethyl)-6-trifluoromethyl-2,3-dihydro-1H-isoindol-1-yl)acetyl]guanidine,
N-[(3-Oxo-2-(2,2,2-trifluoro-ethyl)-5-trifluoromethyl-2,3-dihydro-1H-isoindol-1-yl)acetyl]guanidine,
N-[(3-oxo-5-trifluoromethyl-2-(3,3,3-trifluoropropyl)-2,3-dihydro-1H-isoindol-1-yl)acetyl]guanidine,
N-[(3-oxo-6-trifluoromethyl-2-(3,3,3-trifluoropropyl)-2,3-dihydro-1H-isoindol-1-yl)acetyl]guanidine,
N-[(3-oxo-2-(4,4,4-trifluorobutyl)-5-trifluoromethyl-2,3-dihydro-1H-isoindol-1-yl)acetyl]guanidine,
N-[(3-oxo-2-(4,4,4-trifluorobutyl)-6-trifluoromethyl-2,3-dihydro-1H-isoindol-1-yl)acetyl]guanidine,
[1-(2-guanidino-1-methyl-2-oxoethyl)-3-oxo-1,3-dihydroisoindol-2-yl]acetic acid,
N-{2-[3-oxo-2-(2-pyrrolidin-1-ylethyl)-2,3-dihydro-1H-isoindol-1-yl]propionyl}guanidine,
N-[2-(2-hydroxyethyl)-3-oxo-2,3-dihydro-1H-isoindol-1-yl)propionyl]guanidine,
N-{2-[6-Methanesulfonyl-3-oxo-2-(2,2,2-trifluoro-ethyl)-2,3-dihydro-1H-isoindol-1-yl]acetyl}-guanidine,
N-[2-(2-Cyclopropylmethyl-6-methanesulfonyl-3-oxo-2,3-dihydro-1H-isoindol-1-yl)acetyl]guanidine,
N-{2-[5,6-Difluoro-3-oxo-2-(3,3,3-trifluoro-propyl)-2,3-dihydro-1H-isoindol-1-yl)acetyl}-guanidine,
N-{2-[5,6-Dichloro-3-oxo-2-(3,3,3-trifluoro-propyl)-2,3-dihydro-1H-isoindol-1-yl]-acetyl}-guanidine,
N-[2-(5,6-Dichloro-2-cyclopropylmethyl-3-oxo-2,3-dihydro-1H-isoindol-1-yl)-acetyl]-guanidine,
N-[2-(5,6-Dichloro-2-cyclopropyl-3-oxo-2,3-dihydro-1H-isoindol-1-yl)-acetyl]-guanidine,
N-{2-[5,6-Dichloro-3-oxo-2-(2,2,2-trifluoro-ethyl)-2,3-dihydro-1H-isoindol-1-yl]-acetyl}-guanidine,
N-{2-[5,6-Difluoro-3-oxo-2-(2,2,2-trifluoro-ethyl)-2,3-dihydro-1H-isoindol-1-yl]-acetyl}-guanidine,
and racemic mixtures, enantiomers and diastereomers thereof, tautomers thereof and pharmaceutically acceptable salts thereof.

Another preference is given to compounds of the formula I, characterized in that it is chosen from the group of:
(R)-N-{2-[6-Methanesulfonyl-3-oxo-2-(2,2,2-trifluoro-ethyl)-2,3-dihydro-1H-isoindol-1-yl]-acetyl}-guanidine,
(S)-N-{2-[6-Methanesulfonyl-3-oxo-2-(2,2,2-trifluoro-ethyl)-2,3-dihydro-1H-isoindol-1-yl]-acetyl}-guanidine,
(R)-N-[2-(2-Cyclopropylmethyl-3-oxo-6-trifluoromethyl-2,3-dihydro-1H-isoindol-1-yl)acetyl]-guanidine,
(S)-N-[2-(2-Cyclopropylmethyl-3-oxo-6-trifluoromethyl-2,3-dihydro-1H-isoindol-1-yl)acetyl]-guanidine,
(R)-N-{2-[5,6-Difluoro-3-oxo-2-(3,3,3-trifluoro-propyl)-2,3-dihydro-1H-isoindol-1-yl]-acetyl}-guanidine,
(S)-N-{2-[5,6-Difluoro-3-oxo-2-(3,3,3-trifluoro-propyl)-2,3-dihydro-1H-isoindol-1-yl]-acetyl}-guanidine,
(R)-N-{2-[5,6-Dichloro-3-oxo-2-(3,3,3-trifluoro-propyl)-2,3-dihydro-1H-isoindol-1-yl]-acetyl}-guanidine,
(S)-N-{2-[5,6-Dichloro-3-oxo-2-(3,3,3-trifluoro-propyl)-2,3-dihydro-1H-isoindol-1-yl]-acetyl}-guanidine,
(R)-N-[2-(5,6-Dichloro-2-cyclopropylmethyl-3-oxo-2,3-dihydro-1H-isoindol-1-yl)-acetyl]-guanidine,
(S)-N-[2-(5,6-Dichloro-2-cyclopropylmethyl-3-oxo-2,3-dihydro-1H-isoindol-1-yl)-acetyl]-guanidine,
(R)-N-[2-(5,6-Dichloro-2-cyclopropyl-3-oxo-2,3-dihydro-1H-isoindol-1-yl)-acetyl]-guanidine,
(S)-N-[2-(5,6-Dichloro-2-cyclopropyl-3-oxo-2,3-dihydro-1H-isoindol-1-yl)-acetyl]-guanidine,
(R)-N-{2-[5,6-Dichloro-3-oxo-2-(2,2,2-trifluoro-ethyl)-2,3-dihydro-1H-isoindol-1-yl]-acetyl}-guanidine,
(S)-N-{2-[5,6-Dichloro-3-oxo-2-(2,2,2-trifluoro-ethyl)-2,3-dihydro-1H-isoindol-1-yl]-acetyl}-guanidine,
(R)-N-{2-[3-Oxo-2-(2,2,2-trifluoro-ethyl)-6-trifluoromethyl-2,3-dihydro-1H-isoindol-1-yl]-acetyl}-guanidine,
(S)-N-{2-[3-Oxo-2-(2,2,2-trifluoro-ethyl)-6-trifluoromethyl-2,3-dihydro-1H-isoindol-1-yl]-acetyl}-guanidine,
(R)-N-[2-(6-chloro-3-oxo-2-(3,3,3-trifluoropropyl)-2,3-dihydro-1H-isoindol-1-yl)-acetyl]-guanidine,
(S)-N-[2-(6-chloro-3-oxo-2-(3,3,3-trifluoropropyl)-2,3-dihydro-1H-isoindol-1-yl)-acetyl]-guanidine,
(R)-N-[2-(5-chloro-3-oxo-2-(3,3,3-trifluoropropyl)-2,3-dihydro-1H-isoindol-1-yl)-acetyl]-guanidine,
(S)-N-[2-(5-chloro-3-oxo-2-(3,3,3-trifluoropropyl)-2,3-dihydro-1H-isoindol-1-yl)-acetyl]-guanidine,
(R)-N-{2-[3-Oxo-6-trifluoromethyl-2-(3,3,3-trifluoro-propyl)-2,3-dihydro-1H-isoindol-1-yl]-acetyl}-guanidine,
(S)-N-{2-[3-Oxo-6-trifluoromethyl-2-(3,3,3-trifluoro-propyl)-2,3-dihydro-1H-isoindol-1-yl]-acetyl}-guanidine,
(R)-N-{2-[3-Oxo-5-trifluoromethyl-2-(3,3,3-trifluoro-propyl)-2,3-dihydro-1H-isoindol-1-yl]-acetyl}-guanidine,
(S)-N-{2-[3-Oxo-5-trifluoromethyl-2-(3,3,3-trifluoro-propyl)-2,3-dihydro-1H-isoindol-1-yl]-acetyl}-guanidine,
(R)-N-{2-[6-Chloro-3-oxo-2-(4,4,4-trifluoro-butyl)-2,3-dihydro-1H-isoindol-1-yl]-acetyl}-guanidine,
(S)-N-{2-[6-Chloro-3-oxo-2-(4,4,4-trifluoro-butyl)-2,3-dihydro-1H-isoindol-1-yl]-acetyl}-guanidine,
(R)-N-{2-[5-Chloro-3-oxo-2-(4,4,4-trifluoro-butyl)-2,3-dihydro-1H-isoindol-1-yl]-acetyl}-guanidine,
(S)-N-{2-[5-Chloro-3-oxo-2-(4,4,4-trifluoro-butyl)-2,3-dihydro-1H-isoindol-1-yl]-acetyl}-guanidine,
(R)-N-{2-[5-Chloro-3-oxo-2-(4,4,4-trifluoro-butyl)-2,3-dihydro-1H-isoindol-1-yl]-acetyl}-guanidine,
(S)-N-{2-[5-Chloro-3-oxo-2-(4,4,4-trifluoro-butyl)-2,3-dihydro-1H-isoindol-1-yl]-acetyl}-guanidine,
(R)-N-[2-(6-Chloro-2-cyclopropylmethyl-3-oxo-2,3-dihydro-1H-isoindol-1-yl)-acetyl]-guanidine,
(S)-N-[2-(6-Chloro-2-cyclopropylmethyl-3-oxo-2,3-dihydro-1H-isoindol-1-yl)-acetyl]-guanidine,
(R)-N-[2-(5-Chloro-2-cyclopropylmethyl-3-oxo-2,3-dihydro-1H-isoindol-1-yl)-acetyl]-guanidine,
(S)-N-[2-(5-Chloro-2-cyclopropylmethyl-3-oxo-2,3-dihydro-1H-isoindol-1-yl)-acetyl]-guanidine
and pharmaceutically acceptable salts and tautomers thereof.

If the inventive compounds contain one or more centers of asymmetry, these may independently of one another have the S and the R configuration. The compounds may be in the form of optical isomers, of diastereomers, of racemates or of mixtures thereof in any ratio.

The present invention encompasses all tautomeric forms of the compounds of the formula I.

Alkyl radicals may be straight-chain or branched. This also applies if they carry substituents or occur as substituents of other radicals, for example in alkylamino, alkylcarbonylamino, alkoxy, alkoxycarbonyl, alkylcarbonyl, polyfluoroalkyl or polyfluoroalkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl) or pentyl. Preferred alkyl radicals are methyl, ethyl, n-propyl, isopropyl, tert-butyl and isobutyl. One or more, for example 1, 2, 3, 4, 5, 6, 7, 8 or 9, hydrogen atoms in alkyl radicals may be replaced by fluorine atoms to form polyfluoroalkyl radicals. Examples of such radicals are difluoromethyl, trifluoromethyl, pentafluoroethyl, 2,2,2-trifluoroethyl; 3,3,3-trifluoropropyl; 3,3,3trifluorobutyl, 4,4,4-trifluorobutyl. Polyfluoroalkoxy radicals are alkoxy radicals of 1 to 3 carbons substituted by 1, 2, 3, 4, 5, 6 or 7 fluorine atoms, in particular trifluoromethoxy.

Examples of cycloalkyl radicals are cyclopropyl, cyclobutyl, cyclopentyl, cyclohexyl, cycloheptyl or cyclooctyl. One or more, for example 1 or 2, hydrogen atoms in cycloalkyl radicals may be replaced by fluorine, chlorine, bromine or iodine atoms, in particular by fluorine atoms. Substituted cycloalkyl radicals may be substituted in any positions.

The alkenyl radicals contain 2, 3, 4, 5 or 6 carbon atoms and 1, 2 or 3 conjugated or non-conjugated double bonds in a straight or branched chain. The alkynyl radicals contain 2, 3, 4, 5 or 6 carbon atoms and 1, 2 or 3 conjugated or non-conjugated triple bonds in a straight or branched chain.

The aryl radicals are chosen from phenyl, 1-naphthyl, 2-naphthyl and indenyl. Substituted aryl radicals may be substituted in any positions.

Heteroaryl radicals are monocyclic or bicyclic aromatic 3, 4, 5, 6, 7, 8, 9 or 10-membered ring compounds in which 1, 2, 3 or 4 ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Examples of heteroaryl are furyl, thienyl, pyrrolyl, imidazolyl, pyrazolyl, triazolyl, tetrazolyl, oxazolyl, isoxazolyl, thiazolyl, isothiazolyl, pyridinyl, pyrazinyl, pyrimidinyl, pyridazinyl, indolyl, indazolyl, quinolyl, isoquinolyl, phthalazinyl, quinoxalinyl, quinazolinyl and cinnolinyl, in particular thiazolyl, thienyl, pyrrolyl, pyridazinyl, pyridinyl, pyrimidinyl, furyl, imidazolyl, isoxazolyl, oxazolyl, pyrazinyl, tetrazolyl and triazolyl. Substituted heteroaryl radicals may be substituted in any positions.

The compounds of the formula I inhibit the cellular sodium-proton antiporter ($Na^+/H^+$-exchanger, NHE), in particular they inhibit the subtype NHE1. Because of the NHE-inhibitory properties, the compounds of the formula I and/or the pharmaceutically acceptable salts thereof are suitable for the prevention and treatment of diseases caused by activation of or activated NHE, and of diseases caused secondarily by the NHE-related damage.

Since NHE inhibitors predominantly act via their effect on cellular pH regulation, they can generally be combined beneficially with other compounds which regulate the intracellular pH, with suitable combination partners being inhibitors of the carbonate dehydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine, in particular human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors of the formula I and/or the pharmaceutically acceptable salts thereof are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of the formula I and/or the pharmaceutically acceptable salts thereof used according to the invention can, because of inhibition of the cellular $Na^+/H^+$ exchange mechanism, be used as medicaments for the treatment of all acute or chronic ischemia-induced damage or diseases induced primarily or secondarily thereby.

This also relates to their use as medicaments for surgical interventions. Thus, the compounds can be used during organ transplantations, it being possible to use the compounds both to protect the organs in the donor before and during the removal, to protect removed organs for example during treatment with or storage thereof in physiological bath liquids, and during transfer to the recipient organism.

The compounds of the invention are likewise valuable medicaments with a protective effect when performing angioplastic surgical interventions, for example on the heart as well as on peripheral organs and vessels.

It has emerged that the compounds of the invention are exceptionally effective medicaments for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of the formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of the formula I and/or the pharmaceutically acceptable salts thereof can be used when there is heart-damaging overproduction of thyroid hormones, thyrotoxicosis, or on external supply of thyroid hormones. The compounds of the formula I and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, being suitable for example for the treatment of stroke or of cerebral edema.

The compounds of the formula I and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonate dehydratase inhibitors, for example with acetazolamide, and with other inhibitors of NHE or of the sodium-dependent chloride-bicarbonate exchanger (NCBE).

The compounds according to the invention of the formula I and/or the pharmaceutically acceptable salts thereof are additionally likewise suitable for the treatment of types of shock such as, for example, of allergic, cardiogenic, hypovolemic and bacterial shock.

The compounds of the formula I and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonate dehydratase such as, for example, with acetazolamide, is particularly beneficial.

The compounds of the formula I and/or the pharmaceutically acceptable salts thereof used according to the invention are additionally distinguished by a strong inhibitory effect on the proliferation of cells, for example fibroblast proliferation and the proliferation of smooth vascular muscle cells. The compounds of the formula I and/or the pharmaceutically acceptable salts thereof are therefore suitable as valuable therapeutic agents for diseases in which cellular proliferation represents a primary or secondary cause, and can therefore be used as antiatherosclerotics, agents for chronic renal failure, cancers.

It was possible to show that cell migration is inhibited by NHE inhibitors. The compounds of the formula I and/or the pharmaceutically acceptable salts thereof are therefore suitable as valuable therapeutic agents for diseases in which cell migration represents a primary or secondary cause, such as, for example, cancers with a pronounced tendency to metastasis.

The compounds of the formula I and/or the pharmaceutically acceptable salts thereof are further distinguished by a retardation or prevention of fibrotic disorders. They are thus suitable as excellent agents for the treatment of cardiac fibroses, and of pulmonary fibrosis, hepatic fibrosis, renal fibrosis and other fibrotic disorders. They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of the formula I and/or the pharmaceutically acceptable salts thereof are suitable for the prevention and treatment of high blood pressure and of cardiovascular disorders. In these cases they can be used alone or with a suitable combination and formulation partner for the treatment of high blood pressure and of cardiovascular disorders. Thus, for example, they can be combined with one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone. The NHE inhibitors of the present invention can further be used in combination with calcium channel blockers such as verapamil, diltiazem, amlodipine or nifedipine, and with ACE inhibitors such as, for example, ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan; omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors of the formula I and/or the pharmaceutically acceptable salts thereof have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs. The compounds of the invention can also be used for the treatment of disorders caused by protozoa, of malaria and of coccidiosis in poultry.

It has additionally been found that compounds of the formula I and/or the pharmaceutically acceptable salts thereof show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the compounds of the formula I and/or the pharmaceutically acceptable salts thereof lead to a marked reduction in the infarctions induced by metabolic abnormalities and, in particular, to a significant reduction in the induced infarct size and the severity thereof. Said compounds are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of the formula I and/or the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I and/or the pharmaceutically acceptable salts thereof, proves to be a favorable combination with enhanced effect and reduced use of active ingredients.

Thus, compounds of the formula I and/or the pharmaceutically acceptable salts thereof lead to effective protection against endothelial damage of various origins. This protection of the vessels against the syndrome of endothelial dysfunction means that the compounds of the formula I and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that compounds of the formula I and/or the pharmaceutically acceptable salts thereof are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as meffornin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, the compounds of the formula I and/or the pharmaceutically acceptable salts thereof counteract the development of late complications of diabetes and can therefore be used as medicaments for the prevention and treatment of late damage from diabetes, such as diabetic nephropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

The NHE inhibitors of the invention of the formula I and/or the pharmaceutically acceptable salts thereof show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. The compounds of the formula I and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of the formula I and/or the pharmaceutically acceptable salts thereof are thus outstandingly suitable for the treatment and prevention of heart failure, of congestive heart failure (CHF).

Whereas preceding patents and patent applications have claimed the treatment of various forms of cancer which have already occurred, it was now extremely surprising that not only is it possible to cure a cancer which has already occurred through inhibition of proliferation, but there is also prevention and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of the formula I and/or the pharmaceutically acceptable salts thereof are thus outstandingly suitable for the treatment and, in particular, the prevention of age-related types of cancer.

There is now found to be not only a delay, shifted highly significantly in time and beyond the normal statistical extent, in the occurrence of age-related disorders of all the organs investigated, including the heart, vessels, liver etc., and a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{2+}$ antagonists etc. or with metabolism-normalizing medicaments such as cholesterol-lowering agents.

The compounds of the formula I and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

The present invention also relates to processes for the synthesis of isoindolone derivatives of the formula I

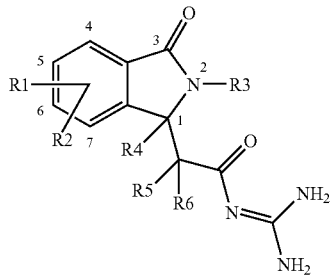

Moreover, the compounds of the formula I may be in the form of tautomers, racemic mixtures, enantiomers and diastereomers. These forms also form part of the invention. The compounds of the formula I, in which R4 and R6 represent hydrogen can be prepared from the phthalimides of the formula (II) according to the following general synthetic scheme:

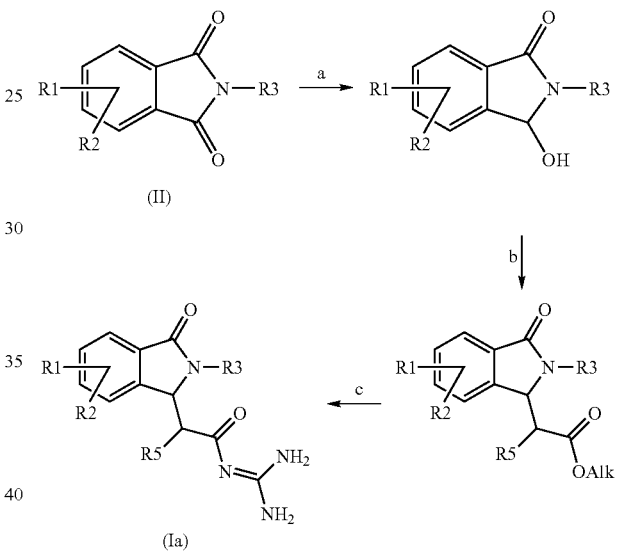

The general synthetic scheme is as follows:
a) a complex hydride is reacted with a phthalimide (of the formula II) in an aliphatic alcohol
b) the product obtained is then reacted with an alkoxycarbonylmethylenetriphenylphosphorane in toluene, or with a trialkyl phosphonoacetate and a base
c) the product obtained is reacted with guanidinium chloride and a base or with guanidine in e.g. an alcohol having 1, 2, 3 or 4 carbon atoms.

The reduction reaction a is preferably carried out using a hydride, such as potassium borohydride or sodium borohydride, in an aliphatic alcohol having 1, 2, 3 or 4 carbon atoms, preferably methanol, or in tetrahydrofuran, at a temperature of between 0° C. and the boiling point of the reaction mixture.

Reaction b is generally carried out in the presence of a suitable alkoxycarbonylmethylenetriphenylphosphorane in a solvent, such as toluene, at a temperature of between 20° C. and the boiling point of the reaction mixture, or in the presence of a suitable trialkyl phosphonoacetate and a base, such as sodium hydride in a solvent, such as 1,2-dimethoxyethane, at a temperature of between 0° C. and the boiling point of the reaction mixture.

Reaction c is generally carried out in the presence of guanidinium hydrochloride and a base, such as potassium tert-butoxide in an inert solvent, such as dimethylformamide, at a temperature of between 20° C. and the boiling point of the reaction mixture, or in the presence of guanidine in a solvent, such as an alcohol having 1, 2, 3 or 4 carbon atoms, preferably isopropanol, at a temperature of between 20° C. and the boiling point of the reaction mixture.

Alternatively, certain compounds of the formula I, in which R4 and R6 represent hydrogen can be prepared from the aldehydes of the formula (III) according to the following general synthetic scheme:

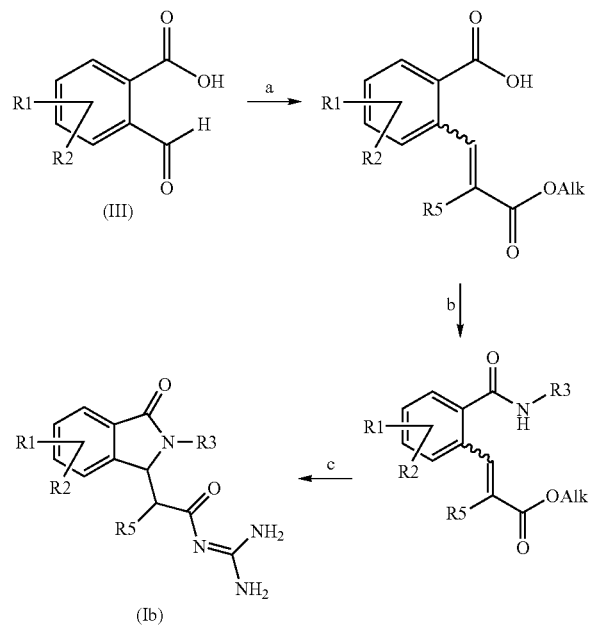

The general synthetic scheme is as follows:
a) a compound of the formula III is reacted with alkoxycarbonylmethylenetriphenylphosphorane in toluene or with a trialkyl phosphonoacetate and a base
b) the product obtained is reacted with an amine of the formula R3NH$_2$ (R3 having the same meaning as in formula I) and a carbodiimide
c) the product obtained is placed in contact with guanidinium chloride and a base or with guanidine in e.g. an alcohol having 1, 2, 3 or 4 carbon atoms.

Reaction a is generally carried out in the presence of a suitable alkoxycarbonylmethylenetriphenylphosphorane in an inert solvent, such as toluene, at a temperature of between 20° C. and the boiling point of the reaction mixture, or in the presence of a suitable trialkyl phosphonoacetate and a base, such as sodium hydride in a solvent, such as 1,2-dimethoxyethane, at a temperature of between 0° C. and the boiling point of the reaction mixture.

Reaction b is carried out in the presence of the appropriate amine R3NH$_2$. The process is generally performed in the presence of a coupling agent used in peptide chemistry, such as a carbodiimide (for example N,N'-dicyclohexylcarbodiimide) or N,N'-carbonyldiimidazole, in an inert solvent, such as an ether (for example tetrahydrofuran or dioxane), an amide (for example dimethylformamide) or a chlorinated inert solvent (for example methylene chloride, 1,2-dichloroethane or chloroform), at a temperature of between 0° C. and the boiling point of the reaction mixture.

Reaction c is generally carried out in the presence of guanidinium hydrochloride and a base, such as potassium tert-butoxide, in an inert solvent, such as dimethylformamide, at a temperature of between 20° C. and the boiling point of the reaction mixture, or in the presence of guanidine in a solvent, such as an alcohol having 1, 2, 3 or 4 carbon atoms, preferably isopropanol, at a temperature of between 20° C. and the boiling point of the reaction mixture.

The compound of the formula I, in which R4 represents an alkyl group and R6 represents hydrogen can be prepared from the phthalimides of the formula (II) according to the following general synthetic scheme:

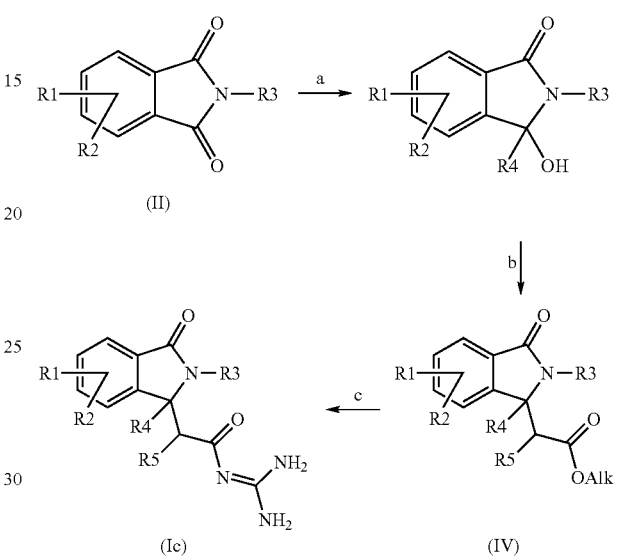

The general synthetic scheme is as follows:
a) a phthalimide (of the formula II) is reacted with an alkylmagnesium halide or with an alkyllithium reagent, e.g. in an ether
b) the product obtained is then reacted with an alkoxycarbonylmethylenetriphenylphosphorane in toluene, or with 1-ethoxy-1-trimethylsiloxyethylene and a Lewis acid
c) the product obtained is reacted with guanidinium chloride and a base or with guanidine, e.g. in an alcohol having 1, 2, 3 or 4 carbon atoms.

Reaction a is preferably carried out using an alkylmagnesium halide or an alkyllithium reagent, in a solvent, such as an ether, preferably tetrahydrofuran, at a temperature of between 0° C. and the boiling point of the reaction mixture.

Reaction b can be carried out in the presence of a suitable alkoxycarbonylmethylenetriphenylphosphorane in a solvent, such as toluene, at a temperature of between 20° C. and the boiling point of the reaction mixture, or in the presence of 1-ethoxy-1 trimethylsiloxyethylene and a Lewis acid, such as titanium(IV) chloride or trimethylsilyl triflate, in an inert solvent, such as dichloromethane, at a temperature of between −78° C. and 20° C. The preparation of derivatives, such as 1-ethoxy-1-trimethylsiloxyethene, is described in Synth. Commun. 1987, 17, 1.

Reaction c is generally carried out in the presence of guanidinium hydrochloride and a base, such as potassium tert-butoxide in an inert solvent, such as dimethylformamide, at a temperature of between 20° C. and the boiling point of the reaction mixture, or in the presence of guanidine in a solvent, such as an alcohol having 1, 2, 3 or 4 carbon atoms, preferably isopropanol, at a temperature of between 20° C.C and the boiling point of the reaction mixture.

The compounds of the formula I, in which R6 represents an alkyl group can be prepared from the esters of the formula (IV) according to the following general synthetic scheme:

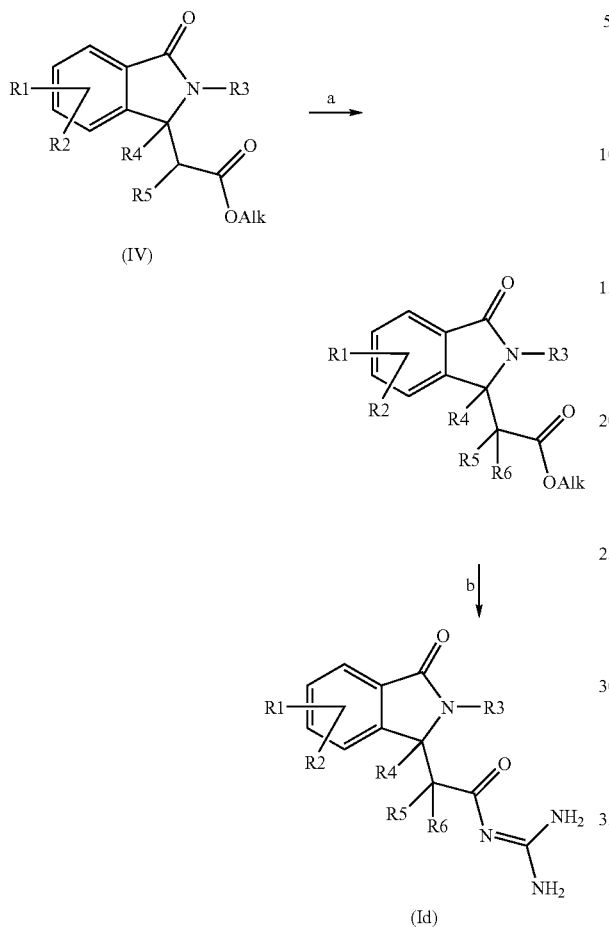

The general synthetic scheme is as follows:
a) the compound of the formula IV is reacted, in the presence of lithium diisopropylamide, with an R6-Hal, where Hal is F, Cl, Br or I.
b) the product obtained is reacted with such as guanidinium chloride and a base or with guanidine, e.g. in an alcohol having 1, 2, 3 or 4 carbon atoms.

Reaction a can be carried out in the presence of lithium diisopropylamide in an inert solvent, such as an ether (preferably tetrahydrofuran) and in the presence of a suitable alkyl halide R6-Hal, at a temperature of between −78° C. and 0° C.

Reaction b is generally carried out in the presence of guanidinium hydrochloride and a base, such as potassium tert-butoxide in an inert solvent, such as dimethylformamide, at a temperature of between 20° C. and the boiling point of the reaction mixture, or in the presence of guanidine in a solvent, such as an alcohol having 1, 2, 3 or 4 carbon atoms, preferably isopropanol, at a temperature of between 20° C. and the boiling point of the reaction mixture.

If the compounds of the formula (II) are not commercially available, they can be prepared, for example (route a), from the corresponding anhydrides of the formula (V) in the presence of the appropriate amine R3NH₂ and an acid, such as para-toluene-sulfonic acid, in a solvent, such as toluene, at a temperature of between 20° C. and the boiling point of the reaction mixture; or (route b) by the Gabriel method, starting with the corresponding potassium phthalimides of the formula (VI) in the presence of the appropriate alkyl halide of the formula R3Hal and in a solvent, such as dimethylformamide, at a temperature of between 0° C. and the boiling point of the reaction mixture, by application or adaptation of the method described in Tetrahedron 1998, 54, 14437.

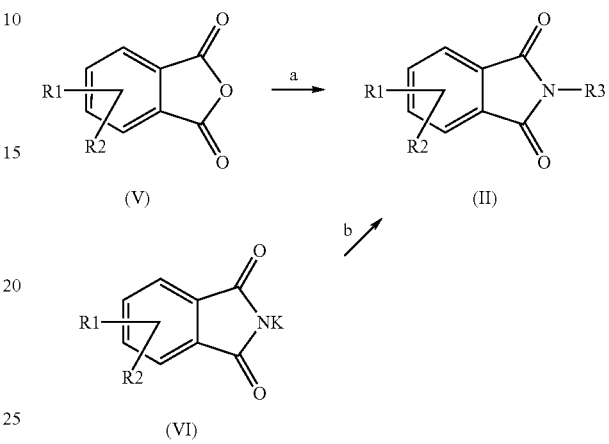

If the compounds of the formula (V) are not commercially available, they can be prepared, for example, from the corresponding phthalic acids in acetic anhydride, at a temperature of between 20° C. and the boiling point of the reaction mixture.

Where necessary, a protecting group for the amine, alcohol or acid function and deprotection methods, such as those described by T. W. Greene, Protective Groups in Organic Synthesis, J. Wiley-Interscience Publication (1991), are used.

The compounds of the formula I can optionally be converted into addition salts with an inorganic or organic acid by reacting such an acid in a solvent, e.g. an organic solvent such as an alcohol, a ketone, an ether or a chlorinated solvent. These salts also form part of the invention. Examples of pharmaceutically acceptable salts that can be mentioned include the following salts: benzenesulfonate, hydrobromide, hydrochloride, acetate, citrate, ethanesulfonate, fumarate, gluconate, iodate, maleate, isethionate, methanesulfonate, methylenebis(β-oxynaphthoate), nitrate, oxalate, pamoate, phosphate, salicylate, succinate, sulfate, tartrate, theophyllinacetate and p-toluenesulfonate.

If the compounds contain an acid group, they are capable of forming salts with bases, for example as alkali metal salts, preferably sodium or potassium salts, or as ammonium salts, for example as salts with ammonia or organic amines or amino acids. They can also be present as zwitterion.

List of Abbreviations:

| | |
|---|---|
| ACN | Acetonitrile |
| CDI | Di-imidazol-1-yl-methanone |
| DCI | Desorption-chemical ionization |
| DEA | Diethylamine |
| DIP | 2-Isopropoxy-propane |
| DME | 1,2-Dimethoxyethane |
| DMF | N,N-Dimethylformamide |
| EA | Ethyl acetate |
| EI | Electron impact |

| | |
|---|---|
| ES | Electrospray ionization |
| EtOH | Ethanol |
| HEP | n-Heptane |
| HOAc | Acetic acid |
| HPLC | High performance liquid chromatography |
| KOtBu | Potassium tert.-butylate |
| MeOH | Methanol |
| m.p. | Melting point |
| MTB | 2-Methoxy-2-methyl-propane |
| NMP | 1-Methyl-pyrrolidin-2-one |
| i-PrOH | Isopropanol |
| RT | Retention time |
| TFA | Trifluoroacetic acid |

The following examples illustrate the invention.

EXAMPLE 1 a) N-[2-(2-Methyl-3-oxo-2,3-dihydro-1H-isoindol-1-yl)acetyl]guanidine

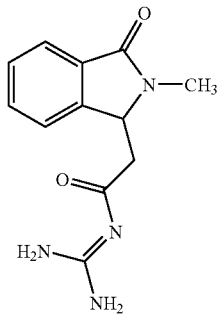

4.3 g of guanidinium chloride are added to a suspension of 5.2 g of potassium tertbutoxide in 100 cm³ of dimethylformamide. The reaction mixture is stirred under an inert atmosphere at a temperature in the region of 20° C. for 1 hour, followed by addition of a solution of 2 g of ethyl (2-methyl-3-oxo-2,3-dihydro-1H-isoindol-1-yl)acetate in 20 cm³ of dimethylformamide. The reaction mixture is stirred at a temperature in the region of 20° C. for 16 hours, followed by addition of 100 cm³ of water. The pH is adjusted to 8 by adding 50 cm³ of 1 N hydrochloric acid, and the mixture is concentrated under reduced pressure (0.6 kPa) at a temperature in the region of 30° C. The evaporation residue is taken up in water and then filtered. 0.35 g of N-[(2-methyl3-oxo-2,3-dihydro-1H-isoindol-1-yl)acetyl]guanidine is thus obtained in the form of an off-white solid melting at 214° C. Mass spectrum EI: m/e 246 (M⁺), m/e 159 (base peak), m/e 146.

b) Ethyl (2-methyl-3-oxo-2,3-dihydro-1H-isoindol-1-yl)acetate 11.5 g of ethoxycarbonylmethylenetriphenylphosphorane are added to a suspension of 4.5 g of 3-hydroxy-2-methyl-2,3-dihydroisoindol-1-one in 110 cm³ of toluene. The reaction mixture is refluxed with stirring for 16 hours and then cooled to a temperature in the region of 20° C. The mixture is then concentrated to dryness under reduced pressure (2 kPa) at a temperature in the region of 40° C. The residual oil is taken up in 50 cm³ of diethyl ether. The precipitate formed is filtered off and then washed twice with 10 cm³ of diethyl ether. The filtrate is concentrated to dryness under reduced pressure (2 kPa) at a temperature in the region of 40° C. to give an orange-colored oil, which is purified by chromatography under argon pressure (60 kPa) on a column of silica gel (particle size 20–45 µm), eluting with successive mixtures of cyclohexane/ethyl acetate (70/30, 65/35, 60/40 by volume). The fractions comprising the expected product are combined and concentrated under reduced pressure (2 kPa) at a temperature in the region of 30° C. 4.1 g of ethyl (2-methyl-3-oxo-2,3-dihydro-1H-isoindol-1-yl)acetate are thus obtained in the form of a yellow oil. (Rf=0.25, thin layer chromatography on silica gel, eluent: cyclohexane/ethyl acetate (50/50 by volume)).

c) 3-Hydroxy-2-methyl-2,3-dihydroisoindol-1-one 3.4 g of potassium borohydride are added slowly to a suspension of 10 g of N-methylphthalimide in 220 cm³ of methanol under an inert atmosphere. The reaction mixture is stirred at a temperature in the region of 20° C. for 20 hours, followed by dropwise addition of 200 cm³ of distilled water. The solvent is then partially evaporated off (about 120 cm³) under reduced pressure (2 kPa) at a temperature in the region of 35° C., and the residue is diluted with 400 cm³ of distilled water. The mixture is extracted with 400 cm³ of ethyl acetate. The organic phase is dried over magnesium sulfate, filtered and then concentrated to dryness under reduced pressure (2 kPa) at a temperature in the region of 30° C. 4.5 g of 3-hydroxy-2-methyl-2,3-dihydroisoindol-1-one are thus obtained in the form of a white powder melting at 130° C.

EXAMPLE 2 a) N-[2-(2-Isobutyl-3-oxo-2,3-dihydro-1H-isoindol-1-yl)acetyl]guanidine

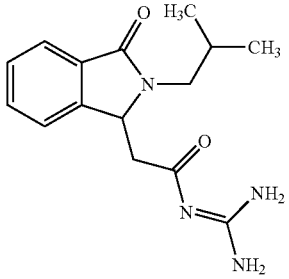

N-[(2-Isobutyl-3-oxo-2,3-dihydro-1H-isoindol-1-yl)acetyl]guanidine is prepared as described in Example 1, starting with 5 g of potassium tert-butoxide, 5.2 g of guanidinium chloride and 2.5 g of ethyl (2-isobutyl-3-oxo-2,3-dihydro-1H-isoindol1-yl)acetate. The reaction mixture is stirred at a temperature in the region of 20° C. for 24 hours and is then filtered. The filtrate is taken up in 150 cm³ of water and 200 cm³ of ethyl acetate. After separation of the phases by settling, the organic phase is separated out and the aqueous phase is extracted with twice 200 cm³ of ethyl acetate. The organic extracts are combined, dried over magnesium sulfate, filtered and concentrated to dryness under reduced pressure (0.6 kPa) at a temperature in the region of 45° C. The evaporation residue is taken up in diethyl ether and the precipitate formed is filtered and then washed several times with diethyl ether. The solid is dried under reduced pressure (10 Pa) at a temperature in the region of 45° C. 1.5 g of N-[(2isobutyl-3-oxo-2,3-dihydro-1H-isoindol-1-yl)acetyl]guanidine are thus obtained in the form of a white solid melting at 250° C. Mass spectrum EI: m/e 288 (M⁺), m/e 201 (base peak).

b) Ethyl (2-Isobutyl-3-oxo-2,3-dihydro-1H-isoindol-1-yl)acetate 7.7 cm³ of triethyl phosphonoacetate are added dropwise, while keeping the temperature below 10° C., to a suspension of 1.6 g of 60% sodium hydride in 60 cm³ of 1,2-dimethoxyethane under an inert atmosphere and cooled to 0° C., with stirring. The reaction mixture is allowed to warm to a temperature in the region of 20° C. and is then stirred for 45 minutes. 5.3 g of 3-hydroxy-2-isobutyl-2,3-dihydroisoindol-1-one are then added and the mixture is refluxed for 3.5 hours and then cooled to a temperature in the region of 20° C. The reaction mixture is treated with 40 cm³ of distilled water and then 100 cm³ of diethyl ether. After separation of the phases by settling, the aqueous phase is extracted twice with 100 cm³ of diethyl ether. The organic extracts are combined, dried over magnesium sulfate, filtered and then concentrated to dryness under reduced pressure (2 kPa) at a temperature in the region of 18° C., to give a pale yellow oil, which is purified by chromatography under argon pressure (60 kPa), on a column of silica gel (particle size 15–40 µm), eluting with successive mixtures of cyclohexane/ethyl acetate (60/40 and then 50/50 by volume). The fractions comprising the expected product are combined and concentrated to dryness under reduced pressure (2 kPa) at a temperature in the region of 30° C. 6.3 g of ethyl (2-isobutyl-3oxo-2,3-dihydro-1H-isoindol-1-yl) acetate are thus obtained in the form of a pale yellow oil. (Rf=0.56, thin layer chromatography on silica gel, eluent: cyclohexane/ethyl acetate (50/50 by volume)).

c) 3-Hydroxy-2-isobutyl-2,3-dihydroisoindol-1-one

3-Hydroxy-2-isobutyl-2,3-dihydroisoindol-1-one is prepared as described in Example 1, starting with 6.5 g of N-isobutylphthalimide in 60 cm³ of methanol and 1.7 g of potassium borohydride. The reaction mixture is stirred at a temperature in the region of 20° C. for 20 hours and is then cooled to a temperature in the region of 0° C., followed by dropwise addition of 50 cm³ of distilled water. The methanol is then partially evaporated off under reduced pressure (2 kPa) at a temperature in the region of 35° C., and the residue is extracted three times with 60 cm³ of dichloromethane. The organic extracts are combined, dried over magnesium sulfate, filtered and then concentrated to dryness under reduced pressure (2 kPa) at a temperature in the region of 25° C. to give a pale yellow oil, which is purified by chromatography under argon pressure (60 kPa) on a column of silica gel (particle size 40–63 µm), eluting with a cyclohexane/ethyl acetate mixture (60/40 by volume). The fractions comprising the expected product are combined and concentrated to dryness under reduced pressure (2 kPa) at a temperature in the region of 40° C. 5.8 g of 3-hydroxy-2-isobutyl-2,3-dihydroisoindol-1-one are thus obtained in the form of a white solid melting at 82° C.

d) N-Isobutylphthalimide

A solution of 3.2 cm³ of isobutylamine in 3 cm³ of toluene is added to a suspension of 5.2 g of phthalic anhydride in 50 cm³ of toluene, with stirring. The reaction mixture is heated at a temperature in the region of 60° C. for 1 hour, and then at a temperature in the region of 100° C. for 2 hours. Dean-Stark apparatus is then installed on the reactor and the reaction mixture is heated at a temperature in the region of 130° C. for 2 hours, after which it is cooled to a temperature in the region of 20° C. The reaction mixture is concentrated to dryness under reduced pressure (2 kPa) at a temperature in the region of 40° C. The residue is taken up in 50 cm³ of saturated sodium bicarbonate solution and extracted twice with 75 cm³ of dichloromethane. The organic extracts are combined, dried over magnesium sulfate, filtered and then concentrated to dryness under reduced pressure (2 kPa) at a temperature in the region of 20° C. 6.5 g of N-isobutylphthalimide are thus obtained in the form of a white solid melting at 92° C.

EXAMPLE 3 a) (−)-N-[2-(2-Isobutyl-3-oxo-2,3-dihydro-1H-isoindol-1-yl)acetyl]guanidine

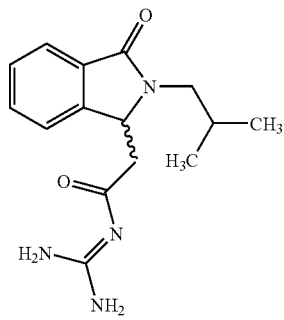

(−)-N-[(2-Isobutyl-3-oxo-2,3-dihydro-1H-isoindol-1-y)acetyl]guanidine is prepared as described in Example 1, starting with 2.6 g of potassium tert-butoxide, 2.6 g of guanidinium chloride and 1.25 g of ethyl (−)-(2-isobutyl-3-oxo-2,3-dihydro-1H-isoindol1-y)acetate. The reaction mixture is stirred at a temperature in the region of 20° C. for 40 hours and is then filtered. The filtrate is taken up in 80 cm³ of water and 120 cm³ of ethyl acetate. After separation of the phases by settling, the organic phase is separated out and the aqueous phase is extracted with twice 120 cm³ of ethyl acetate. The organic extracts are combined, dried over magnesium sulfate, filtered and concentrated to dryness under reduced pressure (0.6 kPa) at a temperature in the region of 40° C. The evaporation residue is taken up in 30 cm³ of diethyl ether and the precipitate formed is filtered off and then washed three times with 5 cm³ of diethyl ether. The solid is dried under reduced pressure (10 Pa) at a temperature in the region of 45° C. 0.75 g of (−)-N-[(2-isobutyl-3-oxo-2,3-dihydro-1H-isoindol-1-yl)acetyl]guanidine is thus obtained in the form of an off-white solid melting at 264° C. ($\alpha_D^{20}$=−10.2°±0.6 in methanol at 0.5%). Mass spectrum EI: m/e 288 (M⁺), m/e 245, m/e 201, m/e 132.

b) Ethyl (−)-(2-isobutyl-3-oxo-2,3-dihydro-1H-isoindol-1-yl)acetate and ethyl (+)-(2-isobutyl-3-oxo-2,3-dihydro-1H-isoindol-1-yl)acetate Ethyl (−)-(2-isobutyl-3-oxo-2,3-dihydro-1H-isoindol-1-yl)acetate and ethyl (+)-(2-isobutyl-3-oxo-2,3-dihydro-1H-isoindol-1-yl)acetate are obtained by resolution of 3.0 g of ethyl (2-isobutyl-3-oxo-2,3-dihydro-1H-isoindol-1-yl) acetate by HPLC chromatography on a 10 µm WHELK-01SS chiral column, eluting successively with heptane/isopropanol (90/10 by volume) and then heptane/ethanol (90/10 and then 50/50 by volume) mixtures. The fractions comprising the first enantiomer are combined and concentrated under reduced pressure (1 kPa) at a temperature in the region of 40° C. The residue is dried under reduced pressure (3 kPa) at a temperature in the region of 40° C. 1.3 g of ethyl (−)-(2-isobutyl-3-oxo-2,3-dihydro-1H-isoindol-1-yl)acetate are thus obtained in the form of a viscous pale ochre-colored

23 oil ($\alpha_D^{20}$=−16.2°±0.6° in DMSO at 0.5%). The fractions comprising the second enantiomer are combined and concentrated under reduced pressure (1 kPa) at a temperature in the region of 40° C. The residue is dried under reduced pressure (3 kPa) at a temperature in the region of 40° C. 1.0 g of ethyl (+)-(2-isobutyl-3-oxo-2,3-dihydro-1H-isoindol-1-yl)acetate is thus obtained in the form of a viscous pale yellow oil ($\alpha_D^{20}$=−15.1°±0.7° in DMSO at 0.5%). Ethyl (2-isobutyl-3-oxo-2,3-dihydro-1H-isoindol-1-yl)acetate is describedin Example 2.

EXAMPLE 4

(+)-N-[2-(2-Isobutyl-3-oxo-2,3-dihydro-1H-isoindol-1-yl)acetyl]guanidine

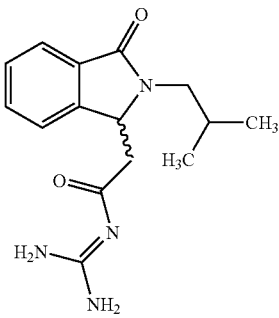

(+)-N-[(2-Isobutyl-3-oxo-2,3-dihydro-1H-isoindol-1-yl)acetyl]guanidine is prepared as described in Example 1, starting with 2.0 g of potassium tert-butoxide, 2.1 g of guanidinium chloride and 1.0 g of ethyl (+)-(2-isobutyl-3-oxo-2,3-dihydro-1H-isoindol1-y)acetate. The reaction mixture is stirred at a temperature in the region of 20° C. for 40 hours and is then filtered. The filtrate is taken up in 70 cm³ of water and 100 cm³ of ethyl acetate. After separation of the phases by settling, the organic phase is separated out and the aqueous phase is extracted with twice 100 cm³ of ethyl acetate. The organic extracts are combined, dried over magnesium sulfate, filtered and concentrated to dryness under reduced pressure (0.6 kPa) at a temperature in the region of 40° C. The evaporation residue is taken up in 30 cm³ of diethyl ether and the precipitate formed is filtered off and then washed three times with 5 cm³ of diethyl ether. The solid is dried under reduced pressure (10 Pa) at a temperature in the region of 45° C. 0.56 g of (+)-N-[(2-isobutyl-3-oxo-2,3-dihydro-1H-isoindol-1-yl)acetyl]-guanidine is thus obtained, in the form of an orange-yellow solid melting at 264° C. ($\alpha_D^{20}$=+13.9°±0.6° in methanol at 0.5%). Ethyl (+)-(2-isobutyl-3-oxo-2,3-dihydro-1H-isoindol-1-yl)acetate is described in Example 3. Mass spectrum DCI: m/e 289 (M+H)⁺.

24

EXAMPLE 5 a) N-[2-(3-Oxo-2-propyl-2,3-dihydro-1H-isoindol-1-yl)acetyl]guanidine

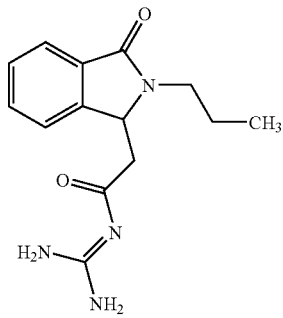

N-[(3-Oxo-2-propyl-2,3-dihydro-1H-isoindol-1-yl)acetyl]guanidine is prepared as described in Example 1, starting with 3.9 g of potassium tert-butoxide, 3.3 g of guanidinium chloride and 1.8 g of ethyl (3-oxo-2-propyl-2,3-dihydro-1H-isoindol1-yl)acetate. The reaction mixture is stirred at a temperature in the region of 20° C. for 1 hour, followed by addition of 60 cm³ of water. The aqueous phase is extracted with 3 times 50 cm³ of ethyl acetate and is then concentrated to dryness under reduced pressure (0.6 kPa) at a temperature in the region of 45° C. The residue is taken up in water, triturated and filtered. The solid is taken up in methanol and the solvent is then evaporated to dryness under reduced pressure (0.6 kPa) at a temperature in the region of 45° C. 0.6 g of N-[(3-oxo-2-propyl-2,3-dihydro-1H-isoindol-1-yl)acetyl]-guanidine is thus obtained in the form of a pale yellow cottony solid melting at 229° C. Mass spectrum EI: m/e 274 (M⁺), m/e 187, m/e 86 (base peak).

b) Ethyl (3-oxo-2-propyl-2,3-dihydro-1H-isoindol-1-yl)acetate

Ethyl (3-oxo-2-propyl-2,3-dihydro-1H-isoindol-1-yl)acetate is prepared as described in Example 2, starting with 0.8 g of 60% sodium hydride in 20 cm³ of 1,2dimethoxyethane, 4.0 cm³ of triethyl phosphonoacetate and 1.9 g of 3-hydroxy-2propyl-2,3-dihydroisoindol-1-one. The crude product is purified by chromatography under argon pressure (60 kPa) on a column of silica gel (particle size 15–40 μm), eluting with a mixture of cyclohexane/ethyl acetate (50/50 by volume). The fractions comprising the expected product are combined and concentrated to dryness under reduced pressure (2 kPa) at a temperature in the region of 30° C. 1.9 g of ethyl (3-oxo-2-propyl-2,3-dihydro-1H-isoindol-1-yl)acetate are thus obtained in the form of a yellow oil. (Rf=0.7, thin layer chromatography on silica gel, eluent: cyclohexane/ethyl acetate (30/70 by volume)).

c) 3-Hydroxy-2-propyl-2,3-dihydroisoindol-1-one

3-Hydroxy-2-propyl-2,3-dihydroisoindol-1-one is prepared as described in Example 1, starting with 1.5 g of N-propylphthalimide in 25 cm³ of methanol and 0.48 g of potassium borohydride. The reaction mixture is stirred at a temperature in the region of 20° C. for 20 hours and is then cooled to a temperature in the region of 0° C. and distilled water is added dropwise. The methanol is then partially evaporated off under reduced pressure (2 kPa) at a temperature in the region of 35° C. and the residue is cooled to 0° C. The precipitate obtained is filtered off and then washed with cold water. The solid is taken up in dichloromethane and the solvent is then evaporated to dryness under reduced pressure (2 kPa) at a temperature in the region of 35° C. 1.0 g of 3-hydroxy-2propyl-2,3-dihydroisoindol-1-one is thus obtained in the form of a beige-colored powder. (Rf=0.6, thin layer chromatography on silica gel, eluent: cyclohexane/ethyl acetate (30/70 by volume)).

EXAMPLE 6 a) N-[2-(2-Ethyl-3-oxo-2,3-dihydro-1H-isoindol-1-yl)acetyl]guanidine

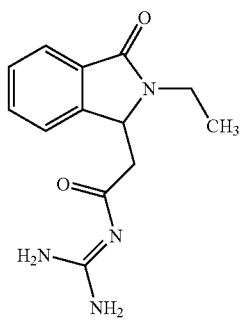

N-[(2-Ethyl-3-oxo-2,3-dihydro-1H-isoindol-1-yl)acetyl]guanidine is prepared as described in Example 1, starting with 4.3 g of potassium tert-butoxide, 3.7 g of guanidinium chloride and 1.9 g of ethyl (2-ethyl-3-oxo-2,3-dihydro-1H-isoindol-1-yl)acetate. The reaction mixture is stirred at a temperature in the region of 20° C. for 20 hours, followed by addition of 60 cm³ of water. The aqueous phase is extracted with 3 times 50 cm³ of ethyl acetate and is then concentrated to dryness under reduced pressure (0.6 kPa) at a temperature in the region of 45° C. The residue is taken up in water, triturated and filtered. The solid is taken up in methanol and the solvent is then evaporated to dryness under reduced pressure (0.6 kPa) at a temperature in the region of 45° C. 0.56 g of N-[(2-ethyl-3-oxo-2,3-dihydro-1H-isoindol-1-yl)acetyl]-guanidine is thus obtained in the form of an off-white solid melting at 223° C. Mass spectrum EI: m/e 260 (M⁺), m/e 173, m/e 160, m/e 132.

b) Ethyl (2-ethyl-3-oxo-2,3-dihydro-1H-isoindol-1-yl)acetate

Ethyl (2-ethyl-3-oxo-2,3-dihydro-1H-isoindol-1-yl)acetate is prepared as described in Example 2, starting with 0.6 g of 60% sodium hydride in 20 cm³ of 1,2-dimethoxyethane, 3.2 cm³ of triethyl phosphonoacetate and 1.8 g of 3-hydroxy-2-ethyl-2,3dihydroisoindol-1-one. The crude product is purified by chromatography under argon pressure (60 kPa) on a column of silica gel (particle size 15–40 µm), eluting with a cyclohexane/ethyl acetate mixture (50/50 by volume). The fractions comprising the expected product are combined and concentrated to dryness under reduced pressure (2 kPa) at a temperature in the region of 30° C. 2.0 g of ethyl (2-ethyl-3-oxo-2,3dihydro-1H-isoindol-1-yl)acetate are thus obtained in the form of a pale yellow oil. (Rf=0.7, thin layer chromatography on silica gel, eluent: dichloromethane/methanol (90/10 by volume)).

c) 3-Hydroxy-2-ethyl-2,3-dihydroisoindol-1-one

3-Hydroxy-2-ethyl-2,3-dihydroisoindol-1-one is prepared as described in Example 1, starting with 4.0 g of N-ethylphthalimide in 20 cm³ of methanol and 1.2 g of potassium borohydride. The reaction mixture is stirred at a temperature in the region of 20° C. for 20 hours and is then cooled to a temperature in the region of 0° C. and distilled water is added dropwise. The precipitate obtained is filtered off and then washed with cold water. The methanol is then partially evaporated from the filtrate under reduced pressure (2 kPa) at a temperature in the region of 35° C., and the residue is cooled to 0° C. The second precipitate thus obtained is filtered off and then washed with cold water. The two fractions of solid are dried under reduced pressure (2 kPa) at a temperature in the region of 35° C. 1.9 g of 3-hydroxy-2-ethyl-2,3-dihydroisoindol-1-one are thus obtained in the form of a flaky white powder. (Rf=0.5, thin layer chromatography on silica gel, eluent: cyclohexane/ethyl acetate (30/70 by volume)).

EXAMPLE 7

N-[2-(2-Isopropyl-3-oxo-2,3-dihydro-1H-isoindol-1-yl)acetyl]guanidine

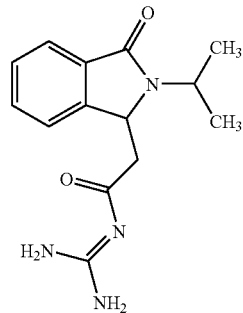

N-[(2-Isopropyl-3-oxo-2,3-dihydro-1H-isoindol-1-yl)acetyl]guanidine is prepared as described in Example 1, starting with 1.5 g of potassium tert-butoxide, 1.3 g of guanidinium chloride and 0.7 g of ethyl (2-isopropyl-3-oxo-2,3-dihydro-1H-isoindol1-yl)acetate. The reaction mixture is stirred at a temperature in the region of 20° C. for 20 hours, followed by addition of 30 cm³ of water. The aqueous phase is extracted with 3 times 50 cm³ of ethyl acetate and is then concentrated to dryness under reduced pressure (0.6 kPa) at a temperature in the region of 45° C. The residue is taken up in water, triturated and filtered. The solid is taken up in a mixture of dichloromethane/methanol (90/10 by volume) and filtered, and the filtrate is purified by chromatography under argon pressure (60 kPa), on a column of silica gel (particle size 15–40 µm), eluting with a dichloromethane/methanol mixture (90/10 by volume). The fractions comprising the expected product are combined and concentrated to dryness under reduced pressure (2 kPa) at a temperature in the region of 40° C. 0.05 g of N-[(2isopropyl-3-oxo-2,3-dihydro-1H-isoindol-1-yl)acetyl]guanidine is thus obtained in the form of a white solid. Mass spectrum EI: m/e 274 (M⁺), m/e 187, m/e 132. Infrared spectrum (KBr): 3412; 1974; 1667; 1603; 1531; 1367 and 698 cm⁻¹.

b) Ethyl (2-isopropyl-3-oxo-2,3-dihydro-1H-isoindol-1-yl)acetate

Ethyl (2-isopropyl-3-oxo-2,3-dihydro-1H-isoindol-1-yl)acetate is prepared as described in Example 2, starting with 0.63 g of 60% sodium hydride in 20 cm³ of 1,2-dimethoxyethane, 3.1 cm³ of triethyl phosphonoacetate and 2.0 g of 3-hydroxy-2isopropyl-2,3-dihydroisoindol-1-one.

The crude product is purified by chromatography under argon pressure (60 kPa) on a column of silica gel (particle size 15–40 µm), eluting with a cyclohexane/ethyl acetate mixture (60/40 by volume). The fractions comprising the expected product are combined and concentrated to dryness under reduced pressure (2 kPa) at a temperature in the region of 30° C. 0.84 g of ethyl (2-isopropyl-3-oxo-2,3-dihydro-1H-isoindol-1-yl)acetate is thus obtained in the form of a pale yellow oil. (Rf=0.7, thin layer chromatography on silica gel, eluent: dichloromethane/methanol (90/10 by volume)).

c) 3-Hydroxy-2-isopropyl-2,3-dihydroisoindol-1-one

3-Hydroxy-2-isopropyl-2,3-dihydroisoindol-1-one is prepared as described in Example 1, starting with 4.0 g of N-isopropylphthalimide in 20 cm³ of methanol and 1.1 g of potassium borohydride. The reaction mixture is stirred at a temperature in the region of 20° C. for 20 hours and is then cooled to a temperature in the region of 0° C. and distilled water is added dropwise. The solvent is then evaporated to dryness under reduced pressure (2 kPa) at a temperature in the region of 35° C. 6.1 g of 3-hydroxy-2isopropyl-2,3-dihydroisoindol-1-one are thus obtained in the form of a white wax. (Rf=0.65, thin layer chromatography on silica gel, eluent: cyclohexane/ethyl acetate (30/70 by volume)).

EXAMPLE 8 a) N-[2-(2-Cyclopropylmethyl-3-oxo-2,3-dihydro-1H-isoindol-1-yl)acetyl]guanidine

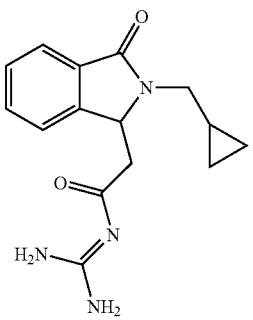

N-[(2-Cyclopropylmethyl-3-oxo-2,3-dihydro-1H-isoindol-1-yl)acetyl]guanidine is prepared as described in Example 1, starting with 2.9 g of potassium tert-butoxide, 2.5 g of guanidinium chloride and 1.5 g of ethyl (2-cyclopropylmethyl-3-oxo-2,3-dihydro-1H-isoindol-1-yl) aceta The reaction mixture is stirred at a temperature in the region of 20° C. for 20 hours, followed by addition of 20 cm³ of water. The aqueous phase is extracted With 3 times 100 cm³ of ethyl acetate. The organic extracts are combined and then concentrated to dryness under reduced pressure (0.6 kPa) at a temperature in the region of 35° C. The residue is taken up in water, triturated, filtered off and then dried in a desiccator. 1.2 g of N-[(2-cyclopropylmethyl-3-oxo-2,3-dihydro-1H-isoindol1-yl)acetyl]guanidine are thus obtained in the form of an off-white powder melting at 229° C. Mass spectrum: DCI: m/e 287 (M+H)⁺.

b) Ethyl (2-cyclopropyl methyl-3-oxo-2,3-dihydro-1H-isoindol-1-yl)acetate

Ethyl (2-cyclopropylmethyl-3-oxo-2,3-dihydro-1H-isoindol-1-yl)acetate is prepared as described in Example 2, starting with 0.61 g of 60% sodium hydride in 20 cm³ of 1,2dimethoxyethane, 3.0 cm³ of triethyl phosphonoacetate and 1.55 g of 3-hydroxy2-cyclopropylmethyl-2,3-dihydroisoindol-1-one. The crude product is purified by chromatography under argon pressure (60 kPa) on a column of silica gel (particle size 15–40 µm), eluting with a mixture of cyclohexane/ethyl acetate (70/30 by volume). The fractions comprising the expected product are combined and concentrated to dryness under reduced pressure (2 kPa) at a temperature in the region of 30° C. 1.45 g of ethyl (2-cyclopropylmethyl-3-oxo-2,3-dihydro-1H-isoindol-1-yl) acetate are thus obtained in the form of a colorless oil (Rf=0.52, thin layer chromatography on silica gel, eluent: cyclohexane/ethyl acetate (50/50 by volume)).

c) 3-Hydroxy-2-cyclopropylmethyl-2,3-dihydroisoindol-1-one

3-Hydroxy-2-cyclopropylmethyl-2,3-dihydroisoindol-1-one is prepared as described in Example 1, starting with 4.3 g of N-cyclopropylmethylphthalimide in 40 cm³ of methanol and 1.2 g of potassium borohydride. The reaction mixture is stirred at a temperature in the region of 20° C. for 20 hours and is then cooled to a temperature in the region of 0° C. and distilled water is added dropwise. The precipitate obtained is filtered off and the solid obtained is then taken up in dichloromethane and concentrated to dryness under reduced pressure (2 kPa) at a temperature in the region of 40° C. 4.1 g of 3-hydroxy-2-cyclopropylmethyl-2,3-dihydroisoindol-1-one are thus obtained in the form of a white powder (Rf=0.38, thin layer chromatography on silica gel, eluent: cyclohexane/ethyl acetate (50/50 by volume)).

d) N-Cyclopropylmethylphthalimide

N-Cyclopropylmethylphthalimide is prepared as described in Example 2, starting with 4 g of phthalic anhydride, 2.3 cm³ of cyclopropylmethylamine and a catalytic amount of para-toluenesulfonic acid in 40 cm³ of toluene. The reaction mixture is heated at a temperature in the region of 140° C. for 2 hours and is then cooled to a temperature in the region of 20° C. and stirred for 16 hours. The reaction mixture is concentrated to dryness under reduced pressure (2 kPa) at a temperature in the region of 40° C. The residue is taken up in dichloromethane and washed twice with saturated aqueous sodium bicarbonate solution. The organic phase is separated out after settling of the phases, dried over magnesium sulfate, filtered and then concentrated to dryness under reduced pressure (2 kPa) at a temperature in the region of 40° C. 4.3 g of N-cyclopropylmethylphthalimide are thus obtained in the form of a cottony white solid (Rf=0.46, thin layer chromatography on silica gel, eluent: cyclohexane/ethyl acetate (40/60 by volume)).

EXAMPLE 9 a) N-[2-(2-Benzyl-3-oxo-2,3-dihydro-1H-isoindol-1-yl)acetyl]guanidine

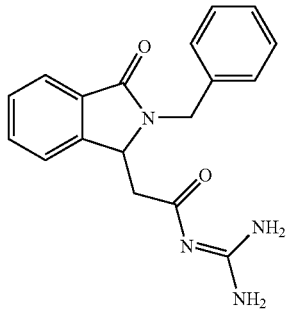

0.22 g of sodium is added to 20 cm³ of absolute ethanol under an inert atmosphere. After the sodium has totally disappeared, 0.94 g of guanidinium chloride is added. The reaction mixture is stirred under an inert atmosphere at a temperature in the region of 20° C. for 1 hour, followed by addition of a solution of 2 g of ethyl (2-benzyl-3-oxo-2,3dihydro-1H-isoindol-1-yl)acetate in 5 cm³ of absolute ethanol. The reaction mixture is stirred at a temperature in the region of 20° C. for 18 hours and is then concentrated to dryness under reduced pressure (2 kPa) at a temperature in the region of 40° C. The residue is taken up in a mixture of 10 cm³ of water and 30 cm³ of diethyl ether and is then stirred at a temperature in the region of 0° C. for 15 minutes. The precipitate obtained is filtered off, washed with twice 10 cm³ of ice-cold water and then dried in a desiccator under reduced pressure (2 kPa) at a temperature in the region of 20° C. 1.2 g of N-[(2-benzyl-3-oxo-2,3-dihydro-1H-isoindol-1-yl)acetyl]guanidine are thus obtained in the form of a white powder melting at 222–225° C. Infrared spectrum (KBr) 3488; 3410; 3344; 1662; 1621; 1521; 1382 and 704 cm$^{-1}$.

b) Ethyl (2-benzyl-3-oxo-2,3-dihydro-1H-isoindol-1-yl)acetate

Ethyl (2-benzyl-3-oxo-2,3-dihydro-1H-isoindol-1-yl) acetate is prepared as described in Example 2, starting with 3.2 9 of 60% sodium hydride in 200 cm³ of 1,2-dimethoxyethane, 16.4 cm³ of triethyl phosphonoacetate and 9.5 g of 3-hydroxy-2benzyl-2,3-dihydroisoindol-1-one. The mixture is refluxed for 18 hours and is then cooled to a temperature in the region of 20° C. The reaction mixture is treated with 100 cm³ of water and then with 100 cm³ of ethyl acetate. After separation of the phases by settling, the aqueous phase is extracted twice with 100 cm³ of ethyl acetate. The organic extracts are combined, washed with 50 cm³ of brine, dried over magnesium sulfate, filtered and then concentrated to dryness under reduced pressure (2 kPa) at a temperature in the region of 40° C. The residue is purified by chromatography under argon pressure (60 kPa) on a column of silica gel (particle size 15–40 μm), eluting with successive mixtures of cyclohexane/ethyl acetate (75/25 and then 67/33 by volume). The fractions comprising the expected product are combined and concentrated to dryness under reduced pressure (2 kPa) at a temperature in the region of 40° C. 8.7 g of ethyl (2-benzyl-3-oxo-2,3-dihydro-1H-isoindol-1-yl)acetate are thus obtained in the form of a viscous yellow oil. (Rf=0.35, thin layer chromatography on silica gel, eluent: cyclohexane/ethyl acetate (75/25 by volume)).

c) 3-Hydroxy-2-benzyl-2,3-dihydroisoindol-1-one

3-Hydroxy-2-benzyl-2,3-dihydroisoindol-1-one is prepared as described in Example 1, starting with 10.2 g of N-benzylphthalimide in 100 cm³ of methanol and 2.6 g of potassium borohydride. The reaction mixture is stirred at a temperature in the region of 20° C. for 20 hours and is then cooled to a temperature in the region of 0° C. and 50 cm³ of distilled water are added dropwise. The methanol is then partially evaporated off under reduced pressure (2 kPa) at a temperature in the region of 40° C., followed by addition of a further 50 cm³ of distilled water. The aqueous phase is extracted 3 times with 50 cm³ of ethyl acetate. The organic extracts are combined, washed with 50 cm³ of brine, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 9.5 g of 3-hydroxy-2-benzyl-2,3-dihydroisoindol-1-one are thus obtained in the form of a white powder. (Rf=0.20, thin layer chromatography on silica gel, eluent: cyclohexane/ethyl acetate (75/25 by volume)).

d) N-Benzylphthalimide

N-Benzylphthalimide is prepared as described in Example 2, starting with 10 g of phthalic anhydride, 7.3 cm³ of benzylamine and a catalytic amount of paratoluenesulfonic acid in 100 cm³ of toluene. The reaction mixture is heated at a temperature in the region of 140° C. for 3 hours and is then cooled to a temperature in the region of 20° C. The reaction mixture is taken up in 100 cm³ of saturated aqueous sodium bicarbonate solution and the aqueous phase is extracted twice with 100 cm³ of ethyl acetate. The organic extracts are combined, washed with 50 cm³ of brine, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 10.3 g of N-benzylphthalimide are thus obtained in the form of a white powder. (Rf=0.44, thin layer chromatography on silica gel, eluent: cyclohexane/ethyl acetate (75/25 by volume)).

EXAMPLE 10 a) N-[2-(6-tert-Butyl-2-isobutyl-3-oxo-2,3-dihydro-1H-isoindol-1-yl)acetyl]guanidine

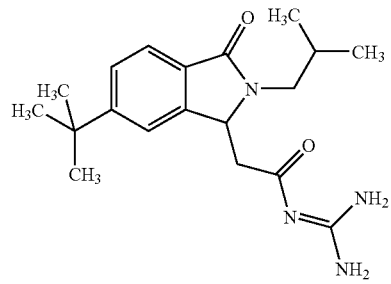

N-[(6-tert-Butyl-2-isobutyl-3-oxo-2,3-dihydro-1H-isoindol-1-yl)acetyl]guanidine is prepared as described in Example 9, starting with 20 cm³ of absolute ethanol, 0.37 g of sodium, 1.56 g of guanidinium chloride and 3.53 g of ethyl (6-tert-butyl-2-isobutyl-3oxo-2,3-dihydro-1H-isoindol-1-yl)acetate in 10 cm³ of absolute ethanol. The reaction mixture is stirred at a temperature in the region of 20° C. for 16 hours and is then concentrated to dryness under reduced pressure (2 kPa) at a temperature in the region of 40° C. The residue is taken up in a mixture of 15 cm³ of water and 45 cm³ of diethyl ether and then stirred at a temperature in the region of 0° C. for 2 hours. The precipitate obtained is filtered off, washed with twice 10 cm³ of ice-cold water and then dried in a desiccator under reduced pressure (2 kPa) at a temperature in the region of 20° C. 2.5 g of N-[(6-tert-butyl-2-isobutyl-3-oxo-2,3-dihydro-1H-isoindol-1-yl)acetyl]guanidine are thus obtained in the form of a brown powder melting at 214–215° C. Mass spectrum: DCI: m/e 345 (M+H)⁺.

b) Ethyl (5-tert-butyl-2-isobutyl-3-oxo-2,3-dihydro-1H-isoindol-1-yl)acetate and ethyl (6-tert-butyl-2-isobutyl-3-oxo-2,3-dihydro-1H-isoindol-1-yl)acetate Ethyl (5-tert-butyl-2-isobutyl-3-oxo-2,3-dihydro-1H-isoindol-1-yl)acetate and ethyl (6-tert-butyl-2-isobutyl-3-oxo-2,3-dihydro-1H-isoindol-1-yl)acetate are prepared as described in Example 2, starting with 2.9 g of 60% sodium hydride in 200 cm³ of 1,2-dimethoxyethane, 15.2 cm³ of triethyl phosphonoacetate and 9.6 g of a mixture of 5-tert-butyl-3-hydroxy-2-isobutyl-2,3-dihydroisoindol-1-one and 6-tert-butyl-3-hydoxy-2-isobutyl-2,3-dihydroisoindol-1-one. The mixture is refluxed for 18 hours and then cooled to a temperature in the region of 20° C. The reaction mixture is treated with 110 cm³ of water and then 100 cm³ of ethyl acetate. After separation of the phases by settling, the aqueous phase is extracted twice with 100 cm³ of ethyl acetate. The organic extracts are combined, washed with 100 cm³ of brine, dried over magnesium sulfate, filtered and then concentrated to dryness under reduced pressure (2 kPa) at a temperature in the region of 40° C. The residue is separated out by HPLC chromatography on a 10 μm WHELK-01SS chiral column, eluting successively with heptane/isopropanol mixtures (90/10 and then 50/50 by volume). The fractions comprising the first regioisomer are combined and concentrated under reduced pressure (1 kPa) at a temperature in the region of 40° C. The residue is dried under reduced pressure (3 kPa) at a temperature in the region of 40° C. 1.81 g of ethyl (5-tert-butyl-2-isobutyl-3-oxo-2,3-dihydro-1H-isoindol-1-yl)acetate are thus obtained in the form of a viscous gray oil (Rf=0.43, thin layer chromatography on silica gel, eluent: cyclohexane/ethyl acetate (75/25 by volume)). The fractions comprising the second regioisomer are combined and concentrated under reduced pressure (1 kPa) at a temperature in the region of 40° C. The residue is dried under reduced pressure (3 kPa) at a temperature in the region of 40° C. 3.53 g of ethyl (6-tert-butyl-2-isobutyl-3-oxo-2,3-dihydro-1H-isoindol-1-yl)acetate are thus obtained in the form of a viscous gray oil. (Rf=0.38, thin layer chromatography on silica gel, eluent: cyclohexane/ethyl acetate (75/25 by volume)).

c) 5-tert-Butyl-3-hydroxy-2-isobutyl-2,3-dihydroisoindol-1-one and 6-tert-butyl-3-hydroxy-2-isobutyl-2,3-dihydroisoindol-1-one 5-tert-Butyl-3-hydroxy-2-isobutyl-2,3-dihydroisoindol-1-one and 6-tert-butyl-3-hydroxy-2-isobutyl-2,3-dihydroisoindol-1-one are prepared as described in Example 1, starting with 10.4 g of 4-tert-butyl-N-isobutylphthalimide in 60 cm³ of methanol and 2.3 g of potassium borohydride. The reaction mixture is stirred at a temperature in the region of 20° C. for 19 hours and is then cooled to a temperature in the region of 0° C. and 50 cm³ of distilled water are added dropwise. The methanol is then partially evaporated off under reduced pressure (2 kPa) at a temperature in the region of 40° C., followed by addition of a further 50 cm³ of distilled water. The aqueous phase is extracted twice with 100 cm³ of ethyl acetate. The organic extracts are combined, washed with 50 cm³ of brine, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 9.9 g of a mixture of 5-tert-Butyl-3-hydroxy-2-isobutyl-2,3-dihydroisoindol-1-one and 6-tert-butyl-3-hydroxy-2-isobutyl-2,3-dihydroisoindol-1-one are thus obtained in the form of a yellow foam (Rf=0.26 and 0.30 unassigned, thin layer chromatography on silica gel, eluent: cyclohexane/ethyl acetate (75/25 by volume)).

d) 4-tert-Butyl-N-isobutylphthalimide 4-tert-Butyl-N-isobutylphthalimide is prepared as described in Example 2, starting with 10 g of 4-tert-butylphthalic anhydride and 4.9 cm³ of isobutylamine in 100 cm³ of toluene. The reaction mixture is heated at a temperature in the region of 75° C. for 10 minutes, followed by addition of a catalytic amount of para-toluenesulfonic acid and the mixture is heated at a temperature in the region of 140° C. for 3 hours. After cooling to a temperature in the region of 60° C., the reaction mixture is concentrated to dryness under reduced pressure (2 kPa). The residue is taken up in a mixture of 50 cm³ of water and 30 cm³ of saturated aqueous sodium bicarbonate solution and the aqueous phase is extracted twice with 200 cm³ of dichloromethane. The organic extracts are combined, washed with 50 cm³ of brine, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 10.4 g of 4-tert-butyl-N-isobutylphthalimide are thus obtained in the form of a viscous yellow oil. (Rf=0.75, thin layer chromatography on silica gel, eluent: cyclohexane/ethyl acetate (75/25 by volume)).

EXAMPLE 11

N-[2-(5-tert-Butyl-2-isobutyl-3-oxo-2,3-dihydro-1H-isoindol-1-yl)acetyl]guanidine

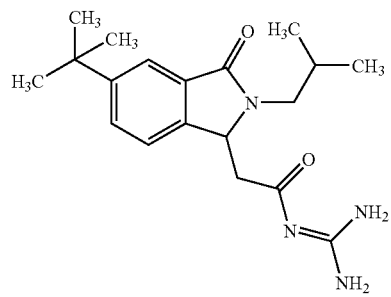

N-[(5-tert-Butyl-2-isobutyl-3-oxo-2,3-dihydro-1H-isoindol-1-yl)acetyl]guanidine is prepared as described in Example 9, starting with 10 cm³ of absolute ethanol, 0.19 g of sodium, 0.80 g of guanidinium chloride and 1.81 g of ethyl (5-tert-butyl-2-isobutyl-3-oxo-2,3-dihydro-1H-isoindol-1-yl)acetate in 10 cm³ of absolute ethanol. The reaction mixture is stirred at a temperature in the region of 20° C. for 18 hours and is then concentrated to dryness under reduced pressure (2 kPa) at a temperature in the region of 40° C. The residue is taken up in a mixture of 10 cm³ of water and 30 cm³ of diethyl ether and then stirred at a temperature in the region of 0° C. for 1 hour. The precipitate obtained is filtered off, washed with twice 10 cm³ of ice-cold water and then dried in a desiccator under reduced pressure (2 kPa) at a temperature in the region of 20° C. 1.1 g of N-[(5-tert-butyl-2-isobutyl-3-oxo-2,3-dihydro-1H-isoindol-1-yl)acetyl]guanidine are thus obtained in the form of a white powder melting at 262–263° C. Ethyl (5-tert-butyl-2-isobutyl-3-oxo-2,3-dihydro-1H-isoindol-1-yl)acetate is described in Example 10. (Analysis: C19 H28 N4 O2; % calculated C: 66.25, H: 8.19, N: 16.27, O: 9.29% found C: 66.13, H: 8.50, N: 16.12).

EXAMPLE 12 a) N-[2-(5-Chloro-2-isobutyl-3-oxo-2,3-dihydro-1H-isoindol-1-yl)acetyl]guanidine and N-[(6-Chloro-2-isobutyl-3-oxo-2,3-dihydro-1H-isoindol-1-yl)acetyl] guanidine

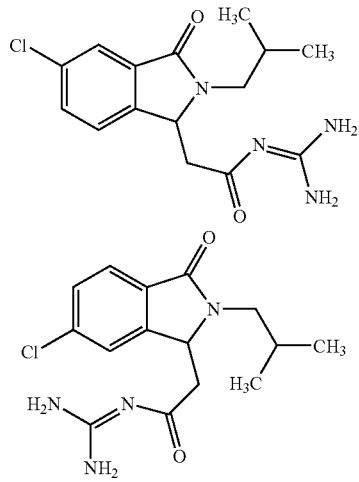

N-[(5-Chloro-2-isobutyl-3-oxo-2,3-dihydro-1H-isoindol-1-yl)acetyl]guanidine and N-[(6chloro-2-isobutyl-3-oxo-2,3-dihydro-1H-isoindol-1-yl)acetyl]guanidine are prepared as described in Example 9, starting with 20 cm³ of absolute ethanol, 0.35 g of sodium, 1.46 g of guanidinium chloride and 3.1 g of ethyl (5-chloro-2-isobutyl-3-oxo-2,3dihydro-1-H-isoindol-1-yl)acetate and ethyl (6-chloro-2-isobutyl-3-oxo-2,3-dihydro-1isoindol-1-yl)acetate in 15 cm³ of absolute ethanol. The reaction mixture is stirred at a temperature in the region of 20° C. for 18 hours and is then concentrated to dryness under reduced pressure (2 kPa) at a temperature in the region of 40° C. The residue is taken up in a mixture of 15 cm³ of water and 45 cm³ of diethyl ether and then stirred at a temperature in the region of 0° C. for 4 hours. The precipitate obtained is filtered off, washed with twice 20 cm³ of ice-cold water and then dried in a desiccator under reduced pressure (2 kPa) at a temperature in the region of 20° C. 1 g of N-[(5-chloro-2isobutyl-3-oxo-2,3-dihydro-1H-isoindol-1-yl)acetyl]quanidine and N-[(6-chloro-2-isobutyl-3-oxo-2,3-dibydro-1H-isoindol-1-yl)acetyl]guanidine is thus obtained in the form of a white powder. (Analysis: C15 H19 Cl N4 O2, % calculated C: 55.81, H: 5.93, Cl: 10.98, N: 17.36, O: 9.91% found C: 55.67, H: 6.18, Cl: 11.32, N: 17.05). Mass spectrum: DCI: m/e 323 (M+H)⁺.

b) Ethyl (5-chloro-2-isobutyl-3-oxo-2,3-dihydro-1H-isoindol-1-yl)acetate and ethyl (6-chloro-2-isobutyl-3-oxo-2,3-dihydro-1H-isoindol-1-yl)acetate Ethyl (5-chloro-2-isobutyl-3-oxo-2,3-dihydro-1H-isoindol-1-yl)acetate and ethyl (6-chloro-2-isobutyl-3-oxo-2,3-dihydro-1H-isoindol-1-yl)acetate are prepared as described in Example 2, starting with 4 g of 60% sodium hydride in 200 cm³ of 1,2-dimethoxyethane, 20.3 cm³ of triethyl phosphonoacetate and 12 g of 5-chloro-3-hydroxy-2-isobutyl-2,3-dihydroisoindol-1-one and 6-chloro-3-hydroxy-2-isobutyl-2,3-dihydroisoindol-1-one. The mixture is refluxed for 18 hours and is then cooled to a temperature in the region of 20° C. The reaction mixture is treated with 200 cm³ of water and then with 100 cm³ of ethyl acetate. After separation of the phases by settling, the aqueous phase is extracted twice with 200 cm³ of ethyl acetate. The organic extracts are combined, washed with 100 cm³ of brine, dried over magnesium sulfate, filtered and then concentrated to dryness under reduced pressure (2 kPa) at a temperature in the region of 40° C. The residue is purified-by chromatography under argon pressure (60 kPa) on a cartridge of silica gel (particle size 32–63 μm), eluting with successive mixtures of cyclohexane/ethyl acetate (90/10 and then 80/20 by volume). The fractions comprising the expected product are combined and concentrated to dryness under reduced pressure (2 kPa) at a temperature in the region of 40° C. 3.1 g of ethyl (5-chloro-2-isobutyl-3-oxo-2,3-dihydro-1-isoindol-1-yl)acetate and ethyl (6-chloro-2-isobutyl-3-oxo-2,3-dihydro-1H-isoindol-1-yl)acetate are thus obtained in the form of a viscous yellow oil. (Rf=0.34, thin layer chromatography on silica gel, eluent: cyclohexanefethyl acetate (75/25 by volume)).

c) 5-Chloro-3-hydroxy-2-isobutyl-2,3-dihydroisoindol-1-one and 6-chloro-3-hydroxy-2isobutyl-2,3-dihydroisoindol-1-one 5-Chloro-3-hydroxy-2-isobutyl-2,3-dihydroisoindol-1-one and 6-chloro-3-hydroxy-2isobutyl-2,3-dihydroinsoindol-1-one are prepared as described in Example 1, starting with 12 g of 4-chloro-N-isobutylphthalimide in 100 cm³ of methanol and 3 g of potassium borohydride. The reaction mixture is stirred at a temperature in the region of 20° C. for 20 hours and is then cooled to a temperature in the region of 0° C. and 100 cm³ of distilled water are added dropwise. The methanol is then partially evaporated off under reduced pressure (2 kPa) at a temperature in the region of 40° C. The aqueous phase is extracted twice with 150 cm³ of ethyl acetate. The organic extracts are combined, washed with 50 cm³ of brine, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 12 g of 5-chloro-3-hydroxy-2-isobutyl-2,3-dihydroinsoindol-1-one and 6-chloro-3-hydroxy-2-isobutyl-2,3-dihydroisoindol-1-one are thus obtained in the form of a white powder. (Rf=0.15, thin layer chromatography on silica gel, eluent: cyclohexane/ethyl acetate (75/25 by volume)).

d) 4-Chloro-N-isobutylphthalimide

4-Chloro-N-isobutylphthalimide is prepared as described in Example 2, starting with 10 g of 4-chlorophthalic anhydride, 5.4 cm³ of isobutylamine and a catalytic amount of para-toluenesulfonic acid in 100 cm³ of toluene. The reaction mixture is heated at a temperature in the region of 140° C. for 16 hours and is then cooled to a temperature in the region of 20° C. The reaction mixture is taken up in 100 cm³ of saturated aqueous sodium bicarbonate solution and the aqueous phase is extracted twice with 100 cm³ of ethyl acetate. The organic extracts are combined, washed with 50 cm³ of brine, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 12 g of 4-chloro-N-isobutylphthalimide are thus obtained in the form of a white powder. (Rf=0.85, thin layer chromatography on silica gel, eluent: cyclohexane/ethyl acetate (75/25 by volume)).

EXAMPLE 13 a) N-[2-(5-Bromo-2-isobutyl-3-oxo-2,3-dihydro-1H-isoindol-1-yl)acetyl]guanidine and N-[(6-Bromo-2-isobutyl-3-oxo-2,3-dihydro-1H-isoindol-1-yl)acetyl]guanidine

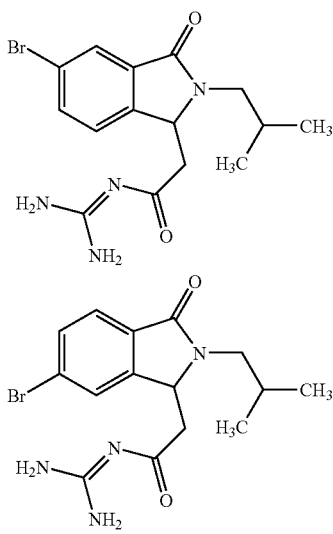

N-[(5-Bromo-2-isobutyl-3-oxo-2,3-dihydro-1H-isoindol-1-yl)acetyl]guanidine and N-[(6-bromo-2-isobutyl-3-oxo-2,3-dihydro-1H-isoindol-1-yl)acetyl]guanidine are prepared as described in Example 9, starting with 30 cm³ of absolute ethanol, 0.36 g of sodium, 1.5 g of guanidinium chloride and 3.7 g of ethyl (5-bromo-2-isobutyl-3-oxo-2,3-dihydro-1H-isoindol-1-yl)acetate and ethyl (6-bromo-2-isobutyl-3-oxo-2,3-dihydro-1H-isoindol1-yl)acetate in 20 cm³ of absolute ethanol. The reaction mixture is stirred at a temperature in the region of 20° C. for 16 hours and is then concentrated to dryness under reduced pressure (2 kPa) at a temperature in the region of 40° C. The residue is taken up in a mixture of 100 cm³ of water and 200 cm³ of ethyl acetate. The organic phase is washed with 100 cm³ of water and then with 150 cm³ of saturated sodium chloride solution. This organic phase is dried over magnesium sulfate and concentrated under reduced pressure (2 kPa) at a temperature in the region of 40° C. A white solid is thus obtained, which is then taken up again and stirred in a mixture of 15 cm³ of water and 50 cm³ of diethyl ether for 1.5 hours at a temperature in the region of 20° C. The white solid thus obtained is filtered off, washed with twice 50 cm³ of diethyl ether and dried in a desiccator under reduced pressure (2 Pa) at a temperature in the region of 35° C. 0.92 g of N-[(5-bromo-2-isobutyl-3-oxo-2,3-dihydro-1H-isoindol-1-yl)acetyl]guanidine and N-[(6-bromo-2-isobutyl-3-oxo-2,3-dihydro-1H-isoindol-1-yl)acetyl]quanidine are thus obtained in the form of a white powder. (Analysis: C15 H19 Br N4 O2, % calculated C: 49.06, H: 5.21, Br: 21.76, N: 15.26, O: 8.71% found C: 48.97, H: 5.34, Cl: 14.72, N: 21.52). Mass spectrum:. El: m/e 366 (M$^+$), m/e 279, m/e 86 (base peak).

b) Ethyl (5-bromo-2-isobutyl-3-oxo-2,3-dihydro-1H-isoindol-1-yl)acetate and ethyl (6-bromo-2-isobutyl-3-oxo-2,3-dihydro-1H-isoindol-1-yl)acetate Ethyl (5-bromo-2-isobutyl-3-oxo-2,3-dihydro-1H-isoindol-1-yl)acetate and ethyl (6-bromo-2-isobutyl-3-oxo-2,3-dihydro-1H-isoindol-1-yl)acetate are prepared as described in Example 2, starting with 5.0 g of 60% sodium hydride in 250 cm³ of 1,2-dimethoxyethane, 24.8 cm³ of triethyl phosphonoacetate and 23.7 g of 5-bromo-3-hydroxy-2-isobutyl-2,3-dihydroisoindol-1-one and 6-bromo-3-hydroxy-2-isobutyl-2,3-dihydroisoindol-1-one. The mixture is refluxed for 4 hours and then cooled to a temperature in the region of 20° C. The reaction mixture is treated with 300 cm³ of water and the mixture is then extracted with 3 times 250 cm³ of diethyl ether. The organic extracts are combined, washed with 300 cm³ of saturated brine, dried over magnesium sulfate, filtered and then concentrated to dryness under reduced pressure (2 kPa) at a temperature in the region of 40° C. The residue is purified by chromatography under argon pressure (80 kPa), on a column of silica gel (particle size 32–63 μm), eluting with successive mixtures of cyclohexane/ethyl acetate (95/5 by volume), cyclohexane/methanol (90/10) and cyclohexane/ethyl acetate (80/20). The fractions comprising the expected product are combined and concentrated to dryness under reduced pressure (2 kPa) at a temperature in the region of 40° C. 3.72 g of ethyl (5-bromo-2-isobutyl-3-oxo-2,3-dihydro-1H-isoindol-1-yl)acetate and ethyl (6-bromo-2-isobutyl-3-oxo-2,3-dihydro-1H-isoindol-1-yl)acetate are thus obtained in the form of a colorless oil. (Rf=0.70, thin layer chromatography on silica gel, eluent: cyclohexane/ethyl acetate (50/50 by volume)).

c) 5-Bromo-3-hydroxy-2-isobutyl-2,3-dihydroisoindol-1-one and 6-bromo-3-hydroxy-2-isobutyl-2,3-dihydroisoindol-1-one 5-Bromo-3-hydroxy-2-isobutyl-2,3-dihydroisoindol-1-one and 6-bromo-3-hydroxy-2-isobutyl-2,3-dihydroinsoindol-1-one are prepared as described in Example 1, starting with 23.6 g of 4-bromo-N-isobutylphthalimide in 200 cm³ of methanol and 4.5 g of potassium borohydride. The reaction mixture is stirred at a temperature in the region of 20° C. for 16 hours and is then cooled to a temperature in the region of 0° C. and 175 cm³ of distilled water are added dropwise. The methanol is then partially evaporated off under reduced pressure (2 kPa) at a temperature in the region of 40° C. The aqueous phase is extracted 3 times with 200 cm³ of ethyl acetate. The organic extracts are combined, dried over magnesium sulfate, filtered and then concentrated to dryness under reduced pressure (2 kPa) at a temperature in the region of 40° C. 23.7 g of 5-bromo-3-hydroxy-2-isobutyl-2,3-dihydroisoindol-1-one and 6-bromo-3-hydroxy-2-isobutyl-2,3-dihydroisoindol-1-one are thus obtained in the form of a white powder (Rf=0.79, thin layer chromatography on silica gel, eluent: cyclohexane/ethyl acetate (50/50 by volume)).

d) 4-Bromo-N-isobutylphthalimide

4-Bromo-N-isobutylphthalimide is prepared as described in Example 2, starting with 20 g of 4-bromophthalic anhydride, 9.2 cm³ of isobutylamine and a catalytic amount of para-toluenesulfonic acid in 200 cm³ of toluene. The reaction mixture is heated at a temperature in the region of 140° C. for 6 hours and is then cooled to a temperature in the region of 20° C. The reaction mixture is concentrated to dryness under reduced pressure (2 kPa) at a temperature in the region of 40° C., and the residue is then taken up in 350 cm³ of ethyl acetate and 300 cm³ of saturated sodium hydrogen carbonate solution. The aqueous phase is separated out after settling has taken place and then extracted twice with 350 cm³ of ethyl acetate. The combined organic extracts are washed with 300 cm³ of saturated brine, dried over magnesium sulfate, filtered and then concentrated to dryness under reduced pressure (2 kPa) at a temperature in the region of 40° C. 23.6 g of 4-bromo-N-isobutylphthalimide are thus obtained in the form of a white powder (Rf=0.91, thin layer chromatography on silica gel, eluent: cyclohexane/ethyl acetate (50/50 by volume)).

EXAMPLE 14

N-[2-(2-Isobutyl-3-oxo-5-trifluoromethyl-2,3-dihydro-1H-isoindol-1-yl)-acetyl]-guanidine

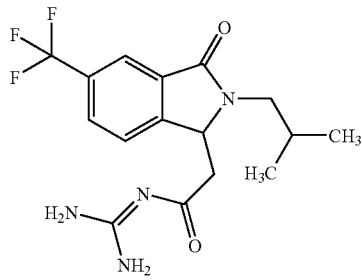

N-[2-(2-Isobutyl-3-oxo-5-trifluoromethyl-2,3-dihydro-1H-isoindol-1-yl)-acetyl]-guanidine is prepared as described in Example 9, starting with 10 cm³ of absolute ethanol, 0.19 g of sodium, 0.78 g of guanidinium chloride and 1.86 g of ethyl (5-trifluoromethyl-2-isobutyl-3-oxo-2,3-dihyrdo-1H-isoindol-1-yl)acetate in 10 cm³ of absolute ethanol. The reaction mixture is stirred at a temperature in the region of 20° C. for 16 hours and is then concentrated to dryness under reduced pressure (2 kPa) at a temperature in the region of 40° C. The residue is then taken up in a mixture of 5 cm³ of water and 15 cm³ of diethyl ether and then concentrated to dryness again under the same conditions. The residue is taken up in 100 cm³ of ethyl acetate and the organic phase is washed with twice 60 cm³ of aqueous 1N sodium hydroxide solution and then with twice 60 cm³ of 4N hydrochloric acid solution. The acidic aqueous extracts are combined, treated with aqueous 30% sodium hydroxide solution to pH 14, and then extracted with 3 times 50 cm³ of ethyl acetate. The organic extracts are combined, washed with 100 cm³ of saturated sodium chloride solution, dried over magnesium sulfate and concentrated to dryness under reduced pressure (2 kPa) at a temperature in the region of 40° C. The yellow solid thus obtained is taken up in 20 cm³ of diethyl ether, stirred at a temperature in the region of 20° C. for 1 hour and then filtered off. The solid is washed with twice 20 cm³ of diethyl ether and then dried in a desiccator under reduced pressure (2 Pa) at a temperature in the region of 35° C. 0.34 g of N-[(5-trifluoromethyl-2-isobutyl-3-oxo-2,3-dihydro-1H-isoindol-1-yl)acetyl]guanidine is thus obtained in the form of a yellow powder melting at 224° C. (Analysis: C16 H19 F3 N4 O2% calculated C: 53.93, H: 5.37, F: 15.99, N: 15.72, 0: 8.98% found C: 53.95, H: 15 5.15, F: 15.00, N: 15.59).

EXAMPLE 15 a) N-[2-(2-Isobutyl-3-oxo-6-trifluoromethyl-2,3-dihydro-1H-isoindol-1-yl)-acetyl]guanidine

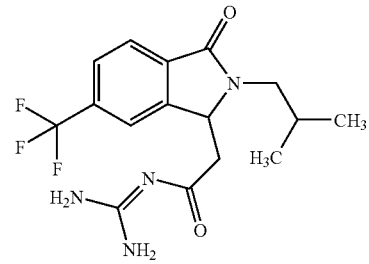

N-[2-(2-Isobutyl-3-oxo-6-trifluoromethyl-2,3-dihydro-1H-isoindol-1-yl)-acetyl]-guanidine is prepared as described in Example 9, starting with 10 cm³ of absolute ethanol, 0.13 g of sodium, 0.52 g of guanidinium chloride and 1.25 g of ethyl (6-trifluoromethyl-2-isobutyl-3-oxo-2,3-dihydro-1H-isoindol-1-yl)acetate in 10 cm3 of absolute ethanol. The reaction mixture is stirred at a temperature in the region of 20° C. for 16 hours and then concentrated to dryness under reduced pressure (2 kPa) at a temperature in the region of 40° C. The residue is then taken up in a mixture of 5 cm³ of water and 15 cm³ of diethyl ether and then concentrated to dryness again under the same conditions. The residue is taken up in 100 cm³ of ethyl acetate and the organic phase is washed with twice 50 cm³ of aqueous 1N sodium hydroxide solution and then with 30 cm³ of aqueous 4N hydrochloric acid solution. The acidic aqueous phase is treated with aqueous 30% sodium hydroxide solution to pH 14, and then extracted with 3 times 50 cm³ of ethyl acetate. The organic extracts are combined and washed with saturated sodium chloride solution, dried over magnesium sulfate and then concentrated to dryness under reduced pressure (2 kPa) at a temperature in the region of 40° C. The white solid thus obtained is taken up in 20 cm³ of diethyl ether-and stirred at a temperature in the region of 20° C., and then filtered. The solid is dried in a desiccator under reduced pressure (2 kPa) at a temperature in the region of 20° C. 0.099 g of N-[2-(2-Isobutyl-3-oxo-6-trifluoromethyl-2,3-dihydro-1H-isoindol-1-yl)-acetyl]-guanidine is thus obtained in the form of a pale yellow solid melting at 154° C. Mass spectrum: EI: m/e 356 (M⁺), m/e 269, m/e 200, m/e 86 (base peak).

b) Ethyl (5-trifluoromethyl-2-isobutyl-3-oxo-2,3-dihydro-1H-isoindol-1-yl)acetate and ethyl (6-trifluoromethyl-2-isobutyl-3-oxo-2,3-dihydro-1H-isoindol-1-yl)acetate Ethyl (5-trifluoromethyl-2-isobutyl-3-oxo-2,3-dihydro-1H-isoindol-1-yl)acetate and ethyl (6-trifluoromethyl-2-isobutyl-3-oxo-2,3-dihydro-1H-isoindol-1-yl)acetate are prepared as described in Example 2, starting with 1.32 g of 60% sodium hydride in 120 cm³ of 1,2-dimethoxyethane, 6.57 cm³ of triethyl phosphonoacetate and 12.07 g of 5-trifluoromethyl-3-hydroxy-2-isobutyl-2,3-dihydroisoindol-1-one and 6-trifluoromethyl-3-hydroxy-2-isobutyl-2,3-dihydroisoindol-1-one. The mixture is refluxed for 24 hours and then cooled to a temperature in the region of 20° C. The reaction mixture is then treated with 150 cm³ of water and the mixture is then extracted with 3 times 250 cm³ of diethyl ether. The organic extracts are combined, washed with 150 cm³ of saturated brine, dried over magnesium sulfate, filtered and then concentrated to dryness under reduced pressure (2 kPa) at a temperature in the region of 40° C. A mixture of 2.3 g of the residue is injected onto a column 8 cm in diameter containing 1.2 kg of Whelk OI,SS chiral stationary phase. The elution is performed with a mobile phase composed of a mixture of dichloromethane, ethanol and heptane in proportions of 14.5/0.5/85 v/v. Two additional injections of 2.7 g and 3 g are made under identical conditions. The fractions comprising the first regioisomer are combined and concentrated to dryness under reduced pressure (1 kPa) at a temperature in the region of 40° C. 1.86 g of ethyl (5-trifluoromethyl-2-isobutyl-3-oxo-2,3-dihydro-1H-isoindol-1-yl)acetate are thus obtained in the form of a white solid (Rf=0.64, thin layer chromatography on silica gel, eluent: cyclohexane/ethyl acetate (50/50 by volume)). The fractions comprising the second regioisomer are combined and concentrated to dryness under reduced pressure (1 kPa) at a temperature in the region of 40° C. to give 2.79 g of a white solid. This product is repurified by chromatography under argon pressure (80 kPa) on a cartridge of silica gel (particle size 32–63 μm), eluting with a mixture of cyclohexane/ethyl acetate (90/10 by volume). The fractions comprising the expected product are combined and concentrated to dryness under reduced pressure (2 kPa) at a temperature in the region of 40° C. 1.25 g of ethyl (6-trifluoromethyl-2-isobutyl-3-oxo-2,3-dihydro-1H-isoindol-1-yl)acetate are thus obtained in the form of a colorless viscous oil. (Rf=0.46, thin layer chromatography on silica gel, eluent: cyclohexane/ethyl acetate (75/25 by volume)).

c) 5-Trifluoromethyl-3-hydroxy-2-isobutyl-2,3-dihydroisoindol-1-one and 6-trifluoromethyl-3-hydroxy-2-isobutyl-2,3-dihydroisoindol-1-one 5-Trifluoromethyl-3-hydroxy-2-isobutyl-2,3-dihydroisoindol-1-one and 6-trifluoromethyl-3-hydroxy-2-isobutyl-2,3-dihydroisoindol-1-one are prepared as described in Example 1, starting with 14.9 g of 4-trifluoromethyl-N-isobutylphthalimide in 300 cm³ of methanol and 2.96 g of potassium borohydride. The reaction mixture is stirred at a temperature in the region of 20° C. for 16 hours and then cooled to a temperature in the region of 0° C. and 100 cm³ of distilled water are added dropwise. The methanol is then partially evaporated off under reduced pressure (2 kPa) at a temperature in the region of 40° C. The aqueous phase is extracted 3 times with 200 cm³ of ethyl acetate. The organic extracts are combined, washed with 300 cm³ of saturated sodium chloride solution, dried over magnesium sulfate, filtered and then concentrated to dryness under reduced pressure (2 kPa) at a temperature in the region of 40° C. 12.07 g of 5-trifluoromethyl-3-hydroxy-2-isobutyl-2,3-dihydroisoindol-1-one and 6-trifluoromethyl-3-hydroxy-2-isobutyl-2,3-dihydroisoindol-1-one are thus obtained in the form of a white powder. (Rf=0.64, thin layer chromatography on silica gel, eluent: cyclohexane/ethyl acetate (50/50 by volume)).

d) 4-Trifluoromethyl-N-isobutylphthalimide

4-Trifluoromethyl-N-isobutylphthalimide is prepared as described in Example 2, starting with 14.8 g of 4-trifluoromethylphthalic anhydride, 7.2 cm³ of isobutylamine and a catalytic amount of para-toluenesulfonic acid in 160 cm³ of toluene. The reaction mixture is heated at a temperature in the region of 140° C. for 5 hours and is then cooled to a temperature in the region of 20° C. The reaction mixture is concentrated to dryness under reduced pressure (2 kPa) at a temperature in the region of 40° C. and the residue is taken up in 250 cm³ of ethyl acetate and 200 cm³ of saturated aqueous sodium hydrogen carbonate solution. The aqueous phase is separated out after settling has taken place and then extracted twice with 250 cm³ of ethyl acetate. The organic extracts are combined, washed with saturated brine, dried over magnesium sulfate, filtered and then concentrated to dryness under reduced pressure (2 kPa) at a temperature in the region of 40° C. 14.9 g of 4-trifluoromethyl-N-isobutylphthalimide are thus obtained in the form of a yellow powder (Rf=0.59, thin layer chromatography on silica gel, eluent: cyclohexane/ethyl acetate (75/25 by volume)).

4-Trifluoromethylphthalic anhydride can be prepared by adaptation or application of the method described by Cavalleri et al., J. Med. Chem., 13(1), 148–149, (1970).

EXAMPLE 16 a) N-[2-(2-Isobutyl-5-isopropoxy-3-oxo-2,3-dihydro-1H-isoindol-1-yl)-acetyl]-guanidine

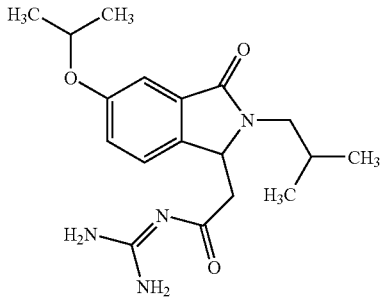

N-[2-(2-Isobutyl-5-isopropoxy-3-oxo-2,3-dihydro-1H-isoindol-1-yl)-acetyl]-guanidine is prepared as described in Example 9, starting with 20 cm³ of absolute ethanol, 0.086 g of sodium, 0.36 g of guanidinium chloride and 0.42 g of ethyl (5-isopropyloxy-2-isobutyl-3-oxo-2,3-dihydro-1H-isoindol-1-yl)acetate. The reaction mixture is stirred at a temperature in the region of 20° C. for 18 hours and then concentrated to dryness under reduced pressure (2 kPa) at a temperature in the region of 40° C. The residue is then taken up in 50 cm³ of ethyl acetate and the organic phase is washed twice with 30 cm³ of aqueous 1 N sodium hydroxide solution and then twice with 50 cm³ of aqueous 1N hydrochloric acid solution. The acidic aqueous phase is treated with aqueous 30% sodium hydroxide solution to pH 14, and then extracted with 3 times 30 cm³ of ethyl acetate. The organic extracts are combined, washed with 50 cm³ of saturated brine, dried over magnesium sulfate and concentrated under reduced pressure (2 kPa) at a temperature in the region of 40° C. The residue is triturated with diethyl ether and then filtered and dried in a desiccator under reduced pressure (2 Pa) at a temperature in the region of 40° C. for 2 hours. 0.0175 g of N-[2-(2-Isobutyl-5-isopropoxy-3-oxo-2,3-dihydro-1H-isoindol-1-yl)-acetyl]-guanidine is thus obtained in the form of a white powder melting at 208° C. $^1$H NMR (300 MHz, d6-$(CD_3)_2SO$, δ in ppm): 0.75 (d, J=6.5 Hz: 3H); 0.90 (d, J=6.5 Hz: 3H); 1.30 (mt: 6H); 2.01 (mt: 1H); 2.40 (dd, J=15 and 6.5 Hz: 1H); 2.65 (dd, J=15 and 6.5 Hz: 1H); 3.00 (dd, J=13.5 and 5.5 Hz: 1H); 3.53 (dd, J=13.5 and 10 Hz: 1H) 4.68 (mt: 1H); 4.96 (broad t, J=6.5 Hz: 1H); from 6.40 to 7.10 (broad multiplet: 2H); 6.98 (dd, J=8.5 and 2 Hz: 1H); 7.09 (d, J=2 Hz: 1H); 7.54 (d, J=8.5 Hz: 1H); from 7.60 to 8.20 (broad multiplet: 2H).

b) Ethyl (5-isopropyloxy-2-isobutyl-3-oxo-2,3-dihydro-1H-isoindol-1-yl)acetate Ethyl (5-isopropyloxy-2-isobutyl-3-oxo-2,3-dihydro-1H-isoindol-1-yl)acetate is prepared as described in Example 2, starting with 0.149 g of 60% sodium hydride in 20 cm³ of 1,2-dimethoxyethane, 1.23 cm³ of triethyl phosphonoacetate and 1.08 g of 5-isopropyloxy-3-hydroxy-2-isobutyl-2,3-dihydro-isoindol-1-one. The mixture is refluxed for 5 hours and then cooled to a temperature in the region of 20° C. The reaction mixture is treated with 100 cm³ of water and the mixture is then extracted with 3 times 100 cm³ of diethyl ether. The organic extracts are combined, washed with 100 cm³ of saturated brine, dried over magnesium sulfate, filtered and then concentrated to dryness under reduced pressure (2 kPa) at a temperature in the region of 40° C. The residue is purified by chromatography under argon pressure (80 kPa) on a cartridge of silica gel (particle size 32–63 µm), eluting with a mixture of cyclohexane/ethyl acetate (90/10 by volume) and then with a mixture of cyclohexane/ethyl acetate (80/20 by volume). The fractions comprising the expected product are combined and concentrated to dryness under reduced pressure (2 kPa) at a temperature in the region of 40° C. 0.42 g of ethyl (5-isopropyloxy-2-isobutyl-3-oxo-2,3-dihydro-1H-isoindol-1yl)acetate is thus obtained in the form of a colorless oil. (Rf=0.57, thin layer chromatography on silica gel, eluent: cyclohexane/ethyl acetate (50/50 by volume)).

c) 5-Isopropyloxy-3-hydroxy-2-isobutyl-2,3-dihydroisoindol-1-one

5-Isopropyloxy-3-hydroxy-2-isobutyl-2,3-dihydroisoindol-1-one is prepared as described in Example 1, starting with 1.16 g of N-isobutyl-4-isopropyloxyphthalimide in 20 cm³ of methanol and 0.24 g of potassium borohydride. The reaction mixture is stirred at a temperature in the region of 20° C. for 17 hours and then cooled to a temperature in the region of 0° C. and 30 cm³ of distilled water are added dropwise. The methanol is then partially evaporated off under reduced pressure (2 kPa) at a temperature in the region of 40° C., and 50 cm³ of water are added. The aqueous phase is extracted 3 times with 70 cm³ of ethyl acetate. The organic extracts are combined, washed with 100 cm³ of saturated sodium chloride solution, dried over magnesium sulfate, filtered and then concentrated to dryness under reduced pressure (2 kPa) at a temperature in the region of 40° C. 1.08 g of 5-isopropyloxy-3-hydroxy-2-isobutyl-2,3-dihydroisoindol-1-one are thus obtained in the form of a viscous colorless oil. (Rf=0.50, thin layer chromatography on silica gel, eluent: cyclohexane/ethyl acetate (50/50 by volume)).

d) N-Isobutyl-4-isopropyloxyphthalimide

A mixture of 1 g of 4-hydroxy-N-isobutylphthalimide, 0.85 cm³ of 2-bromopropane and 1.38 g of potassium carbonate in 5 cm³ of dimethylformamide is stirred at a temperature in the region of 60° C. for 17 hours. The reaction mixture is then cooled to a temperature in the region of 20° C. and then concentrated to dryness under reduced pressure (2 kPa) at a temperature in the region of 40° c. The residue is taken up in 70 cm³ of water and then extracted 3 times with 75 cm³ of ethyl acetate. The organic phases are combined, washed with saturated sodium chloride solution, dried over magnesium sulfate, filtered and then concentrated to dryness under reduced pressure (2 kPa) at a temperature in the region of 40° C. 1.16 g of N-isobutyl-4-isopropyloxyphthalimide are thus obtained in the form of a white solid. (Rf=0.50, thin layer chromatography on silica gel, eluent: cyclohexane/ethyl acetate (75/25 by volume)).

e) 4-Hydroxy-N-isobutylphthalimide

4-Hydroxy-N-isobutylphthalimide is prepared as described in Example 2, starting with 7.26 g of 4-acetoxyphthalic anhydride, 7.35 cm³ of isobutylamine and a catalytic amount of para-toluenesulfonic acid in 75 cm³ of toluene. The reaction mixture is heated at a temperature in the region of 140° C. for 4 hours and then cooled to a temperature in the region of 40° C. and concentrated to dryness under reduced pressure (2 kPa). The residue is taken up in 175 cm³ of ethyl acetate and 150 cm³ of saturated sodium hydrogen carbonate solution. The aqueous phase is separated out after settling has taken place and then extracted twice with 150 cm³ of ethyl acetate. The organic extracts are combined, washed with 200 cm³ of saturated brine, dried over magnesium sulfate, filtered and then concentrated to dryness under reduced pressure (2 kPa) at a temperature in the region of 40° C. The residue is taken up and stirred in 100 cm³ of cyclohexane at a temperature in the region of 20° C. for 1.5 hours and then filtered. The solid is dried in a desiccator under reduced pressure (2 kPa) at a temperature in the region of 20° C. 4.0 g of 4-hydroxy-N-isobutylphthalimide are thus obtained in the form of a white solid. (Rf=0.25, thin layer chromatography on silica gel, eluent: cyclohexane/ethyl acetate (75/25 by volume)).

The 4-acetoxyphthalic anhydride can be prepared by adaptation or application of the method described by J. Sah, J. med. Chem., 42 (16), 3014–3017, (1999) and N. J. Hinde, J. Chem. Soc., Perkin Trans 2, 5,1249–125, (1998).

EXAMPLE 17 a) N-[2-(7-Fluoro-2-isobutyl-3-oxo-2,3-dihydro-1H-isoindol-1-yl)acetyl]guanidine

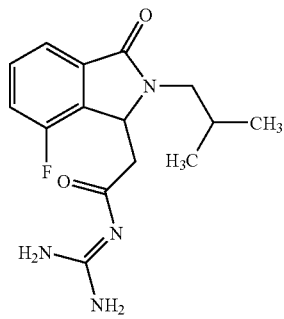

N-[(7-Fluoro-2-isobutyl-3-oxo-2,3-dihydro-1H-isoindol-1-yl)acetyl]guanidine is prepared as described in Example 1, starting with 1.29 g of potassium tert-butoxide, 1.32 g of guanidinium chloride and 0.67 g of ethyl (7-fluoro-2-isobutyl-3-oxo-2,3-dihydro-1H-isoindol-1-yl)acetate. The reaction mixture is stirred at a temperature in the region of 20° C. for 20 hours, and is then filtered. The filtrate is taken up in 40 cm³ of water and 60 cm³ of ethyl acetate. After separation of the phases by settling, the organic phase is separated out and the aqueous phase is extracted with twice 60 cm³ of ethyl acetate. The organic extracts are combined, dried over sodium sulfate, filtered and concentrated to dryness under reduced pressure (0.6 kPa) at a temperature in the region of 55° C. The evaporation residue is taken up in diethyl ether and concentrated to dryness again under the same conditions, and then taken up in water and concentrated to dryness again under the same conditions. The residue is purified by chromatography under argon pressure (50 kPa), on a column of silica gel (particle size 15–40 μm), eluting with a mixture of dichloromethane/methanol (90/10 by volume). The fractions comprising the expected product are combined and concentrated to dryness under reduced pressure (2 kPa) at a temperature in the region of 20° C. The residue is taken up in diisopropyl ether, triturated, filtered and then dried. 0.15 g of N-[(7-fluoro-2-isobutyl-3-oxo-2,3-dihydro-1H-isoindol-1-yl)acetyl]guanidine is thus obtained in the form of a pale yellow solid melting at 205° C. $^1$H NMR (300 MHz, d6-(CD$_3$)$_2$SO, δ in ppm): 0.74 (d, J=6.5 Hz: 3H); 0.89 (d, J=6.5 Hz: 3H); 2.06 (mt: 1H); 2.38 (dd, J=15 and 7.5 Hz: 1H); 2.90 (dd, J=15 and 4.5 Hz: 1H); 3.04 (dd, J=13.5 and 4.5 Hz: 1H); 3.56 (dd, J=13.5 and 10 Hz: 1H); 5.23 (dd, J=7.5 and 4.5 Hz: 1H); from 6.20 to 7.00 (broad multiplet: 2H); from 7.35 to 7.60 (mt: 3H); from 7.50 to 8.20 (broad multiplet: 2H).

b) Ethyl (7-fluoro-2-isobutyl-3-oxo-2,3-dihydro-1H-isoindol-1-yl)acetate

Ethyl (7-fluoro-2-isobutyl-3-oxo-2,3-dihydro-1H-isoindol-1-yl)acetate is prepared as described in Example 2, starting with 0.2 g of 60% sodium hydride in 15 cm$^3$ of 1,2-dimethoxyethane, 1.1 cm$^3$ of triethyl phosphonoacetate and 0.8 g of 4-fluoro-3-hydroxy-2-isobutyl-2,3-dihydroisoindol-1-one. The crude product is purified by chromatography under argon pressure (50 kPa) on a column of silica gel (particle size 40–63 μm), eluting with a mixture of cyclohexane/ethyl acetate (80/20 by volume). The fractions comprising the expected product are combined and concentrated to dryness under reduced pressure (2 kPa) at a temperature in the region of 20° C. 0.44 g of ethyl (7-fluoro-2-isobutyl-3-oxo-2,3-dihydro-1-isoindol-1-yl)acetate is thus obtained in the form of a yellow oil. (Rf=0.59, thin layer chromatography on silica gel, eluent: cyclohexane/ethyl acetate (50/50 by volume)).

c) 4-Fluoro-3-hydroxy-2-isobutyl-2,3-dihydroisoindol-1-one

4-Fluoro-3-hydroxy-2-isobutyl-2,3-dihydroisoindol-1-one is prepared as described in Example 1 starting with 3.9 g of 3-fluoro-N-isobutylphthalimide in 20 cm$^3$ of methanol and 0.95 g of potassium borohydride. The reaction mixture is stirred at a temperature in the region of 20° C. for 19 hours and is then cooled to a temperature in the region of 0° C. and distilled water is added dropwise. The precipitate obtained is filtered off, washed with cold water and then dried in a desiccator under reduced pressure (2 kPa) at a temperature in the region of 20° C. 3.5 g of 4-fluoro-3-hydroxy-2-isobutyl-2,3-dihydroisoindol-1-one are thus obtained in the form of a sticky white powder. (Rf=0.36, thin layer chromatography on silica gel, eluent: cyclohexane/ethyl acetate (60/40 by volume)).

d) 3-Fluoro-N-isobutylphthalimide

3-Fluoro-N-isobutylphthalimide is prepared as described in Example 2, starting with 3.4 g of 3-fluorophthalic anhydride, 2.0 cm$^3$ of isobutylamine and a catalytic amount of para-toluenesulfonic acid in 20 cm$^3$ of toluene. The reaction mixture is heated at a temperature in the region of 140° C. for 3 hours. After cooling to a temperature in the region of 20° C., the reaction mixture is concentrated to dryness under reduced pressure (2 kPa). The residue is taken up in dichloromethane and washed with saturated aqueous sodium bicarbonate solution. The organic phase is separated out after settling has taken place, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 4.0 g of 3-fluoro-N-isobutylphthalimide are thus obtained in the form of an off-white powder. (Rf=0.73, thin layer chromatography on silica gel, eluent: dichloromethane).

EXAMPLE 18 a) N-[2-(5,6-Dichloro-2-isobutyl-3-oxo-2,3-dihydro-1H-isoindol-1-yl)acetyl]guanidine

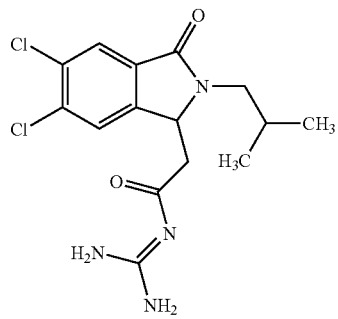

0.04 g of sodium is added to 4.0 cm$^3$ of absolute ethanol under an inert atmosphere. After the sodium has totally disappeared, 0.16 g of guanidinium chloride is added. The reaction mixture is stirred under an inert atmosphere at a temperature in the region of 20° C. for 45 minutes and is then filtered. The filtrate is concentrated to dryness under reduced pressure (2 kPa) at a temperature in the region of 40° C. The residue is diluted in 10 cm$^3$ of tetrahydrofuran, followed by addition of a solution of (5,6-dichloro-2-isobutyl-3-oxo-2,3-dihydro-1H-isoindol-1-yl)acetyl chloride prepared below in 5 cm$^3$ of tetrahydrofuran. The reaction mixture is stirred at a temperature in the region of 20° C. for 16 hours and is then concentrated to dryness under reduced pressure (2 kPa) at a temperature in the region of 40° C. The residue is taken up in 50 cm$^3$ of ethyl acetate and is then washed twice with 50 cm$^3$ of 1N hydrochloric acid solution. The aqueous extracts are combined and the pH is adjusted to 14 by adding 30% sodium hydroxide solution and the mixture is extracted 3 times with 50 cm$^3$ of ethyl acetate. The organic extracts are combined, washed with 100 cm$^3$ of saturated brine, dried over magnesium sulfate, filtered and then concentrated to dryness under reduced pressure (2 kPa) at a temperature in the region of 40° C. The residue is taken up in ethyl acetate and then concentrated to dryness again under the same conditions. The residue is taken up in 20 cm$^3$ of diethyl ether, triturated and then filtered. The solid is dried in a desiccator under reduced pressure (2 Pa) at a temperature in the region of 35° C. 0.04 g of N-[5,6-dichloro-2-isobutyl-3-oxo-2,3-dihydro-1H-isoindol-1-yl)acetyl]guanidine is thus obtained in the form of an off-white powder melting at 154° C. Mass spectrum: DCI: m/e 357 (M+H)$^+$.

b) 5,6-Dichloro-2-isobutyl-3-oxo-2,3-dihydro-1H-isoindol-1-yl)acetyl chloride 0.72 g of oxalyl chloride is added dropwise to a solution of 0.36 g of (5,6-dichloro-2-isobutyl-3-oxo-2,3-dihydro-1H-isoindol-1-yl)acetic acid in 10 cm$^3$ of dichloromethane under an inert atmosphere. The reaction mixture is stirred under an inert atmosphere at a temperature in the region of 20° C. for 3 hours and is then concentrated to dryness under reduced pressure (2 kPa) at a temperature in the region of 40° C. The crude 5,6-dichloro-2-isobutyl-3-oxo-2,3-dihydro-1H-isoindol-1-yl)acetyl chloride is thus obtained in the form of a viscous green oil, which is used directly above.

c) 5,6-Dichloro-2-isobutyl-3-oxo-2,3-dihydro-1H-isoindol-1-yl)acetic acid 0.09 g of sodium is added to 5 cm³ of absolute ethanol under an inert atmosphere. After the sodium has totally disappeared, 0.04 g of guanidinium chloride is added. The reaction mixture is stirred under an inert atmosphere at a temperature in the region of 20° C. for 1.5 hours, followed by addition of a solution of 0.93 g of ethyl (5,6-dichloro-2-isobutyl-3-oxo-2,3-dihydro-1H-isoindol-1-yl)acetate in 10 cm³ of absolute ethanol. The reaction mixture is stirred at a temperature in the region of 20° C. for 18 hours and is then concentrated to dryness under reduced pressure (2 kPa) at a temperature in the region of 40° C. The residue is taken up in a mixture of 5 cm³ of water and 15 cm³ of diethyl ether and is then stirred at a temperature in the region of 20° C. for 1 hour. The mixture is concentrated to dryness under reduced pressure (2 kPa) at a temperature in the region of 40° C. The residue is taken up in a mixture of dichloromethane and ethyl acetate and then filtered. The filtrate is purified by chromatography under argon pressure (80 kPa), on a cartridge of silica gel (particle size 32–63 µm), eluting with a mixture of dichloromethane/methanol (95/5 by volume). The fractions comprising the expected product are combined and concentrated to dryness under reduced pressure (2 kPa) at a temperature in the region of 40° C. The residue is taken up in diethyl ether, triturated and then filtered. The solid is dried in a desiccator under reduced pressure (2 Pa) at a temperature in the region of 35° C. and then redissolved in 70 cm³ of ethyl acetate and treated with 50 cm³ of aqueous 1N sodium hydroxide solution. After separation of the phases by settling, the organic phase is washed with 50 cm³ of aqueous 1N sodium hydroxide solution. The aqueous extracts are combined and then treated with aqueous 5N hydrochloric acid solution to pH 1. After extraction with 3 times 50 cm³ of ethyl acetate, the organic extracts are combined, washed with 100 cm³ of saturated brine, dried over magnesium sulfate, filtered and then concentrated to dryness under reduced pressure (2 kPa) at a temperature in the region of 40° C. 0.36 g of (5,6-dichloro-2-isobutyl-3-oxo-2,3-dihydro-1H-isoindol-1-yl) acetic acid is thus obtained in the form of a yellow solid. (Rf=0.33, thin layer chromatography on silica gel, eluent: dichloromethane/methanol (90/10 by volume)).

d) Ethyl (5,6-dichloro-2-isobutyl-3-oxo-2,3-dihydro-1H-isoindol-1-yl)acetate

Ethyl (5,6-dichloro-2-isobutyl-3-oxo-2,3-dihydro-1H-isoindol-1-yl)acetate is prepared as described in Example 2, starting with 0.75 g of 60% sodium hydride in 45 cm³ of 1,2-dimethoxyethane, 3.71 cm³ of triethyl phosphonoacetate and 3.42 g of 5,6-dichloro-3-hydroxy-2-isobutyl-2,3-dihydroisoindol-1-one. The mixture is refluxed for 5.5 hours and is then cooled to a temperature in the region of 20° C. The reaction mixture is treated with 75 cm³ of water and then 100 cm³ of diethyl ether. After separation of the phases by settling, the aqueous phase is extracted twice with 100 cm³ of diethyl ether. The organic extracts are combined, washed with 100 cm³ of saturated brine, dried over magnesium sulfate, filtered and then concentrated to dryness under reduced pressure (2 kPa) at a temperature in the region of 40° C. The residue is purified by chromatography under argon pressure (80 kPa) on a cartridge of silica gel (particle size 32–63 µm), eluting with successive mixtures of cyclohexane/ethyl acetate (90/10 and then 80/20 by volume). The fractions comprising the expected product are combined and concentrated to dryness under reduced pressure (2 kPa) at a temperature in the region of 40° C. 0.93 g of ethyl (5,6-dichloro-2-isobutyl-3-oxo-2,3-dihydro-1H-isoindol-1-yl)acetate is thus obtained in the form of a white solid (Rf=0.74, thin layer chromatography on silica gel, eluent: cyclohexane/ethyl acetate (50/50 by volume)).

e) 5,6-Dichloro-3-hydroxy-2-isobutyl-2,3-dihydroisoindol-1-one 5,6-Dichloro-3-hydroxy-2-isobutyl-2,3-dihydroisoindol-1-one is prepared as described in Example 1, starting with 3.78 g of 4,5-dichloro-N-isobutylphthalimide in 75 cm³ of methanol and 0.75 g of potassium borohydride. The reaction mixture is stirred at a temperature in the region of 20° C. for 16 hours and is then cooled to a temperature in the region of 0° C. and distilled water is added dropwise. The methanol is then partially evaporated off under reduced pressure (2 kPa) at a temperature in the region of 40° C., followed by addition of 100 cm³ of ethyl acetate. After separation of the phases by settling, the aqueous phase is extracted twice with 75 cm³ of ethyl acetate. The organic extracts are combined, washed with 150 cm³ of brine, dried over magnesium sulfate, filtered and then concentrated to dryness under reduced pressure (2 kPa) at a temperature in the region of 40° C. 3.42 g of 5,6-dichloro-3-hydroxy-2-isobutyl-2,3-dihydroisoindol-1one are thus obtained in the form of an off-white solid. (Rf=0.69, thin layer chromatography on silica gel, eluent: cyclohexane/ethyl acetate (50/50 by volume)).

f) 4,5-Dichloro-N-isobutylphthalimide 4,5-Dichloro-N-isobutylphthalimide can be prepared as described in Example 2, starting with 10 g of 4,5-dichlorophthalic anhydride and 4.6 cm³ of isobutylamine in 100 cm³ of toluene. The reaction mixture is heated at a temperature in the region of 140° C. for 10 minutes, followed by addition of a catalytic amount of paratoluenesulfonic acid and the mixture is heated at a temperature in the region of 140° C. for 4 hours. After cooling to a temperature in the region of 40° C., the reaction mixture is concentrated to dryness under reduced pressure (2 kPa). The residue is taken up in 250 cm³ of saturated aqueous sodium bicarbonate solution and the mixture is extracted 3 times with 200 cm³ of ethyl acetate. The organic extracts are combined, washed with 200 cm³ of saturated brine, dried over magnesium sulfate, filtered and then concentrated to dryness under reduced pressure (2 kPa) at a temperature in the region of 40° C. The residue is dried in a desiccator under reduced pressure (2 kPa) at a temperature in the region of 20° C. 2.8 g of 4,5-dichloro-N-isobutylphthalimide are thus obtained in the form of a beige-colored solid (Rf=0.80, thin layer chromatography on silica gel, eluent: cyclohexane/ethyl acetate (50/50 by volume)).

EXAMPLE 19 a) N-[2-(4,7-Difluoro-2-isobutyl-3-oxo-2,3-dihydro-1H-isoindol-1-yl)acetyl]guanidine

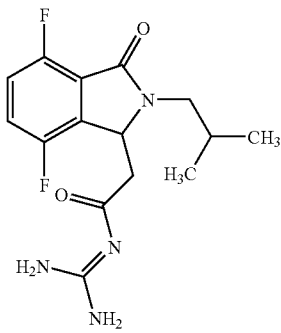

N-[(4,7-Difluoro-2-isobutyl-3-oxo-2,3-dihydro-1H-isoindol-1-yl)acetyl]guanidine is prepared as described in Example 1, starting with 2.68 g of potassium tert-butoxide, 2.74 g of guanidinium chloride and 1.49 g of ethyl (4,7-difluoro-2-isobutyl-3-oxo-2,3-dihydro-1H-isoindol-1-yl)acetate. The reaction mixture is stirred at a temperature in the region of 20° C. for 20 hours and is then filtered. The filtrate is taken up in 80 cm³ of water and 120 cm³ of ethyl acetate. After separation of the phases by settling, the organic phase is separated out and the aqueous phase is extracted twice with 120 cm³ of ethyl acetate. The organic extracts are combined, dried over magnesium 5 sulfate, filtered and concentrated to dryness under reduced pressure (0.6 kPa) at a temperature in the region of 40° C. The evaporation residue is purified by chromatography under argon pressure (50 kPa) on a column of silica gel (particle size 15–40 μm), eluting with successive mixtures of dichloromethane/methanol (95/5 and then 90/10 by volume). The fractions comprising the expected product are combined and concentrated to dryness under reduced pressure (2 kPa) at a temperature in the region of 35° C. The residue is taken up in diethyl ether, triturated, filtered and then dried in a desiccator under reduced pressure (2 kPa) at a temperature in the region of 20° C. 0.16 g of N-[(4,7-difluoro-2-isobutyl-3-oxo-2,3-dihydro-1H-isoindol-1-yl)acetyl]-quanidine is thus obtained in the form of a pale yellow solid melting at 212° C. Mass spectrum: DCI: m/e 325 (M+H)$^+$, m/e 263 (base peak).

b) Ethyl (4,7-difluoro-2-isobutyl-3-oxo-2,3-dihydro-1H-isoindol-1-yl)acetate Ethyl (4,7-difluoro-2-isobutyl-3-oxo-2,3-dihydro-1H-isoindol-1-yl)acetate is prepared as described in Example 2, starting with 0.6 g of 60% sodium hydride in 35 cm³ of 1,2-dimethoxyethane, 3.1 cm³ of triethyl phosphonoacetate and 2.5 g of 4,7-difluoro-3-hydroxy-2-isobutyl-2,3-dihydroisoindol-1-one. The crude product is purified by chromatography under argon pressure (60 kPa) on a column of silica gel (particle size 40–63 μm), eluting with successive mixtures of cyclohexane/ethyl acetate (80/20 and then 70/30 by volume). The fractions comprising the expected product are combined and concentrated to dryness under reduced pressure (2 kPa) at a temperature in the region of 20° C. 1.49 g of impure ethyl (4,7-difluoro-2-isobutyl-3-oxo-2,3-dihydro-1H-isoindol-1yl)acetate are thus obtained in the form of a dark yellow oil, which is used directly in the next step. (Rf=0.27, thin layer chromatography on silica gel, eluent: cyclohexane/ethyl acetate (70/30 by volume)).

c) 4,7-Difluoro-3-hydroxy-2-isobutyl-2,3-dihydroisoindol-1-one 4,7-Difluoro-3-hydroxy-2-isobutyl-2,3-dihydroisoindol-1-one is prepared as described in Example 1, starting with 6.41 g of 3,6-difluoro-N-isobutylphthalimide in 70 cm³ of methanol and 1.44 g of potassium borohydride. The reaction mixture is: stirred at a temperature in the region of 20° C. for 3 hours and is then cooled to a temperature in the region of 0° C. and 45 cm³ of distilled water are added dropwise. The methanol is then partially evaporated off under reduced pressure (2 kPa) at a temperature in the region of 30° C., followed by addition of 80 cm³ of dichloromethane. After separation of the phases by settling, the aqueous phase is extracted twice with 80 cm³ of dichloromethane. The organic extracts are combined, dried over magnesium sulfate, filtered and then concentrated to dryness under reduced pressure (2 kPa) at a temperature in the region of 30° C. The residue is dried in a desiccator under reduced pressure (2 kPa) at a temperature in the region of 20° C. 5.68 g of 4,7-difluoro-3-hydroxy-2-isobutyl-2,3-dihydroisoindol-1-one are thus obtained in the form of a yellow solid melting at 129.5° C. (Rf=0.48, thin layer chromatography on silica gel, eluent: cyclohexane/ethyl acetate (50/50 by volume)).

d) 3,6-Difluoro-N-isobutylphthalimide 3,6-Difluoro-N-isobutylphthalimide is prepared as described in Example 2, starting with 5.0 g of 3,6-difluorophthalic anhydride, 2.7 cm³ of isobutylamine and a catalytic amount of para-toluenesulfonic acid in 50 cm³ of toluene. The reaction mixture is refluxed for 3 hours. After cooling to a temperature in the region of 20° C., the reaction mixture is filtered and then concentrated to dryness under reduced pressure (2 kPa). The residue is taken up in 50 cm³ of saturated aqueous sodium bicarbonate solution and washed 3 times with 80 cm³ of dichloromethane. The organic extracts are combined, dried over magnesium sulfate, filtered and then concentrated to dryness under reduced pressure (2 kPa) at a temperature in the region of 40° C. 6.41 g of 3,6-difluoro-N-isobutylphthalimide are thus obtained in the form of a pale yellow solid. (Rf=0.74, thin layer chromatography on silica gel, eluent: cyclohexane/ethyl acetate (50/50 by volume)).

EXAMPLE 20 a) N-[2-(2-Isobutyl-4-methyl-3-oxo-2,3-dihydro-1H-isoindol-1-yl)-acetyl]-guanidine

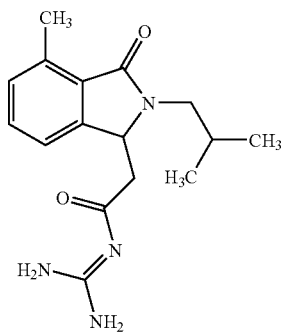

N-[2-(2-Isobutyl-4-methyl-3-oxo-2,3-dihydro-1H-isoindol-1-yl)-acetyl]-guanidine is prepared as described in Example 1, starting with 0.68 of potassium tert-butoxide, 0.58 g of guanidinium chloride and 0.36 g of ethyl (4-methyl-2-isobutyl-3-oxo-2,3-dihydro-1H-isoindol-1-yl) acetate. The reaction mixture is stirred at a temperature in the region of 20° C. for 20 hours, followed by addition of 20 cm³ of water. The aqueous phase is extracted with 3 times 100 cm³ of ethyl acetate. The organic extracts are combined and then concentrated to dryness under reduced pressure (0.5 kPa) at a temperature in the region of 40° C. The residue is taken up in dichloromethane and then concentrated again under the same conditions. The residue is taken up in water, triturated and filtered, and then taken up in dichloromethane, triturated and filtered. The solid is then dried in a desiccator. 0.21 g of N-[2-(2-Isobutyl-4-methyl-3-oxo-2,3-dihydro-1H-isoindol-1-yl)-acetyl]-guanidine is thus obtained in the form of a white powder melting at 270–272° C. (decomposition). 1NMR (300 MHz, d6-(CD$_3$)$_2$SO, δ in ppm): 0.76 (d, J=7 Hz: 3H); 0.91 (d, J=7 Hz: 3H); 2.03 (mt: 1H); 2.42 (dd, J=15.5 and 6.5 Hz: 1H); 2.60 (dd, J=15.5 and 6.5 Hz: 1H); 2.62 (s: 3H); 3.00 (dd, J=14 and 5.5 Hz: 1H); 3.56 (dd, J=14 and 10 Hz: 1H); 4.98 (t, J=6.5 Hz: 1H); from 6.40 to 7.10 (broad multiplet: 2H); 7.21 (broad d, J=7.5 Hz: 1H); 7.36 (broad d, J=7.5 Hz: 1H); 7.42 (t, J=7.5 Hz: 1H); from 7.50 to 8.30 (broad multiplet: 2H).

b) Ethyl (4-methyl-2-isobutyl-3-oxo-2,3-dihydro-1H-isoindol-1-yl)acetate

Ethyl (4-methyl-2-isobutyl-3-oxo-2,3-dihydro-1H-isoindol-1-yl)acetate is prepared as described in Example 2, starting with 0.23 g of 60% sodium hydride in 15 cm³ of 1,2-dimethoxyethane, 1.1 cm³ of triethyl phosphonoacetate and 0.63 g of 7-methyl-3-hydroxy-2-isobutyl-2,3-dihydroisoindol-1-one. The crude product is purified by chromatography under argon pressure (50 kPa) on a column of silica gel (particle size 15–40 μm), eluting with a mixture of cyclohexane/ethyl acetate (70/30 by volume). The fractions comprising the expected product are combined and concentrated to dryness under reduced pressure (2 kPa) at a temperature in the region of 40° C. 0.36 g of ethyl (4-methyl-2-isobutyl-3-oxo-2,3-dihydro-1H-isoindol-1-yl) acetate is thus obtained in the form of a colorless oil.

c) 4-Methyl-3-hydroxy-2-isobutyl-2,3-dihydroisoindol-1-one and 7-methyl-3-hydroxy-2isobutyl-2,3-dihydroisoindol-1-one 4-Methyl-3-hydroxy-2-isobutyl-2,3-dihydroisoindol-1-one and 7-methyl-3-hydroxy-2-isobutyl-2,3-dihydroisoindol-1-one are prepared as described in Example 1, starting with 5.4 g of N-isobutyl-3-methylphthalimide in 20 cm³ of methanol and 1.4 g of potassium borohydride. The reaction mixture is stirred at a temperature in the region of 20° C. for 65 hours and is then cooled to a temperature in the region of 0° C. and 10 cm³ of distilled water are added dropwise. The mixture is concentrated to dryness under reduced pressure (2 kPa) at a temperature in the region of 40° C. and the residue is taken up successively in diethyl ether and then in dichloromethane. The precipitate obtained is filtered off and the filtrate is then concentrated to dryness under reduced pressure (2 kPa) at a temperature in the region of 40° C. The residue is purified by chromatography under argon pressure (50 kPa) on a column of silica gel (particle size 15–40 μm), eluting with a mixture of cyclohexane/ethyl acetate (70/30 by volume). The fractions comprising each expected product are combined and concentrated to dryness under reduced pressure (2 kPa) at a temperature in the region of 40° C. The fractions comprising a mixture of the two expected products are combined and concentrated to dryness under reduced pressure (2 kPa) at a temperature in the region of 40° C. The residue is purified again by chromatography under argon pressure (50 kPa) on a column of silica gel (particle size 15–40 μm), eluting with a mixture of cyclohexane/ethyl acetate (80/20 by volume). The fractions comprising each expected product are combined and concentrated to dryness under reduced pressure (2 kPa) at a temperature in the region of 40° C. 0.74 g of 7-methyl-3-hydroxy-2-isobutyl-2,3-dihydroisoindol-1-one in the form of a white powder (Rf=0.54, thin layer chromatography on silica gel, eluent: cyclohexane/ethyl acetate (50/50 by volume)) and 0.89 g of 4-methyl-3-hydroxy-2-isobutyl-2,3-dihydroisoindol-1-one in the form of a cottony white solid (Rf=0.40, thin layer chromatography on silica gel, eluent: cyclohexane/ethyl acetate (50/50 by volume)) are thus obtained.

d) N-Isobutyl-3-methylphthalimide

N-Isobutyl-3-methylphthalimide is prepared as described in Example 2, starting with 5.0 g of 3-methylphthalic an hydride, 3.0 cm³ of isobutylamine and a catalytic amount of para-toluenesulfonic acid in 50 cm³ of toluene. The reaction mixture is heated at a temperature in the region of 140° C. for 2.5 hours and then stirred at a temperature in the region of 20° C. for 16 hours. The reaction mixture is concentrated to dryness under reduced pressure (2 kPa) at a temperature in the region of 40° C. The residue is taken up in dichloromethane and washed twice with saturated aqueous sodium bicarbonate solution. The organic phase is separated out after settling has taken place, dried over magnesium sulfate, filtered and then concentrated to dryness under reduced pressure (2 kPa) at a temperature in the region of 40° C. 6.0 g of N-isobutyl-3-methylphthalimide are thus obtained in the form of a caramel-colored oil, Rf=0.76 (thin layer chromatography on silica gel, eluent: dichloromethane).

EXAMPLE 21 a) N-{2-[3-Oxo-2-(2,2,2-trifluoro-ethyl)-6-trifluoromethyl-2,3-dihydro-1H-isoindol-1-yl]-acetyl}-quanidine

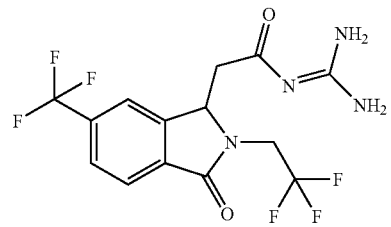

1.24 g guanidinium hydrochloride and 1.21 g of KOtBu were suspended using 30 ml of DMF(anhydrous) and stirred for 30 minutes at ambient temperature. Then, a solution of 0.8. g of [3-oxo-2-(2,2,2-trifluoro-ethyl)-6-trifluoromethyl-2,3-dihydro-1H-isoindol-1-yl]-acetic acid ethyl ester in 5 ml of DMF(anhydrous) were added and the mixture was stirred for 17 h at ambient temperature. The mixture was then poured into 100 ml of water and the pH was adjusted to pH=8 using aqueous HCl-solution. The aqueous layer was extracted three times using 100 ml of EA each. The organic layer was dried over MgSO$_4$ and the solvent was removed in vacuo. Chromatography on silica gel using EA/MeOH 3:1 yielded 0.56 g of an amorphous solid (R$_f$ (EA/MeOH 3:1)=0.45, MS (ES+): 383 (M+1)⁺).

b) [3-Oxo-2-(2,2,2-trifluoro-ethyl)-5-trifluoromethyl-2,3-dihydro-1H-isoindol-1-yl]-acetic acid ethyl ester and [3-Oxo-2-(2,2,2-trifluoro-ethyl)-6-trifluoro ethyl)-6-trifluoro ethyl-2,3-dihydro-1H-isoindol-1-yl]-acetic acid ethyl ester 0.84 g of NaH were suspended using 60 ml of DME (anhydrous) and 4.5 ml of (diethoxy-phosphoryl)-acetic acid ethyl ester added at a temperatur between 10° C. and 25° C. The mixture was stiirred at ambient temperature for 30 minutes followed by addition of a solution of 4.2 g of 3-hydroxy-2-(2,2,2-trifiuoro-ethyl 5-trifluoromethyl-2,3-dihydro-isoindol-1 -one and 3-hydoroxy-2-(2,2,2-trifiuoro-ethyl)-6-trifluoromethyl-2,3-dihydro-isoindol-1-one in 20 ml DME(anhydrous). The reaction mixture was refluxed for 1 h, then cooled to ambient temperature. 100 ml of EA were then added and the mixture washed twice using 200 ml of a semisat rated aqueous NaHCO₃-solution. The organic layer was dried over MgSO4 and the solvent was removed in vacuo. Chromatography was performed on Merck Lichrospher RP18, 10 µm, 50*250 mm. Conditions as follows:

flow 150 ml/minute eluent A: water +2% TFA eluent B: acetonitrile

Minute 00: 90% A, 10% B

Minute 04: 90% A, 10% B

Minute 24: 25% A, 75% B

Minute 25: 5% A, 95% B

Minute 30: 5% A, 95% B

Minute 31: 90% A, 10% B

Minute 35: 90% A, 10% B

Yield was 3.3 g of a mixture of regioisomeric [3-oxo-2-(2,2,2-trifluoro-ethyl)-6-trifluoromethyl-2,3-dihydro-1H-isoindol-1-yl]-acetic acid ethyl ester and [3-oxo-2-(2,2,2-trifluoro-ethyl)-5-trifluoromethyl-2,3-dihydro-1H-isoindol-1-yl]-acetic acid ethyl ester. Chromatography on silica gel using DIP yielded 0.8 g of [3-Oxo-2-(2,2,2-trifluoro-ethyl)-6-trifluoromethyl-2,3-dihydro-1H-isoindol-1-yl]-acetic acid ethyl ester as a colorless oil ($R_f$(DIP)=0.37, MS (ES+): 370 (M+1)⁺) and 0.63 g of [3-Oxo-2-(2,2,2-trifluoro-ethyl)-5-trifluoromethyl-2,3-dihydro-1H-isoindol-1-yl]-acetic acid ethyl ester as a colorless oil ($R_f$(DIP)=0.30, MS (ES+): 370 (M+1)⁺).

c) 3-Hydoroxy-2-(2,2,2-trifluoro-ethyl)-5-trifluoromethyl-2,3-dihydrol-1-isoindol-1-one and 3-Hydroxy-2-(2,2,2-trifluoro-ethyl)-6-trifluoromethyl-2,3-dihydro-isoindol-1-one 5.5 g of 2-(2,2,2-trifluoro-ethyl)-5-trifluoromethyl-isoindole-1,3-dione ere dissolved using 150 ml MeOH (anhydrous) and 1.0 g of KBH₄ added at ambien temperature. The mixture was left at ambient temperature for 16 h, cooled to 00C nd poured into 100 ml of water at 0° C. The methanol was removed in vacuo. The a viscous oil layer was extracted three times using 100 ml of CH₂Cl₂ each. The organi layer was dried over MgSO₄ and the solvent was removed in vacuo to yield 4.2 g of viscous oil ($R_f$(DIP)= 0.37, MS (DCI): 300 (M+1)⁺).

d) 2-(2,2,2-Trifluoro-ethyl)-5-trifluoromethyl-isoindole-1,3-dione 5.0 g of 5-trifluoromethyl-isobenzofuran-1,3-dione were dissolved using 50 ml of toluene(anhydrous) and 4.6 g of 2,2,2-trifluoro-ethylamine added. The mixture was left at ambient temperature for 16 h. 50 mg of toluene-4-sulfonic acid were then added and the mixture was refluxed for 5 h. 200 ml of EA were added and the mixture was washed twice using 50 ml of a 10% aqueous Na₂CO₃-solution. The organic layer was dried over MgSO₄ and the solvent was removed in vacuo to yield 5.5 g of a viscous oil ($R_f$(DIP)=0.57; MS (EI): 298 (M+1)⁺).

e) 5-Trifluoromethyl-isobenzofuran-1,3-dione 25.0 g of 4-trifluoromethyl-phthalic acid were dissolved in 50 ml of HOAc and 15.1 ml of acetic anhydride added. The mixture was refluxed for 6 h. The solvent was then removed in vacuo. The residue was treated three times with 50 ml of toluene each followed by the removal of the solvent in vacuo. Yield 23.1 g of a colorless oil ($R_f$($CH_2Cl_2$)=0.60).

EXAMPLE 22

N-[2-(3-Oxo-2-(2,2,2-trifluoroethyl)-2,3-dihydro-1H-isoindol-1-yl)acetyl]guanidine

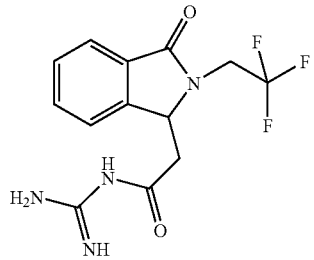

N-[(3-Oxo-2-(2,2,2-trifluoroethyl)-2,3-dihydro-1H-isoindol-1-yl)acetyl]guanidine is prepared as described in Example 21. An amorphous white powder is thus obtained, Rf=0.10 (thin layer chromatography on silica gel, eluent: ethyl acetate/methanol (5:1 by volume)). Mass spectrum: ES⁺: m/e 315.

EXAMPLE 23

N-[2-(5-Chloro-3-oxo-2-(2,2,2-trifluoroethyl)-2,3-dihydro-1H-isoindol-1-yl)acetyl]-guanidine and N-[2-(6-chloro-3-oxo-2-(2,2,2-trifluoroethyl )-2,3-dihydro-1H-isoindol-1yl)acetyl]quanidine

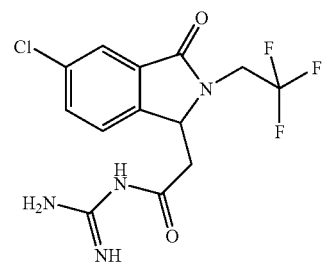

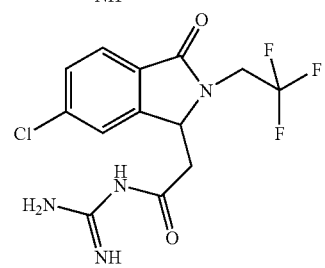

N-[(5-Chloro-3-oxo-2-(2,2,2-trifluoroethyl)-2,3-dihydro-1H-isoindol-1-yl)acetyl]guanidine and N-[(6-chloro-3-oxo-2-(2,2,2-trifluoroethyl)-2,3-dihydro-1H-isoindol-1-yl)acetyl]guanidine are prepared in the form of a mixture of two regioisomers as described in Example 21. An amorphous white powder is thus obtained, Rf=0.20 (thin layer chromatography on silica gel, eluent: ethyl acetate/methanol (5:1 by volume)). Mass spectrum: ES⁺: m/e 349.

EXAMPLE 24

N-[2-(6-Chloro-2-cyclopropylmethyl-3-oxo-2,3-dihydro-1H-isoindol-1-yl )-acetyl]-guanidine and N-[2-(5-Chloro-2-cyclopropylmethyl-3-oxo-2,3-dihydro-1H-isoindol-1 yl)-acetyl]-guanidine

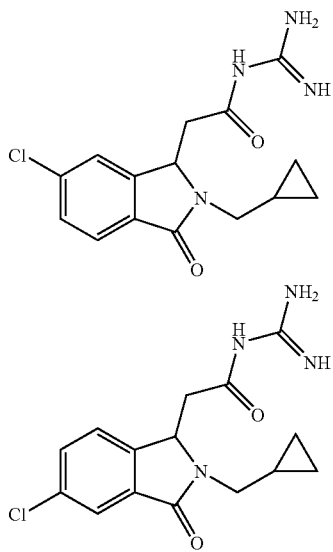

N-[(5-Chloro-2-cyclopropylmethyl-3-oxo-2,3-dihydro-1H-isoindol-1-yl )acetyl]guanidine and N-[(6-chloro-2-cyclopropylmethyl-3-oxo-2,3-dihydro-1H-isoindol-1-yl)acetyl]-guanidine are prepared in the form of a mixture of two regioisomers as described in Example 8, Rf=0.09 (thin layer chromatography on silica gel, eluent: ethyl acetate/methanol (5:1 by volume)). Mass spectrum: ES$^+$: m/e 321.

EXAMPLE 25

N-[2-(2-Cyclopropylmethyl-3-oxo-5-trifluoromethyl-2,3-dihydro-1H-isoindol-1-yl) acetyl]-guanidine and N-[2-(2-cyclopropylmethyl-3-oxo-6-trifluoromethyl-2,3-dihydro-1H-isoindol-1-yl) acetyl]guanidine

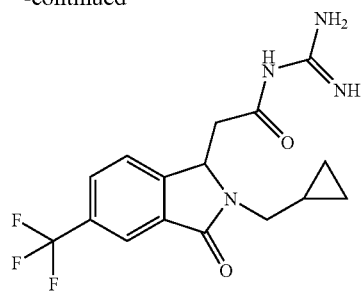

N-[(2-Cyclopropylmethyl-3-oxo-5-trifluoromethyl-2,3-dihydro-1H-isoindol-1-yl)acetyl]-guanidine and N-[(2-cyclopropylmethyl-3-oxo-6-trifluoromethyl-2,3-dihydro-1H-isoindol1-yl)acetyl]guanidine are prepared in the form of a mixture of two regioisomers as described in Example 8, Rf=0.11 (thin layer chromatography on silica gel, eluent: ethyl acetate/methanol (5:1 by volume)). Mass spectrum: ES$^+$: m/e 355.

EXAMPLE 26 a) N-[2-(5-Chloro-3-oxo-2-(3,3,3-trifluoropropyl)-2,3-dihydro-1H-isoindol-1-yl)acetyl]-guanidine and N-[2-(6-chloro-3-oxo-2-(3,3,3-trifluoropropyl)-2,3-dihydro-1H-isoindol-1-yl)acetyl]quanidine

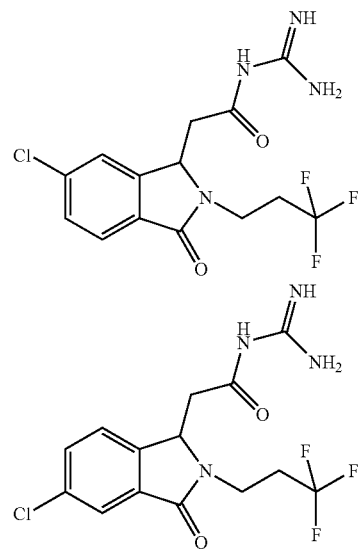

N-[(5-Chloro-3-oxo-2-(3,3,3-trifluoropropyl)-2,3-dihydro-1H-isoindol-1-yl)acetyl]-guanidine and N-[(6-chloro-3-oxo-2-(3,3,3-trifluoropropyl)-2,3-dihydro-1H-isoindol-1-yl)acetyl]guanidine are prepared in the form of a mixture of two regioisomers as described in Example 1, starting with 4-chloro-N-(3,3,3-trifluoropropyl)phthalimide, Rf=0.12 (thin layer chromatography on silica gel, eluent: ethyl acetate/methanol (5:1 by volume)). Mass spectrum: ES$^+$: m/e 363.

b) 4-Chloro-N-(3,3,3-trifluoropropyl)phthalimide

A mixture of 5.0 g of 4-chloro-N-(3,3,3-trifluoropropyl) phthalamic acid and 30 mg of para-toluenesulfonic acid in 100 cm$^3$ of toluene is refluxed with stirring for 7 hours. The reaction mixture is then concentrated to dryness under reduced pressure. 4.2 g of 4-chloro-N-(3,3,3-trifluoropropyl)phthalimide are thus obtained, Rf=0.5 (thin layer chromatography on silica gel, eluent: diisopropyl ether. Mass spectrum: DCI: m/e 278.

c) 4-Chloro-N-(3,3,3-trifluoropropyl)phthalamic acid 3.6 g of 1,1,1-trifluoro-3-iodopropane are added dropwise to a mixture of 7.5 g of 4-chlorophthalimide and 4.6 g of potassium carbonate in 40 cm³ of dimethylformamide at a temperature in the region of 110° C. with stirring. After stirring for 11 hours at a temperature in the region of 120° C., the reaction mixture is cooled to a temperature in the region of 20° C. and then poured into 200 cm³ of water. The mixture is acidified with dilute aqueous hydrochloric acid solution to a pH of about 3, and is then extracted 3 times with 100 cm³ of ethyl acetate. The organic phase is dried over magnesium sulfate and then concentrated to dryness. 5.0 g of 4-chloro-N-(3,3,3-trifluoropropyl)phthalamic acid are thus obtained, Rf=0.12 (thin layer chromatography on silica gel, eluent: ethyl acetate).

d) 4-Chlorophthalimide

A solution of 10.0 g of 4-chlorophthalic anhydride in 24.6 g of formamide is heated at a temperature in the region of 120° C. with stirring for 3 hours and is then cooled to a temperature in the region of 20° C. and poured into 100 cm³ of water. After stirring for 30 minutes, the mixture is filtered and the precipitate is then dried under vacuum at a temperature in the region of 60° C. 10.4 g of 4-chlorophthalimide are thus obtained in the form of a solid melting at 171° C. Rf=0.07 (thin layer chromatography on silica gel, eluent: dichloromethane).

EXAMPLE 27 a) N-[2-(3-Oxo-5-trifluoromethyl-2-(3,3,3-trifluoropropyl)-2,3-dihydro-1H-isoindol-1-yl)-acetyl]guanidine and N-[2-(3-oxo-6-trifluoromethyl-2-(3,3,3-trifluoropropyl)-2,3-dihydro-1H-isoindol-1-yl)acetyl]guanidine

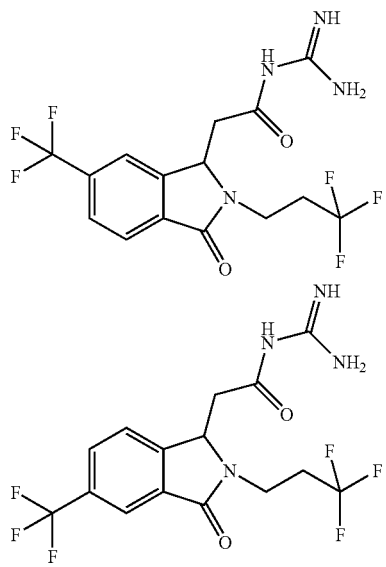

N-[(3-Oxo-5-trifluoromethyl-2-(3,3,3-trifluoropropyl)-2,3-dihydro-1H-isoindol-1-yl)acetyl]guanidine and N-[(3-oxo-6-trifluoromethyl-2-(3,3,3-trifluoropropyl)-2,3-dihydro-1H-isoindol-1-yl)acetyl]guanidine are prepared in the form of a mixture of two regioisomers as described in Example 1, starting with 4-trifluoromethyl-N-(3,3,3-trifluoropropyl)phthalimide, Rf=0.12 (thin layer chromatography on silica gel, eluent: ethyl acetate/methanol (5:1 by volume)). Mass spectrum: ES⁺: m/e 397.

b) 4-Trifluoromethyl-N-(3,3,3-trifluoropropyl)phthalimide is prepared in a similar manner to 4-chloro-N-(3,3,3-trifluoropropyl)phthalimide described in Example 26, starting with 4-trifluoromethylphthalic anhydride, Rf=0.12, (thin layer chromatography on silica gel, eluent: ethyl acetate).

4-Trifluoromethylphthalic anhydride can be prepared by adaptation or application of the method described by Cavalleri et al., J. Med. Chem., 13(1), 148–149, (1970).

EXAMPLE 28

N-[2-(5-Chloro-3-oxo-2-(4,4,4-trifluorobutyl)-2,3-dihydro-1H-isoindol-1-yl)acetyl]-guanidine and N-[2-(6-chloro-3-oxo-2-(4,4,4-trifluorobutyl)-2,3-dihydro-1H-isoindol-1yl)acetyl]guanidine

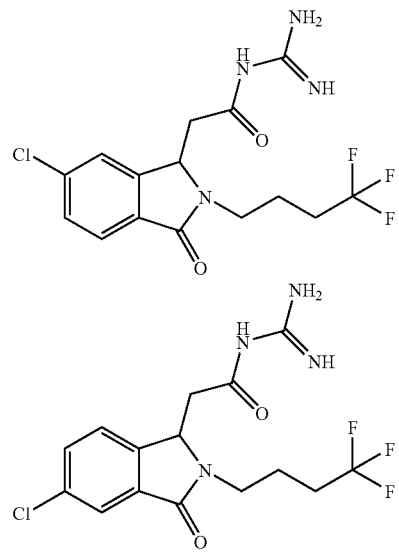

N-[(5-Chloro-3-oxo-2-(4,4,4-trifluorobutyl)-2,3-dihydro-1H-isoindol-1-yl)acetyl]guanidine and N-[(6-chloro-3-oxo-2-(4,4,4-trifluorobutyl)-2,3-dihydro-1H-isoindol-1-yl)acetyl]-guanidine are prepared in the form of a mixture of two regioisomers as described in Example 8, Rf=0.11 (thin layer chromatography on silica gel, eluent: ethyl acetate/methanol (5:1 by volume)). Mass spectrum: ES⁺: m/e 377.

EXAMPLE 29

N-[2-(3-Oxo-2-(4,4,4-trifluorobutyl)-5-trifluoromethyl-2,3-dihydro-1H-isoindol-1-yl)-acetyl]guanidine and N-[2-(3-Oxo-2-(4,4,4-trifluorobutyl)-6-trifluoromethyl-2,3-dihydro-1H-isoindol-1-yl)acetyl]guanidine

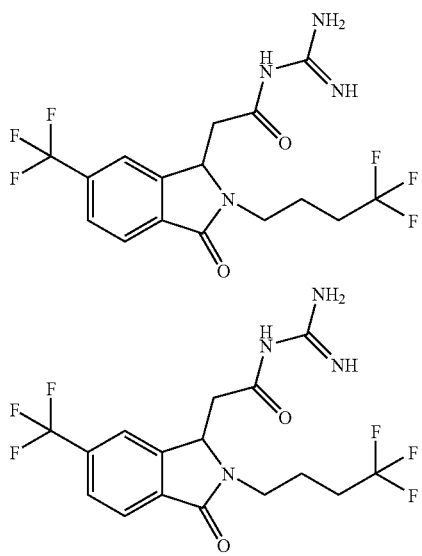

N-[(3-Oxo-2-(4,4,4-trifluorobutyl)-5-trifluoromethyl-2,3-dihydro-1H-isoindol-1-yl)acetyl]-guanidine and N-[(3-Oxo-2-(4,4,4-trifluorobutyl)-6-trifluoromethyl-2,3-dihydro-1H-isoindol-1-yl)acetyl]guanidine are prepared in the form of a mixture of two regioisomers as described in Example 27, starting with 4-trifluoromethyl-N-(4,4,4trifluorobutyl) phthalimide, Rf=0.12 (thin layer chromatography on silica gel, eluent: ethyl acetate/methanol (5:1 by volume)). Mass spectrum: ES$^+$: m/e 411.

EXAMPLE 30 a) N-[2-(3-oxo-2-propyl-2,3-dihydro-1H-isoindol-1-yl)propionyl]guanidine

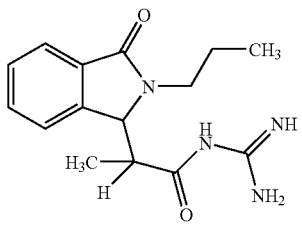

3.75 g (39.2 mmol) of guanidinium chloride are dissolved in 20 cm$^3$ of dimethylformamide and 3.96 g (35.3 mmol) of potassium tert-butoxide are added. The mixture is stirred for 45 minutes at a temperature in the region of 20° C., followed by dropwise addition of a solution of 1.08 g (3.92 mmol) of ethyl 2-methyl-3-(2-propylcarbamoylphenyl)acrylate in 15 cm$^3$ of dimethylformamide. After stirring at a temperature in the region of 20° C. for about 16 hours, the solvent is evaporated off and the residue is dissolved in aqueous 2N hydrochloric acid solution. After extraction once with dichloromethane, the aqueous phase is basified with potassium hydroxide to pH 12 and the precipitate thus obtained is filtered off*. This precipitate is taken up in aqueous 2N hydrochloric acid solution, filtered off and then freeze dried; about 400 mg of one of the two diastereomers produced (diastereomer A) are thus obtained in the form of the hydrochloride enriched in a ratio of about 6:1 (MS(ES): M+H: 289.1).

* The first filtrate. obtained is subjected to a double extraction with dichloromethane. The combined organic extracts are dried over sodium sulfate and then concentrated. The residue is taken up in aqueous 2N hydrochloric acid solution, filtered and then freeze dried. 77 mg of the second diastereomer (diastereomer B) are thus isolated in the form of the hydrochloride enriched in a ratio of 10:1 (MS (ES): M+H: 289.1).

Diastereomer A is resolved into two enantiomers by HPLC chromatography on a chiral column (Chiralpak AD 250×4.6), eluting with an acetonitrile/isopropanol/n-heptane mixture (50/3/4 by volume) containing 0.3% diethylamine; flow rate: 1 ml/min. Enantiomer A1: 3.106 min, and enantiomer A2: 3.522 min, are thus obtained.

Both enantiomers are converted to the corresponding trifluoroacetates by dissolving the free bases in aqueous diluted trifluoroacetic-acid, followed by a freeze drying procedure; enantiomer Al in the form of the trifluoroacetate ($\alpha_D^{20}$=−73° in methanol at 0.1%), enantiomer A2 in the form of the trifluoroacetate, ($\alpha_D^{20}$=+56° in methanol at 0.1%).

b) Ethyl 2-methyl-3-(2-propylcarbamoylphenyl) acrylate

A solution of 0.69 cm$^3$ (5.0 mmol) of triethylamine and 1.64 g (5.0 mmol) of O-[(cyano(ethoxycarbonyl)methylene)amino]-1,1,3,3-tetramethyluronium tetrafluoroborate ("TOTU") in 6 cm$^3$ of dimethylformamide is added at 0° C. to a solution of 1.17 g (5.0 mmol) of 2-(2-ethoxycarbonylpropen-1-yl)benzoic acid in 10 cm$^3$ of dimethylformamide. After stirring for 30 minutes at 0° C. and then for 30 minutes at a temperature in the region of 20° C., this solution is introduced dropwise into a second solution consisting of 296 mg (5.0 mmol) of n-propylamine and 0.69 cm$^3$ (5.0 mmol) of triethylamine in 10 cm$^3$ of dimethylformamide, and the mixture is stirred for a further 6 hours at a temperature in the region of 20° C. After leaving the solution to stand overnight, the solvent is removed under vacuum and the residue is dissolved in ethyl acetate. After washing twice with sodium bicarbonate solution and then once with sodium chloride solution, the organic phase is dried over sodium sulfate and then concentrated. 1.10 g of ethyl 2-methyl-3-(2-propylcarbamoylphenyl)acrylate are thus obtained in the form of a yellowish oil, which can be reacted in the following step without further purification.

c) 2-(2-Ethoxycarbonylpropen-1-yl)benzoic acid

A mixture of 5.0 g (33.3 mmol) of 2-formylbenzoic acid and 14.5 g (40.0 mmol) of ethyl 2-(triphenylphosphanylidene)propionate in 100 cm$^3$ of dimethylformamide is stirred at a temperature in the region of 20° C. for 1 hour. After removal of the solvent, the residue is dissolved in dichloromethane and then extracted twice with sodium bicarbonate solution. The aqueous phases are combined, washed with dichloromethane and then acidified with aqueous 6N hydrochloric acid solution to a pH of between 1 and 2. After extracting twice with dichloromethane, the organic phases are combined, dried over magnesium sulfate and then concentrated. 2-(2-Ethoxycarbonylpropen-1-yl)benzoic acid is thus obtained in the form of a yellow oil, which is used directly in the following step without further purification

EXAMPLE 31 a) N-[2-(2-Butyl-3-oxo-2,3-dihydro-1H-isoindol-1-yl)propionyl]guanidine

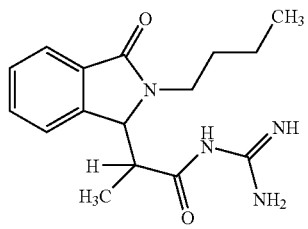

N-[2-(2-Butyl-3-oxo-2,3-dihydro-1H-isoindol-1-yl)propionyl]guanidine is prepared as described in Example 30, starting with 3.63 g (38.0 mmol) of guanidinium chloride in 20 cm³ of dimethylformamide and 3.84 g (34.2 mmol) of potassium tert-butoxide. The mixture is stirred for 45 minutes at a temperature in the region of 20° C., followed by dropwise addition of a solution of 1.10 g (3.80 mmol) of ethyl 3-(2-butylcarbamoylphenyl)-2-methylacrylate in 15 cm³ of dimethylformamide, and the mixture is stirred for 3 hours at a temperature in the region of 20° C. After leaving the solution to stand overnight, the solvent is removed and the residue is dissolved in aqueous 2N hydrochloric acid solution. After extracting once with dichloromethane, the organic phase is concentrated and the residue is then taken up in aqueous 2N hydrochloric acid solution, filtered and then freeze dried. 1.07 g of N-[2-(2-butyl-3-oxo-2,3-dihydro-1H-isoindol-1-yl)propionyl]guanidine are thus obtained in the form of a mixture of the diastereomers. The pH of the aqueous phase is adjusted to a value of 12 with potassium hydroxide and the precipitate thus obtained is filtered off*. The solid thus obtained is taken up in aqueous 2N hydrochloric acid solution and, after filtration and a freeze drying procedure, about 106 mg of one of the two diastereomers produced (diastereomer A) are obtained in the form of the hydrochloride enriched in a ratio of 5:1 (MS (ES): M+H: 303.1).

* The first filtrate obtained is subjected to a double extraction with dichloromethane.

The combined organic extracts are dried over sodium sulfate and then concentrated. The residue is taken up in aqueous 2N hydrochloric acid solution, filtered and then freeze dried; 38 mg of the second diastereomer (diastereomer B) are thus isolated in the form of the hydrochloride enriched in a ratio of greater than 10:1 (MS (ES): M+H: 303.1).

Diastereomer A is resolved into two enantiomers by HPLC chromatography on a chiral column (Chiralpak AD 250×4.6), eluting with an acetonitrile/isopropanol/n-heptane mixture (50/3/4 by volume) containing 0.3% diethylamine; flow rate: 1 ml/min. Enantiomer A1: 3.195 min, enantiomer A2: 3.714 min, are thus obtained.

Both enantiomers are converted to the corresponding trifluoroacetates by dissolving the free bases in aqueous diluted trifluoroacetic-acid, followed by a freeze drying procedure; enantiomer A1 in the form of the trifluoroacetate ($\alpha_D^{20}$=−32° in methanol at 0.2%) enantiomer A2 in the form of the trifluoroacetate, ($\alpha_D^{20}$=+42° in methanol at 0.2%).

b) Ethyl 3-(2-butylcarbamoylphenyl)-2-methylacrylate

Ethyl 3-(2-butylcarbamoylphenyl)-2-methylacrylate is prepared as described in Example 30, starting with 1.17 g (5.0 mmol) of 2-(2-ethoxycarbonylpropen-1-yl)benzoic acid in 10 cm³ of dimethylformamide, a solution of 0.69 cm³ (5.0 mmol) of triethylamine, 1.64 g (5.0 mmol) of O-[(cyano(ethoxycarbonyl)methylene)amino]-1,1,3,3-tetramethyluronium tetrafluoroborate ("TOTU") in 6 cm³ of dimethylformamide and a second solution consisting of 366 mg (5.0 mmol) of n-butylamine and 0.69 cm³ (5.0 mmol) of triethylamine in 10 cm³ of dimethylformamide. 1.13 g of ethyl 3-(2-butylcarbamoylphenyl)-2-methylacrylate are thus obtained in the form of a yellowish oil, which can be reacted in the following step without further purification.

EXAMPLE 32 a) N-[2-(2-Isobutyl-3-oxo-2,3-dihydro-1H-isoindol-1-yl)propionyl]guanidine

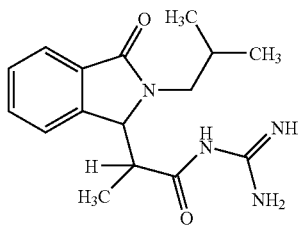

N-[2-(2-Isobutyl-3-oxo-2,3-dihydro-1H-isoindol-1-yl)propionyl]guanidine is prepared as described in Example 30, starting with 3.73 g (39.0 mmol) of guanidinium chloride in 20 cm³ of dimethylformamide and 3.94 g (35.1 mmol) of potassium tert-butoxide. The mixture is stirred for 45 minutes at a temperature in the region of 20° C., followed by dropwise addition of a solution of 1.13 g (3.90 mmol) of ethyl 3-(2-isobutylcarbamoylphenyl)-2-methylacrylate in 15 cm³ of dimethylformamide, and the mixture is stirred for 3 hours at a temperature in the region of 20° C. After leaving the solution to stand overnight, the solvent is removed and the residue is dissolved in aqueous 2N hydrochloric acid solution. After extracting once with dichloromethane, the organic phase is concentrated and the residue is then taken up in 2N hydrochloric acid solution, filtered and then freeze dried. 862 mg of N-[2-(2-isobutyl-3-oxo-2,3-dihydro-1H-isoindol-1-yl)propionyl]guanidine are thus obtained in the form of a mixture of the diastereomers. The pH of the aqueous phase is adjusted to a value of 12 with potassium hydroxide and the precipitate thus obtained is filtered off*. The solid thus obtained is taken up in aqueous 2N hydrochloric acid solution and, after filtration and a freeze drying procedure, about 255 mg of one of the two diastereomers produced (diastereomer A) are obtained in the form of the hydrochloride enriched in a ratio of 9:1 (MS(ES): M+H: 303.1).

* The first filtrate obtained is subjected to double extraction with dichloromethane. The combined organic extracts are dried over sodium sulfate and then concentrated. The residue is taken up in aqueous 2N hydrochloric acid solution, filtered and then freeze dried; 78 mg of the second diastereomer (diastereomer B) are thus isolated in the form of the hydrochloride enriched in a ratio of greater than 10:1 (MS (ES): M+H: 303.1).

Diastereomer A is resolved into two enantiomers by HPLC chromatography on a chiral column (Chiralpak AD 250×4.6), eluting with an acetonitrile/isopropanol/n-heptane mixture (50/3/4 by volume) containing 0.3% diethylamine; flow rate: 1 ml/min. Enantiomer A1: 3.895 min, enantiomer A2: 4.437 min, are thus obtained.

Both enantiomers are converted to the corresponding trifluoroacetates by dissolving the free bases in aqueous diluted trifluoroacetic-acid, followed by a freeze drying procedure; enantiomer A1 in the form of the trifluoroacetate ($\alpha_D^{20}=-43°$ in methanol at 0.2%), enantiomer A2 in the form of the trifluoroacetate, ($\alpha_D^{20}=+57°$ in methanol at 0.2%).

b) Ethyl 3-(2-isobutylcarbamoylphenyl)-2-methylacrylate

Ethyl 3-(2-isobutylcarbamoylphenyl)-2-methylacrylate is prepared as described in Example 30, starting with 1.17 g (5.0 mmol) of 2-(2-ethoxycarbonylpropen-1-yl)benzoic acid in 10 cm³ of dimethylformamide, a solution of 0.69 cm³ (5.0 mmol) of triethylamine, 1.64 g (5.0 mmol) of O-[(cyano(ethoxycarbonyl)methylene)amino]-1,1,3,3-tetramethyluronium tetrafluoroborate ("TOTU") in 6 cm³ of dimethylformamide and a second solution consisting of 366 mg (5.0 mmol) of isobutylamine, 0.69 cm³ (5.0 mmol) of triethylamine in 10 cm³ of dimethylformamide. 1.15 g of ethyl 3-(2isobutylcarbamoylphenyl)-2-methylacrylate are thus obtained in the form of a yellowish oil, which can be reacted in the following step without further purification.

EXAMPLE 33 a) N-[2-(2-Hydroxyethyl)-3-oxo-2,3-dihydro-1H-isoindol-1-yl)propionyl]guanidine

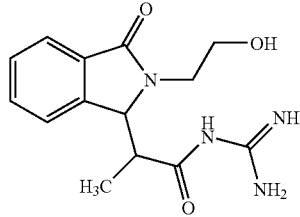

N-[2-(2-Hydroxyethyl)-3-oxo-2,3-dihydro-1-isoindol-1-yl)propionyl]guanidine is prepared as described in Example 30, starting with 3.75 g (39.2 mmol) of guanidinium chloride in 20 cm³ of dimethylformamide and 3.96 g (35.3 mmol) of potassium tertbutoxide. The mixture is stirred for 45 minutes at a temperature in the region of 20° C., followed by dropwise addition of a solution of 1.09 g (3.92 mmol) of ethyl 3-[2-(2hydroxyethylcarbamoyl)phenyl]-2-methylacrylate in 15 cm³ of dimethylformamide, and the mixture is stirred for 3 hours at a temperature in the region of 20° C. After leaving the solution to stand overnight, the solvent is removed and the residue is dissolved in aqueous 2N hydrochloric acid solution. After extraction once with dichloromethane, the pH of the aqueous phase is adjusted to a value of 12 with potassium hydroxide and the precipitate thus obtained is filtered off*. The solid thus obtained is taken up in aqueous 2N hydrochloric acid solution and, after filtration and a freeze drying procedure, about 207 mg of one of the two diastereomers produced (diastereomer A) are thus obtained in the form of the hydrochloride enriched in a ratio of 10:1 (MS (ES): M+H: 291.1).

* The first filtrate obtained is subjected to a double extraction with dichloromethane. The combined organic extracts are dried over sodium sulfate and then concentrated. The residue is taken up in aqueous 2N hydrochloric acid solution, filtered and then freeze dried; 50 mg of a mixture of the two diastereomers (diastereomers A and B) are thus isolated in the form of the hydrochloride, in a 1:1 proportion (MS(ES): M+H: 291.1).

b) Ethyl 3-[2-(2-hydroxyethylcarbamoyl)phenyl]-2-methylacrylate

Ethyl 3-[2-(2-hydroxyethylcarbamoyl)phenyl]-2-methylacrylate is prepared as described in Example 30, starting with 1.17 g (5.0 mmol) of 2-(2-ethoxycarbonylpropen-1-yl)benzoic acid in 10 cm³ of dimethylformamide, a solution of 0.69 cm³ (5.0 mmol) of triethylamine and 1.64 g (5.0 mmol) of O-[(cyano(ethoxycarbonyl)methylene)amino]1,1,3,3-tetramethyluronium tetrafluoroborate ("TOTU") in 6 cm³ of dimethylformamide, and a second solution consisting of 306 mg (5.0 mmol) of ethanolamine and 0.69 cm³ (5.0 mmol) of triethylamine in 10 cm³ of dimethylformamide. 1.14 g of ethyl 3-[2-(2hydroxyethylcarbamoyl)phenyl]-2-methacrylate are thus obtained in the form of a yellowish oil, which can be reacted in the following step without further purification.

EXAMPLE 34 a) N-[2-(2-Isobutyl-5-methyl-3-oxo-2,3-dihydro-1H-isoindol-1-yl)acetyl]guanidine

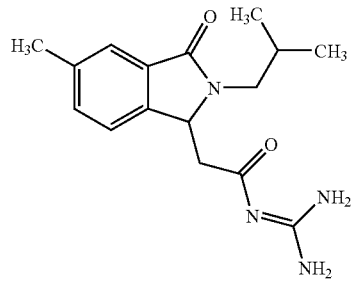

N-[(2-Isobutyl-5-methyl-3-oxo-2,3-dihydro-1H-isoindol-1-yl)acetyl]guanidine is prepared as described in Example 1, starting with 1.75 g of potassium tert-butoxide, 1.78 g of guanidinium chloride and 0.9 g of ethyl (2-isobutyl-5-methyl-3-oxo-2,3-dihydro-1H-isoindol-1-yl)acetate. The reaction mixture is stirred at a temperature in the region of 20° C. for 40 hours and is then poured into 150 cm³ of water and extracted with 3 times 150 cm³ of ethyl acetate. The organic extracts are combined, washed with-3 times 50 cm³ of water, dried over magnesium sulphate, filtered and then concentrated to dryness under reduced pressure (2.7 kPa) at a temperature in the region of 40° C. The residue is taken up in diethyl ether and then filtered, giving 0.66 g of N-[(2-isobutyl-5-methyl-3-oxo-2,3-dihydro-1H-isoindol-1-yl)acetyl]guanidine in the form of a white solid melting at 266° C. (Analysis $C_{16}H_{22}N_4O_2$% calculated C : 63.56, H : 7.33, N: 18.53, O: 10.58% found C : 63.57, H: 7.48, N: 18.50).

b) Ethyl (2-isobutyl-5-methyl-3-oxo-2,3-dihydro-1H-isoindol-1-yl)acetate

Ethyl (2-isobutyl-5-methyl-3-oxo-2,3-dihydro-1-isoindol-1-yl)acetate is prepared as described in Example 2, starting with 0.19 g of 75% sodium hydride in 25 cm³ of 1,2-dimethoxyethane, 1.2 cm³ of triethyl phosphonoacetate and 0.85 g of 3-hydroxy-2isobutyl-6-methyl-2,3-dihydroisoindol-1-one. The crude product is purified by chromatography on a column of silica gel (particle size 15–45 µm), eluting with a mixture of dichloromethane/methanol (99/1 by volume). The fractions containing the expected product are combined and concentrated to dryness under reduced pressure (2.7 kPa) at a temperature in the region of 40° C. 1 g of ethyl (2-isobutyl-5-methyl-3-oxo-2, 3-dihydro-1H-isoindol-1-yl)acetate is obtained in the form of a colourless oil, which is used directly in the following step.

EXAMPLE 35 a) N-[(2-Isobutyl-6-methyl-3-oxo-2,3-dihydro-1H-isoindol-1-yl)acetyl]guanidine

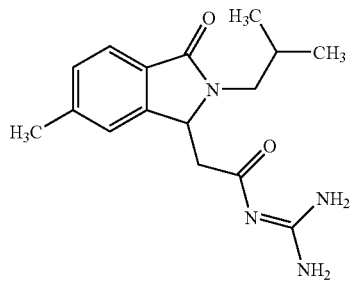

N-[(2-Isobutyl-6-methyl-3-oxo-2,3-dihydro-1H-isoindol-1-yl)acetyl]guanidine is prepared as described in Example 1, starting with 2.52 g of potassium tert-butoxide, 2.58 g of guanidinium chloride and 1.3 g of ethyl (2-isobutyl-6-methyl-3-oxo-2,3-dihydro-1-isoindol-1yl)acetate. The reaction mixture is stirred at a temperature in the region of 20° C. for 40 hours and is then poured into 150 cm³ of water and extracted with 3 times 150 cm³ of ethyl acetate. The organic extracts are combined, washed with twice 50 cm³ of water, dried over magnesium sulphate, filtered and then concentrated to dryness under reduced pressure (2.7 kPa) at a temperature in the region of 40° C. The residue is taken up in diethyl ether and then filtered, giving 0.81 g of N-[(2-isobutyl-6-methyl-3-oxo-2,3-dihydro-1H-isoindol-1-yl)acetyl]guanidine in the form of a white solid melting above 260° C. (Rf=0.28, thin layer chromatography on silica gel, eluent: dichloromethane/methanol (90/10 by volume)). (Analysis $C_{16}H_{22}N_4O_2$% calculated C: 63.56, H: 7.33, N: 18.53, O: 10.58% found C: 63.40, H: 7.33, N: 18.37).

b) Ethyl (2-isobutyl-6-methyl-3-oxo-2,3-dihydro-1H-isoindol-1-yl)acetate

Ethyl (2-isobutyl-6-methyl-3-oxo-2,3-dihydro-1H-isoindol-1-yl)acetate is prepared as described in Example 2, starting with 0.24 g of 75% sodium hydride in 30 cm³ of 1,2-dimethoxyethane, 1.5 cm³ of triethyl phosphonoacetate and 1.1 g of 3-hydroxy-2isobutyl-5-methyl-2,3-dihydroisoindol-1-one. The crude product is purified by chromatography on a column of silica gel (particle size 15–45 μm), eluting with a mixture of cyclohexane/ethyl acetate (50/50 by volume). The fractions containing the expected product are combined and concentrated to dryness under reduced pressure (2.7 kPa) at a temperature in the region of 40° C. 1.4 g of ethyl (2-isobutyl-6-methyl-3-oxo-2,3-dihydro-1H-isoindol-1-yl)acetate is obtained in the form of a colourless oil, which is used directly in the following step.

c) 3-Hydroxy-2-isobutyl-5-methyl-2,3-dihydroisoindol-1-one and 3-Hydroxy-2-isobutyl-6-methyl-2,3-dihydroisoindol-1-one 3-Hydroxy-2-isobutyl-5-methyl-2,3-dihydroisoindol-1-one and 3-hydroxy-2-isobutyl-6-methyl-2,3-dihydroisoindol-1-one are prepared as described in Example 1, starting with 6.7 g of N-isobutyl-4-methylphthalimide in 65 cm³ of methanol and 1.7 g of potassium borohydride. The reaction mixture is stirred at a temperature in the region of 20° C. for 16 hours, 0.3 g of potassium borohydride is then added, and the reaction mixture is stirred at a temperature in the region of 20° C. for two hours. The mixture is then cooled to a temperature, in the region of 0° C., and 40 cm³ of distilled water are added dropwise. The precipitate obtained is filtered off, and the filtrate is then concentrated to dryness under reduced pressure (2 kPa) at a temperature in the region of 25° C. The residue is purified by chromatography under a pressure of argon (50 kPa), on a column of silica gel (particle size 40–63 μm), eluting successively with mixtures of cyclohexane/ethyl acetate (70/30; 60/40 by volume). The fractions containing a mixture of the two expected products are combined and concentrated to dryness under reduced pressure (2 kPa) at a temperature in the region of 25° C. 2.27 g of a mixture of 3-hydroxy-2-isobutyl-5-methyl-2,3-dihydroisoindol-1-one and 3-hydroxy-2-isobutyl-6-methyl-2,3-dihydroisoindol-1-one are thus obtained in the form of a white solid (Rf=0.54, thin layer chromatography on silica gel, eluent: cyclohexane/ethyl acetate (50/50 by volume)). A second batch starting with 3.5 g of N-isobutyl-4-methylphthalimide in the same way yields 2.2 g of a mixture of 3-hydroxy-2-isobutyl-5-methyl-2,3-dihydroisoindol-1-one and 3-hydroxy-2-isobutyl-6-methyl-2,3-dihydroisoindol-1-one in the form of a white solid. The two batches are combined and then separated by HPLC chromatography on a system comprising two columns of 60 mm in diameter in series containing, respectively, 700 g and 475 g of CHIRALPAK AS chiral stationary phase with a particle size of 20 μm, eluting with a heptane/isopropanol mixture (90/10 by volume) at a flow rate of 90 ml/min. The first and second isomers eluted correspond to the first pair of regioisomers. The third and fourth isomers eluted correspond to the second pair of regioisomers. Three injections of 1 g, 1.6 g and 1.7 g, respectively, were performed under these conditions. Concentrating the fractions under reduced pressure (1 kPa) at a temperature in the region of 40° C. gives the following: 0.77 g of (+)-3hydroxy-2-isobutyl-5-methyl-2,3-dihydroisoindol-1-one in the form of a white solid, ($\alpha_D^{20}$=+17.30°±0.80° in methanol, at a concentration of 0.5%), 1.09 g of (+)-3-hydroxy-2-isobutyl-6-methyl-2,3-dihydroisoindol-1-one in the form of a white solid, ($\alpha_D^{20}$=+23.20°±0.70° in methanol, at a concentration of 0.5%), 1.17 9 of (−)-3-hydroxy-2-isobutyl-6-methyl-2,3-dihydroisoindol-1-one in the form of a white solid ($\alpha_D^{20}$=−20.1°±1.80° in methanol, at a concentration of 0.5%), and 0.85 g of (−)-3-hydroxy-2-isobutyl-5-methyl-2,3-dihydroisoindol-1-one in the form of a white solid, ($\alpha_D^{20}$=−15.60°±0.60° in dichloromethane, at a concentration of 0.5%).

d) N-Isobutyl-4-methylphthalimide

N-Isobutyl-4-methylphthalimide is prepared as described in Example 2, starting with 6.0 g of 4-methylphthalic anhydride, 3.7 cm³ of isobutylamine and a catalytic amount of para-toluenesulphonic acid in 60 cm³ of toluene. The reaction mixture is heated at a temperature in the region of 140° C. for three hours and is then cooled to a temperature in the region of 20° C. The reaction mixture is concentrated to dryness under reduced pressure (2 kPa) at a temperature in the region of 40° C. The residue is taken up in 50 cm³ of saturated aqueous sodium bicarbonate solution, and the mixture is then extracted twice with 75 cm³ of dichloromethane. The organic extracts are combined, dried over sodium sulphate, filtered and then concentrated to dryness under reduced pressure (2 kPa) at a temperature in the region of 30° C., giving 6.7 g of N-isobutyl-4-methylphthalimide in the form of a white solid melting at 102° C.

EXAMPLE 36 a) (R)-N-{2-[6-Methanesulfonyl-3-oxo-2-(2,2,2-trifluoro-ethyl)-2,3-dihydro-1H-isoindol-1-yl]-acetyl}-quanidine and

(S)-N-{2-[6-Methanesulfonyl-3-oxo-2-(2,2,2-trifluoro-ethyl)-2,3-dihydro-1H-isoindol-1-yl]-acetyl}-quanidine

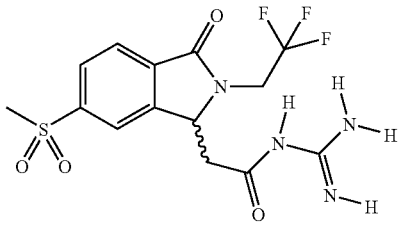

1.6 g of KOtBu were dissolved using 22 ml of DMF (anhydrous). This solution was added to a solution prepared of 1.5 g guanidine-hydrochloride using 15 ml of DMF (anhydrous). The mixture was stirred for 30 minutes at ambient temperature. Then, a solution prepared of 1.1 g [6-methanesulfonyl-3-oxo-2-(2,2,2-trifluoro-ethyl)-2,3-dihydro-1H-isoindol-1-yl]-acetic acid ethyl ester using 15 ml DMF(anhydrous) was added. The reaction mixture was stirred at ambient temperature for 22 h. Afterwards, the mixture was taken up in 500 ml of semisaturated aqueous NaHCO$_3$ solution and extracted twice using 200 ml of ethyl acetate each time. The EA layer was dried over Na$_2$SO$_4$ and the solvent was removed in vacuo. Chromatography on silica gel using EA/MeOH 3:1 yielded 0.28 g of an amorphous solid (R$_f$ (EA/MeOH 3:1)=0.15; MS (ES+): 393 (M+1)$^+$).

b) [6-Methanesulfonyl-3-oxo-2-(2,2,2-trifluoro-ethyl)-2,3-dihydro-1H-isoindol-1-yl]acetic acid ethyl ester 0.56 g of a 60% suspension of NaH in mineral oil were suspended in 20 ml of DME. Afterwards, 2.8 ml of (diethoxy-phosphoryl)-acetic acid ethyl ester were added dropwise at ambient temperature and the mixture stirred for 1 h at that temperature. A solution prepared of 3-hydroxy-5-methanesulfonyl-2-(2,2,2-trifluoro-ethyl)-2,3-dihydro-isoindol-1-one using 30 ml of DME was then added and the mixture was heated up to reflux. The mixture was refluxed for 4 h and then allowed to cool to ambient temperature. 300 ml of EA were added and the mixture was washed 3 times using 100 ml of saturated aqueous NaHCO$_3$ solution each time. The aqueous layer was then extracted twice using 100 ml of EA each time. The combined EA layers were dried over Na$_2$SO$_4$ and the solvent was removed in vacuo. Chromatography on silica gel using MTB yielded 1.1 g of a colorless oil (R$_f$ (MTB)=0.40; MS (DCI): 380 (M+1)$^+$).

b) 3-Hydroxy-5-methanesulfonyl-2-(2,2,2-trifluoro-ethyl)-2,3-dihydro-isoindol-1-one 3.4 g of 5-methanesulfonyl-2-(2,2,2-trifluoro-ethyl)-isoindole-1,3-dione were dissolved using 240 ml of MeOH. 0.63 g of KBH$_4$ were then added in small portions at ambient temperature. The reaction mixture was stirred for 20 h at ambient temperature and subsequently poured into 1 l of water at 0° C. The aqueous layer was then extracted three times using 300 ml of CH$_2$Cl$_2$ each time. Then, the aqueous layer was extracted four times using 300 ml of EA each time. Each organic layer was dried separately over Na$_2$SO$_4$. The solvents were removed in vacuo. The EA layer yielded 1.4 g pure product as a pale yellow oil. The CH$_2$Cl$_2$ layer was chromatographed on silica gel using EA/HEP 1:2 yielding another 1.5 g of product (R$_f$ (EA/HEP 1:2)=0.035; MS (DCI): 310 (M+1)$^+$)

c) 5-Methanesulfonyl-2-(2,2,2-trifluoro-ethyl)-isoindole-1,3-dione 4.0 g of 5-methylsulfanyl-2-(2,2,2-trifluoro-ethyl)-isoindole-1,3-dione were dissolved using 100 ml of CH$_2$Cl$_2$ and 7.2 g of 3-chloro-benzenecarboperoxoic acid added in small portions at ambient temperature. The mixture was stirred at ambient temperature for 12 h and left at that temperature for another 60 h. Thereafter, 400 ml of CH$_2$Cl$_2$ were added, washed twice using 150 ml of saturated aqueous Na$_2$SO$_3$, and finally washed three times using semisaturated aqueous Na$_2$CO$_3$. The organic layer was dried over Na$_2$SO$_4$. The solvents were removed in vacuo to yield 3.4 g of an amorphous solid (R$_f$ (EA)=0.13; MS (DCI): 308 (M+1)$^+$).

d) 5-Methylsulfanyl-2-(2,2,2-trifluoro-ethyl)-isoindole-1,3-dione 4.0 g of 5-chloro-2-(2,2,2-trifluoro-ethyl)-isoindole-1,3-dione (see example 23), 4.1 g K$_2$CO$_3$, and 1.1 g of sodium methanethiolate were suspended using 50 ml of DMF (anhydrous). The mixture was stirred at 80° C. for 9 h and, after cooling, it was diluted with 400 ml of semisaturated aqueous NaHCO$_3$ solution and extracted four times using 200 ml of ethyl acetate each time. The organic layer was dried over Na$_2$SO$_4$. The solvents were removed in vacuo to yield 4.1 g of an amorphous solid (R$_f$ (EA/HEP 1:2)=0.43; MS (DCI): 276 (M+1)$^+$).

The title compounds of example 36a and 36b were prepared by chromatography of 270 mg of example 36 on Chiralpak AD-H, 250×20 mm, 10 µm using ACN/HEP/i-PrOH 50:6:3 at a flow of 6 ml/minute:

EXAMPLE 36a

Yield 12 mg of an amorphous solid.

Analytical HPLC on Chiralpak AD-H/33, 250×4.6 using ACN/HEP/i-PrOH 50:6:3 at a flow of 1 ml/minute: RT=3.772 minutes.

EXAMPLE 36b

Yield 11 mg of an amorphous solid.

Analytical HPLC on Chiralpak AD-H/33, 250×4.6 using ACN/HEP/i-PrOH 50:6:3 at a flow of 1 ml/minute: RT=5.601 minutes.

EXAMPLE 37

N-[2-(2-Cyclopropylmethyl-6-methanesulfonyl-3-oxo-2,3-dihydro-1H-isoindol-1-yl)acetyl]-guanidinium acetate

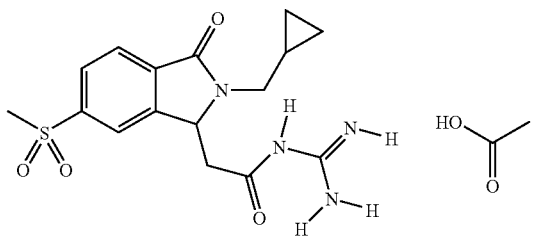

The title compound of example 37 was synthesized analogously to example 36 using 5-chloro-2-cyclopropylmethyl-isoindole-1,3-dione (see example 24) as the starting material.

($R_f$(EA/5% HOAc)=0.047; MS (ES+): 365 (M+1)$^+$)

EXAMPLE 38 a) (R)-N-[2-(2-Cyclopropylmethyl-3-oxo-6-trifluoromethyl-2,3-dihydro-1H-isoindol-1-yl)acetyl]-guanidine and (S)-N-[2-(2-Cyclopropylmethyl-3-oxo-6-trifluoromethyl-2,3-dihydro-1H-isoindol-1-yl)acetyl]-guanidine

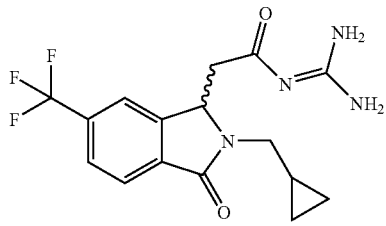

0.3 g of (2-cyclopropylmethyl-3-oxo-6-trifluoromethyl-2,3-dihydro-1H-isoindol-1-yl)acetic acid were dissolved using 5 ml of NMP(anhydrous). 0.3 g CDI were added and the mixture stirred for 17 h at ambient temperature to yield the 2-cyclopropylmethyl-3(2-imidazol-1-yl-2-oxo-ethyl)-5-trifluoromethyl-2,3-dihydro-isoindol-1-one intermediate. In the meantime, 0.55 g guanidine hydrochloride and 0.54 g KOtBu were suspended using 10 ml NMP(anhydrous) and the mixture stirred for 30 minutes at ambient temperature. Thereafter, this solution was added to the above imidazolide and the reaction mixture was left for 15 h at ambient temperature. 100 ml of EA were added and washed three times using 100 ml of semisaturated aqueous NaHCO$_3$ solution each. The organic layer was dried over MgSO$_4$ and the solvent was removed in vacuo. Chromatography on silica gel using EA/MeOH 3:1 yielded 0.21 g of an amorphous solid ($R_f$(EA/MeOH 5:1)=0.25; MS (ES+):355 (M+1)$^+$).

b) (2-Cyclopropylmethyl-3-oxo-6-trifluoromethyl-2,3-dihydro-1H-isoindol-1-yl)-acetic acid 1.0 g of (2-cyclopropylmethyl-3-oxo-6-trifluoromethyl-2,3-dihydro-1H-isoindol-1-yl)acetic acid ethyl ester were dissolved using 10 ml of ethanol and 3.5 ml of a 1 N aqueous solution of NaOH added. The mixture was stirred for 3 h at ambient temperature and then the solvent removed in vacuo. Afterwards, 30 ml of water were added and the pH of the solution adjusted to pH=2 using aqueous HCl-solution. The solution was then extracted three times using 50 ml of EA each. The organic layer was dried over MgSO$_4$ and the solvent was removed in vacuo to yield 0.35 g of an amorphous solid ($R_f$(EA/MeOH 5:1)=0.43; MS (ES+): 314 (M+1)$^+$).

c) A mixture of (2-cyclopropylmethyl-3-oxo-6-trifluoromethyl-2,3-dihydro-1H-isoindol-1-yl)-acetic acid ethyl ester and (2-Cyclopropylmethyl-3-oxo-5-trifluoromethyl-2,3dihydro-1H-isoindol-1-yl)-acetic acid ethyl ester was synthesized analogously to example 8.

To separate the regioisomers, a chromatography of 10.5 g of the mixture was carried out in 9 runs on a Merck Lichrospher column, RP18, 10 µm 50*250 mm. Conditions as follows:

Flow 150 ml/minute

Eluent A: Water+0.2% TFA

Eluent B: Acetonitrile

Minute 00: 65% A, 35% B

Minute 38: 65% A, 35% B

Minute 40: 10% A, 90% B

Minute 45: 10% A, 90% B

Minute 46: 65% A, 35% B

Minute 50: 65% A, 35% B

Yield:

0.84 g of (2-cyclopropylmethyl-3-oxo-5-trifluoromethyl-2,3-dihydro-1H-isoindol-1-yl)acetic acid ethyl ester $R_f$(DIP)=0.24 and 1.0 g of (2-cyclopropylmethyl-3-oxo-6-trifluoromethyl-2,3-dihydro-1H-isoindol-1-yl)acetic acid ethyl ester $R_f$(DIP)=0.30

The title compounds of example 38a and 38b were prepared by chromatography of 207 mg of example 38 on Chiralcel OJ, 250×50 mm, 20 µm using HEP/EtOH/MeOH 25:1:1+0.1% DEA at a flow of 100 ml/minute:

EXAMPLE 38a

Yield 30 mg of an amorphous solid.

Analytical HPLC on Chiralcel OJ/16, 250×4.6 using HEP/EtOH/MeOH 25:1:1+0.1%

DEA at a flow of 1.0 ml/minute: RT=8.763 minutes

EXAMPLE 38b

Yield 25 mg of an amorphous solid.

Analytical HPLC on Chiralcel OJ/16, 250×4.6 using ACN/HEP/i-PrOH 50:5:2+0.3%

DEA at a flow of 1.0 ml/minute: RT=10.598 minutes

EXAMPLE 39

N-[2-(2-Cyclopropylmethyl-3-oxo-5-trifluoromethyl-2,3-dihydro-1H-isoindol-1-yl)acetyl]-guanidine

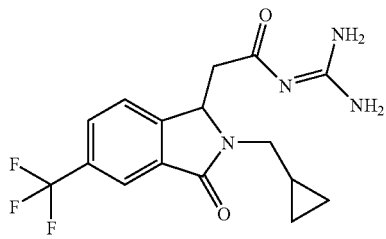

The title compound of example 39 was synthesized analogously to example 38 using (2-cyclopropylmethyl-3-oxo-5-trifluoromethyl-2,3-dihydro-1H-isoindol-1-yl)-acetic acid ethyl ester as the starting material.

($R_f$(EA/MeOH 3:1)=0.21; MS (ES+): 355 (M+1)$^+$).

EXAMPLE 40

(R)-N-{2-[5,6-Difluoro-3-oxo-2-(3,3,3-trifluoro-propyl)-2,3-dihydro-1H-isoindol-1-yl]-acetyl}-guanidine and (S)-N-{2-[5,6-Difluoro-3-oxo-2-(3,3,3-trifluoro-propyl)-2,3-dihydro-1H-isoindol-1-yl]-acetyl}-guanidine

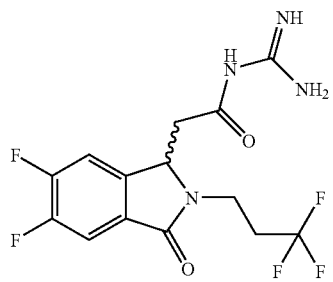

The title compound of example 40 was synthesized analogously to example 27.

($R_f$(EA/MeOH 3:1)=0.33; MS (ES+): 365 (M+1)$^+$).

The title compounds of example 40a and 40b were prepared by chromatography of 207 mg of example 40 on Chiralpak AD-H, 250×20 mm, 10 μm using ACN/HEP/i-PrOH 50:3:6+0.1% DEA at a flow of 19 ml/minute:

EXAMPLE 40a

Yield 30 mg of an amorphous solid.

Analytical HPLC on Chiralpak AD-H/33, 250×4.6 using ACN/HEP/i-PrOH 50:3:6+0.1% DEA at a flow of 1.0 ml/minute: RT=4.708 minutes

EXAMPLE 40b

Yield 30 mg of an amorphous solid.

Analytical HPLC on Chiralpak AD-H/33, 250×4.6 using ACN/HEP/i-PrOH 50:3:6+0.1% DEA at a flow of 1.0 ml/minute: RT=9.719 minutes

EXAMPLE 41

(R)-N-{2-[5,6-Dichloro-3-oxo-2-(3,3,3-trifluoro-propyl)-2,3-dihydro-1H-isoindol-1-yl]-acetyl}-guanidine and (S)-N-{2-[5,6-Dichloro-3-oxo-2-(3,3,3-trifluoro-propyl)-2,3-dihydro-1H-isoindol-1-yl]-acetyl}-guanidine

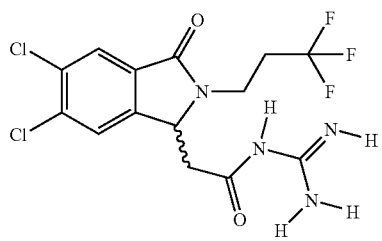

The title compounds of example 41 were synthesized analogously to example 27. The free base was converted to the acetate during chromatography on silica gel using EA/5% HOAc.

EXAMPLE 41a

N-{2-[5,6-Dichloro-3-oxo-2-(3,3,3-trifluoro-propyl)-2,3-dihydro-1H-isoindol-1-yl]-acetyl}-guanidine acetate

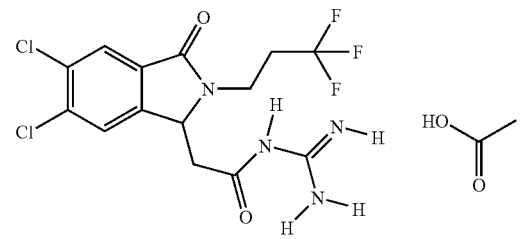

($R_f$(EA/5% HOAc)=0.16; MS (ES+): 397 (M+1)$^+$).

The title compounds of example 41b and 41c were prepared by chromatography of 530 mg of example 41a on Chiralcel OJ, 250×50 mm, 20 μm using HEP/EtOH/MeOH 10:1:1+0.1% DEA at a flow of 100 ml/minute:

EXAMPLE 41b

Yield 165 mg of the amorphous free base.

Analytical HPLC on Chiralcel OJ/37, 250×4.6 mm, using HEP/EtOH/MeOH 20:1:1+0.1% DEA at a flow of 1.0 ml/minute: RT=11.838 minutes

EXAMPLE 41c

Yield 122 mg of the amorphous free base.

Analytical HPLC on Chiralcel OJ/37, 250×4.6 mm, using HEP/EtOH/MeOH 20:1:1+0.1% DEA at a flow of 1.0 ml/minute: RT=16.029 minutes The title compounds of example 42 to 45 were synthesized analogously to example 8:

EXAMPLE 42

(R)-N-[2-(5,6-Dichloro-2-cyclopropylmethyl-3-oxo-2,3-dihydro-1H-isoindol-1-yl)-acetyl]-guanidine and (S)-N-[2-(5,6-Dichloro-2-cyclopropylmethyl-3-oxo-2,3-dihydro-1H-isoindol-1-yl)-acetyl]-guanidine

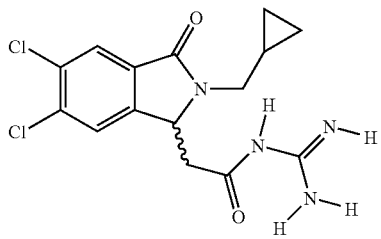

($R_f$(EA/MeOH 5:1)=0.082; MS (ES+): 355 (M+1)$^+$).

The title compounds of example 42a and 42b were prepared by chromatography of 830 mg of example 42 on Chiralcel OJ, 250×50 mm, 20 μm using HEP/EtOH/MeOH 25:1:1+0.1% DEA at a flow of 100 ml/minute:

EXAMPLE 42a

Yield 113 mg of an amorphous solid.

Analytical HPLC on Chiralcel OJ/16, 250×4.6 using HEP/EtOH/MeOH 25:1:1+0.1% DEA at a flow of 1.0 ml/minute: RT=11.691 minutes

EXAMPLE 42b

Yield 199 mg of an amorphous solid.

Analytical HPLC on Chiralcel OJ/16, 250×4.6 using HEP/EtOH/MeOH 25:1:1+0.1% DEA at a flow of 1.0 ml/minute: RT=14.032 minutes

EXAMPLE 43

(R)-N-[2-(5,6-Dichloro-2-cyclopropyl-3-oxo-2,3-dihydro-1H-isoindol-1-yl)-acetyl]-guanidine and (S)-N-[2-(5,6-Dichloro-2-cyclopropyl-3-oxo-2,3-dihydro-1H-isoindol-1-yl)-acetyl]-guanidine

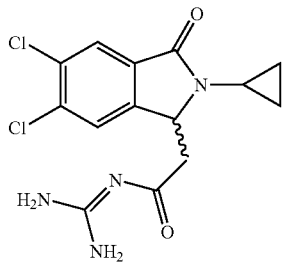

($R_f$(EA/MeOH 2:1)=0.13; MS (ES+): 341 (M+1)$^+$).

The title compounds of example 43a and 43b were prepared by chromatography of 110 mg of example 43 on Chiralpak AD-H, 250×20 mm, 10 μm using HEP/EtOH/MeOH 1:1:1+0.1% DEA at a flow of 10–15 ml/minute:

EXAMPLE 43a

Yield 60 mg of an amorphous solid.

Analytical HPLC on Chiralpak AD-H/31, 250×4.6 using HEP/EtOH/MeOH 1:1:1+0.1% DEA at a flow of 1.0 ml/minute: RT=6.420 minutes

EXAMPLE 43b

Yield 41 mg of an amorphous solid.

Analytical HPLC on Chiralpak AD-H/31, 250×4.6 using HEP/EtOH/MeOH 1:1:1+0.1% DEA at a flow of 1.0 ml/minute: RT=15.401 minutes

EXAMPLE 44

(R)-N-{2-[5,6-Dichloro-3-oxo-2-(2,2,2-trifluoro-ethyl)-2,3-dihydro-1H-isoindol-1-yl]-acetyl}-guanidine and (S)-N-{2-[5,6-Dichloro-3-oxo-2-(2,2,2-trifluoro-ethyl)-2,3-dihydro-1H-isoindol-1-yl]-acetyl}-guanidine

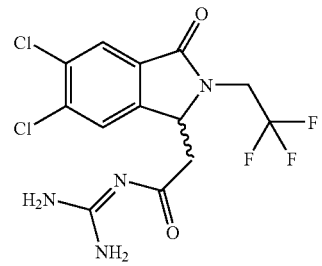

The free base was converted to the acetate during chromatography on silica gel using EA/5% HOAc.

EXAMPLE 44a

N-{2-[5,6-Dichloro-3-oxo-2-(2,2,2-trifluoro-ethyl)-2,3-dihydro-1H-isoindol-1-yl]-acetyl}-guanidine acetate

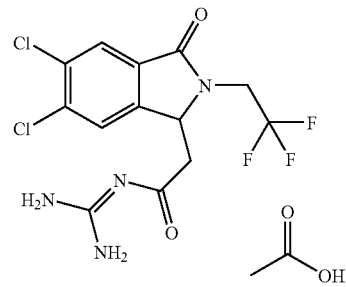

($R_f$(EA/5% HOAC)=0.27; MS (ES+): 383 (M+1)$^+$).

The title compounds of example 44b and 44c were prepared by chromatography of 100 mg of example 44a on Chiralpak AD-H, 250×20 mm, 10 μm using HEP/EtOH/MeOH 2:1:1+0.1% DEA at a flow of 14 ml/minute:

EXAMPLE 44b

Yield 25 mg of the amorphous free base.

Analytical HPLC on Chiralpak AD-H/31, 250×4.6 mm, using HEP/EtOH/MeOH 20:1:1+0.1% DEA at a flow of 1.0 ml/minute: RT=5.027 minutes

EXAMPLE 44c

Yield 26 mg of the amorphous free base.

Analytical HPLC on Chiralpak AD-H/31, 250×4.6 mm, using HEP/EtOH/MeOH 20:1:1+0.1% DEA at a flow of 1.0 ml/minute: RT=9.012 minutes

EXAMPLE 45

N-{2-[5,6-Difluoro-3-oxo-2-(2,2,2-trifluoro-ethyl)-2,3-dihydro-1H-isoindol-1-yl]-acetyl}-guanidine

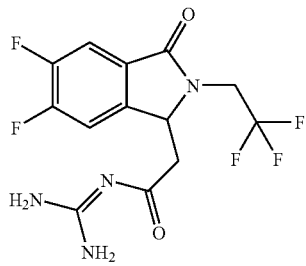

(R$_f$(EA/MeOH 3:1)=0.21; MS (ES+):351 (M+1)$^+$).

EXAMPLE 46

(R)-N-{2-[3-Oxo-2-(2,2,2-trifluoro-ethyl)-6-trifluoromethyl-2,3-dihydro-1H-isoindol-1-yl]-acetyl}-guanidine and (S)-N-{2-[3-Oxo-2-(2,2,2-trifluoro-ethyl)-6-trifluoromethyl-2,3-dihydro-1H-isoindol-1-yl]-acetyl}-guanidine

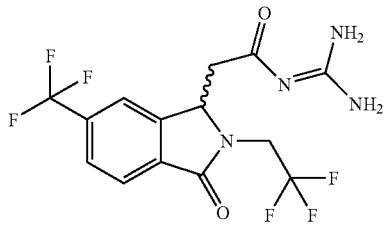

The title compounds of example 46a and 46b were prepared by chromatography of 0.56 g of example 21 on Chiralcel OD, 250×50 mm, 20 μm using HEP/EtOH/MeOH 50:5:2 at a flow of 100 ml/minute separated the two enantiomers:

EXAMPLE 46a

Yield 120 mg of an amorphous solid.

Analytical HPLC on Chiralcel OD/20 250×4.6 using HEP/EtOH/MeOH 50:5:2 at a flow of 1.0 ml/minute: RT=9.620 minutes

EXAMPLE 46b

Yield 190 mg of an amorphous solid.

Analytical HPLC on Chiralcel OD/20 250×4.6 using HEP/EtOH/MeOH 50:5:2 at a flow of 1.0 ml/minute: RT=11.899 minutes

EXAMPLE 47

(R)-N-{2-[3-Oxo-2-(2,2,2-trifluoro-ethyl)-5-trifluoromethyl-2,3-dihydro-1H-isoindol-1-yl]-acetyl}-guanidine and (S)-N-{2-[3-Oxo-2-(2,2,2-trifluoro-ethyl)-5-trifluoromethyl-2,3-dihydro-1H-isoindol-1-yl]-acetyl}-guanidine

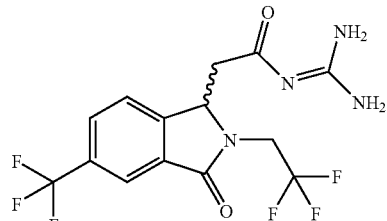

The title compounds were synthesized analogously to example 21 using [3-Oxo-2(2,2,2-trifluoro-ethyl)-5-trifluoromethyl-2,3-dihydro-1H-isoindol-1-yl]-acetic acid ethyl ester (example 21) as the starting material (R$_f$(EA/MeOH 3:1)=0.40, MS (ES+): 383 (M+1)$^+$).

Chromatography on Chiralpac AD-H, 250×20 mm, 10 μm using ACN/HEP/i-PrOH 50:5:2+0.3% DEA at a flow of 3 to 6 ml/minute separated the enantiomers:

EXAMPLE 47a

Yield 24 mg of an amorphous solid.

Analytical HPLC on Chiralcel OD/20 250×4.6 using ACN/HEP/i-PrOH 50:5:2+0.3% DEA at a flow of 1.0 ml/minute: RT=4.236 minutes

EXAMPLE 47b

Yield 31 mg of an amorphous solid.

Analytical HPLC on Chiralcel OD/20 250×4.6 using ACN/HEP/i-PrOH 50:5:2+0.3% DEA at a flow of 1.0 ml/minute: RT=6.296 minutes

EXAMPLE 48

N-{2-[3-Oxo-2-(2,2,2-trifluoro-ethyl)-6-trifluoromethyl-2,3-dihydro-1H-isoindol-1-yl]-acetyl}-guanidine hydrogen fumarate, 1.5 g of the title compound of example 46b and 0.45 g fumaric acid were dissolved together using acetone/ACN 1:1+1 ml of water and stirred for 15 minutes at ambient temperature. The solvents were removed in vacuo, the residue was suspended using 50 ml of CH$_2$Cl$_2$ and the product filtered off. The product was dried in vacuo to yield 1.65 g of white crystals, m.p. 202° C.

The title compounds of example 49 and 50 were prepared by chromatography of 600 mg of example 26 on Chiralpac AD, 250×50 mm, 20 μm using ACN/HEP/i-PrOH 50:4:3+0.3% DEA at a flow of 100 ml/minute:

EXAMPLE 49

(R)-N-[2-(6-chloro-3-oxo-2-(3,3,3-trifluoropropyl)-2,3-dihydro-1H-isoindol-1-yl]-acetyl}-guanidine and (S)-N-[2-(6-chloro-3-oxo-2-(3,3,3-trifluoropropyl)-2,3-dihydro-1H-isoindol-1-yl]-acetyl}-guanidine

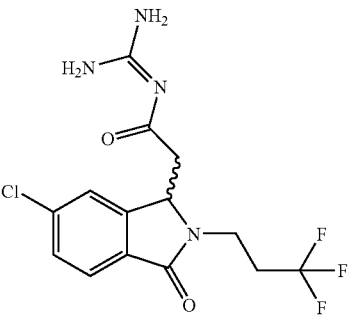

EXAMPLE 49a

Yield 90 mg of an amorphous solid.

Analytical HPLC on Chiralpac AD/H 250×4.6 using ACN/HEP/i-PrOH 50:3:4+0.3% DEA at a flow of 1.0 ml/minute: RT=6.092 minutes

EXAMPLE 49b

Yield 110 mg of an amorphous solid.

Analytical HPLC on Chiralpac AD/H 250×4.6 using ACN/HEP/i-PrOH 50:3:4+0.3% DEA at a flow of 1.0 ml/minute: RT=11.876 minutes

EXAMPLE 50

(R)-N-[2-(5-chloro-3-oxo-2-(3,3,3-trifluoropropyl)-2,3-dihydro-1H-isoindol-1-yl]-acetyl}-guanidine and (S)-N-[2-(5-chloro-3-oxo-2-(3,3,3-trifluoropropyl)-2,3-dihydro-1H-isoindol-1-yl]-acetyl}-guanidine

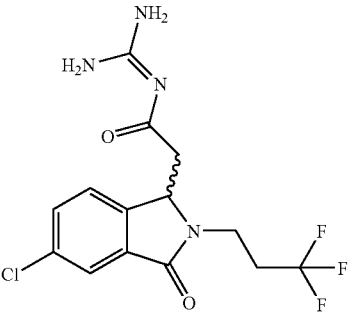

EXAMPLE 50a

Yield 35 mg of an amorphous solid.

Analytical HPLC on Chiralpac AD/H 250×4.6 using ACN/HEP/i-PrOH 50:3:4+0.3% DEA at a flow of 1.0 ml/minute: RT=5.663 minutes

EXAMPLE 50b

Yield 51 mg of an amorphous solid.

Analytical HPLC on Chiralpac AD/H 250×4.6 using ACN/HEP/i-PrOH 50:3:4+0.3% DEA at a flow of 1.0 ml/minute: RT=23.673 minutes The title compounds of example 51 and 52 were prepared by chromatography of 280 mg of example 27 on Chiralpac AD, 250×50 mm, 20 μm using ACN/HEP/i-PrOH 50:4:3+0.3% DEA at a flow of 50 ml/minute:

EXAMPLE 51

(R)-N-{2-[3-Oxo-6-trifluoromethyl-2-(3,3,3-trifluoro-propyl)-2,3-dihydro-1H-isoindol-1-yl]-acetyl}-guanidine and (S)-N-{2-[3-Oxo-6-trifluoromethyl-2-(3,3,3-trifluoro-propyl)-2,3-dihydro-1H-isoindol-1-yl]-acetyl}-guanidine

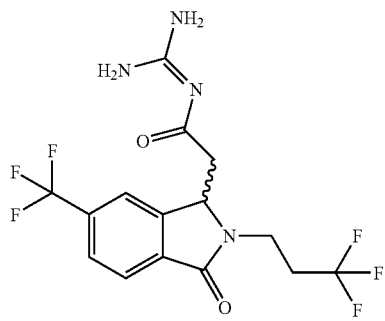

EXAMPLE 51a

Yield 29 mg of an amorphous solid.

Analytical HPLC on Chiralpac AD/H 250×4.6 using ACN/HEP/i-PrOH 50:5:2+0.3% DEA at a flow of 1.0 ml/minute: RT=4.037 minutes

EXAMPLE 51b

Yield 27 mg of an amorphous solid.

Analytical HPLC on Chiralpac AD/H 250×4.6 using ACN/HEP/i-PrOH 50:5:2+0.3% DEA at a flow of 1.0 ml/minute: RT=5.083 minutes

EXAMPLE 52

(R)-N-{2-[3-Oxo-5-trifluoromethyl-2-(3,3,3-trifluoro-propyl)-2,3-dihydro-1H-isoindol-1-yl]-acetyl}-guanidine and (S)-N-{2-[3-Oxo-5-trifluoromethyl-2-(3,3,3-trifluoro-propyl )-2,3-dihydro-1H-isoindol-1-yl]-acetyl}-guanidine

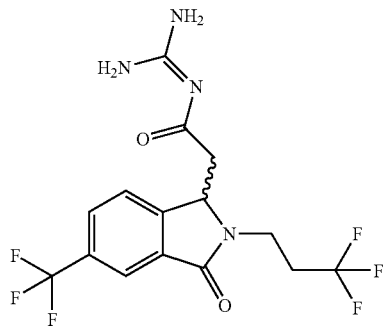

EXAMPLE 52a

Yield 15 mg of an amorphous solid.

Analytical HPLC on Chiralpac AD/H 250×4.6 using ACN/HEP/i-PrOH 50:5:2+0.3% DEA at a flow of 1.0 ml/minute: RT=4.497 minutes

EXAMPLE 52b

Yield 68 mg of an amorphous solid.

Analytical HPLC on Chiralpac AD/H 250×4.6 using ACN/HEP/i-PrOH 50:5:2+0.3% DEA at a flow of 1.0 ml/minute: RT=8.228 minutes The title compounds of example 53 and 54 were prepared by chromatography of 300 mg of example 28 on Chiralpac AD, 250×50 mm, 20 μm using ACN/HEP/i-PrOH 50:5:2+0.3% DEA at a flow of 100 ml/minute:

EXAMPLE 53

(R)-N-{2-[6-Chloro-3-oxo-2-(4,4,4-trifluoro-butyl)-2,3-dihydro-1H-isoindol-1-yl]-acetyl}-guanidine and (S)-N-{2-[6-Chloro-3-oxo-2-(4,4,4-trifluoro-butyl)-2,3-dihydro-1H-isoindol-1-yl]-acetyl}-guanidine

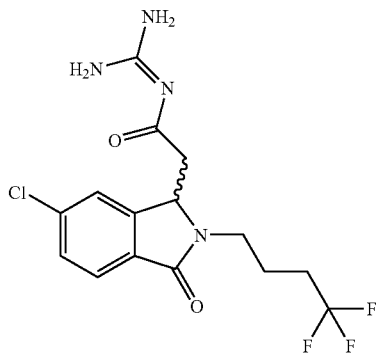

EXAMPLE 53a

Yield 76 mg of an amorphous solid.

Analytical HPLC on Chiralpac AD/H 250×4.6 using ACN/HEP/i-PrOH 50:4:3+0.3% DEA at a flow of 1.0 ml/minute: RT=5.761 minutes

EXAMPLE 53b

Yield 34 mg of an amorphous solid.

Analytical HPLC on Chiralpac AD/H 250×4.6 using ACN/HEP/i-PrOH 50:4:3+0.3% DEA at a flow of 1.0 ml/minute: RT=7.079 minutes

EXAMPLE 54

(R)-N-{2-[5-Chloro-3-oxo-2-(4,4,4-trifluoro-butyl)-2,3-dihydro-1H-isoindol-1-yl]-acetyl}-guanidine and (S)-N-{2-[5-Chloro-3-oxo-2-(4,4,4-trifluoro-butyl)-2,3-dihydro-1H-isoindol-1-yl]-acetyl}-guanidine

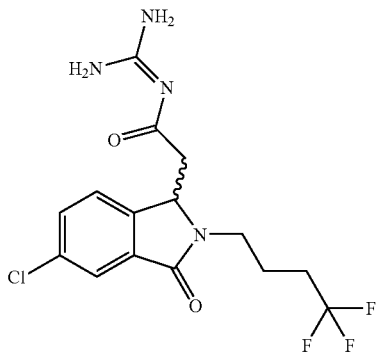

EXAMPLE 54a

Yield 34 mg of an amorphous solid.

Analytical HPLC on Chiralpac AD/H 250×4.6 using ACN/HEP/i-PrOH 50:4:3+0.3% DEA at a flow of 1.0 ml/minute: RT=5.421 minutes

EXAMPLE 54b

Yield 72 mg of an amorphous solid.

Analytical HPLC on Chiralpac AD/H 250×4.6 using ACN/HEP/i-PrOH 50:4:3+0.3% DEA at a flow of 1.0 ml/minute: RT=9.865 minutes The title compounds of example 55 and 56 were prepared by chromatography of 330 mg of example 24 on Chiralpac AD, 250×50 mm, 20 μm using ACN/HEP/i-PrOH 50:5:2+0.3% DEA at a flow of 100 ml/minute:

EXAMPLE 55

(R)-N-[2-(6-Chloro-2-cyclopropylmethyl-3-oxo-2,3-dihydro-1H-isoindol-1-yl)-acetyl]-guanidine and (S)-N-[2-(6-Chloro-2-cyclopropylmethyl-3-oxo-2,3-dihydro-1H-isoindol-1-yl)-acetyl]-guanidine

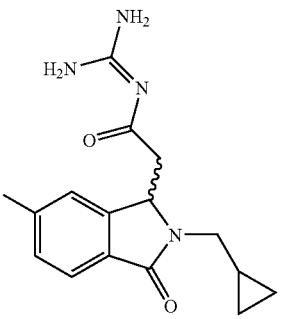

EXAMPLE 55a

Yield 16 mg of an amorphous solid.

Analytical HPLC on Chiralpac AD/H 250×4.6 using ACN/HEP/i-PrOH 50:5:2+0.3% DEA at a flow of 1.0 ml/minute: RT=7.330 minutes

EXAMPLE 55b

Yield 46 mg of an amorphous solid.

Analytical HPLC on Chiralpac AD/H 250×4.6 using ACN/HEP/i-PrOH 50:5:2+0.3% DEA at a flow of 1.0 ml/minute: RT=11.908 minutes

EXAMPLE 56

(R)-N-[2-(5-Chloro-2-cyclopropylmethyl-3-oxo-2,3-dihydro-1H-isoindol-1-yl)-acetyl]-guanidine and (S)-N-[2-(5-Chloro-2-cyclopropylmethyl-3-oxo-2,3-dihydro-1H-isoindol-1-yl)-acetyl]-guanidine

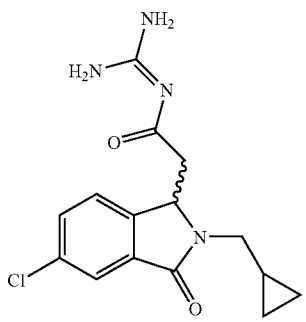

EXAMPLE 56a

Yield 32 mg of an amorphous solid.

Analytical HPLC on Chiralpac AD/H 250×4.6 using ACN/HEP/i-PrOH 50:5:2+0.3% DEA at a flow of 1.0 ml/minute: RT=6.821 minutes

EXAMPLE 56b

Yield 47 mg of an amorphous solid.

Analytical HPLC on Chiralpac AD/H 250×4.6 using ACN/HEP/i-PrOH 50:5:2+0.3% DEA at a flow of 1.0 ml/minute: RT=27.738 minutes NHE Inhibition Method The NHE inhibitory activities ($IC_{50}$ values) of the compounds according to the invention were determined by a FLIPR test.

The test is performed in the FLIPR (Fluorescent Imaging Plate Reader) equipped with clear-bottomed and black-walled 96-well microtitration plates. The transfected cell lines expressing the various NHE subtypes (the parental cell line LAP-1 shows no endogenous NHE activity as a result of mutagenesis and subsequent selection) are seeded the preceding day at a density of ~25 000 cells/well.

The growth medium for the transfected cells (Iscove +10% foetal calf serum) also comprises G418 as selection antibiotic to ensure the presence of transfected sequences.

The actual test begins by eliminating the growth medium and adding 100 μl of loading buffer per well (5 μM of BCECF-AM [2',7'-bis(2-carboxyethyl)-5-(6)-carboxyfluoresceine acetoxymethyl ester] in 20 mM of $NH_4Cl$, 115 mM of choline chloride, 1 mM of $CaCl_2$, 5 mM of KCl, 20 mM of HEPES and 5 mM of glucose; pH 7.4 (adjusted with KOH). The cells are then incubated for 20 minutes at 37° C. This incubation results in the loading of the fluorescent dye into the cells, the fluorescence intensity of which depends on the $pH_i$, and on the $NH_4Cl$, which results in a slight basification of the cells.

The precursor BCECF-AM, a non-fluorescent dye, is, as an ester, capable of crossing the membrane. The actual dye, which is incapable of crossing the membrane, is released inside the cell by esterases.

After this 20-minute incubation, the loading buffer, which comprises $NH_4Cl$ and free BCECF-AM, is removed by washing three times in the cell washing device (Tecan Columbus), each wash being performed with 400 μl of washing buffer (133.8 mM of choline chloride, 4.7 mM of KCl, 1.25 mM of $MgCl_2$, 1.25 mM of CaCl2, 0.97 mM of $K_2HPO_4$, 0.23 mM of $KH_2PO_4$, 5 mM of HEPES and 5 mM of glucose; pH 7.4 (adjusted with KOH)). The residual volume remaining in the wells is 90 μl (possibly between 50 and 125 μl). This washing step removes the free BCECF-AM and results in an intracellular acidification ($pH_i$ of 6.3–6.4) due to the removal of the external ammonium ions.

As the equilibrium of the intracellular ammonium with the aqueous ammonia and the protons, by removal of the extracellular ammonium and by the subsequent immediate crossing of the aqueous ammonia across the cell membrane, is disrupted, the washing process results in intracellular protons remaining, which is the cause of the intracellular acidification. This acidification can result finally in the death of the cells if it lasts long enough. It is important here for the washing buffer to be free of sodium (<1 mM), otherwise the extracellular sodium ions would result in an immediate increase in the $pH_i$ on account of the activity of the cloned NHE isoforms. It is also important for all the buffers used (loading buffer, washing buffer and regeneration buffer) not to contain any $HCO_3$-ions, otherwise the presence of bicarbonate would result in the activation of bicarbonate-dependent systems that disrupt the $pH_i$ regulation, which systems are contained in the LAP-1 parental cell line.

The microtiter plates containing acidified cells are then transferred (up to 20 minutes after the acidification) to the FLIPR. In the FLIPR, the intracellular fluorescent dye is activated with light of a wavelength of 488 nm, which is generated by an argon laser, and the measuring parameters (laser power, illumination time and diaphragm of the CDD camera integrated into the FLIPR) are chosen such that the average value of the fluorescent signal per well is between 30,000 and 35,000 relative fluorescence units.

The actual measurement in the FLIPR starts with a photograph being taken by the CCD camera every two seconds under software control. After 10 seconds, the increase in the intracellular pH is initiated by adding 90 μl of regeneration buffer (133.8 mM of NaCl, 4.7 mM of KCl, 1.25 mM of $MgCl_2$, 1.25 mM of $CaCl_2$, 0.97 mM of $K_2HPO_4$, 0.23 mM of $KH_2PO_4$, 10 mM of HEPES and 5 mM of glucose; pH 7.4 (adjusted with NaOH)) using a 96-well pipette device incorporated into the FLIPR. Some wells, to which is added pure regeneration buffer, serve as positive controls (100% NHE activity). The negative controls (0% NHE activity) contain washing buffer. Regeneration buffer with twice the concentration of test substance is added to all the other wells. Measurement in the FLIPR terminates after 60 measurements (two minutes).

The experimental data allow the NHE activities to be calculated for each concentration of test substance and, from these, the $IC_{50}$ values of the substances. For the NHE-1 subtype the following results are obtained.

| example No. | IC50 (NHE1)/nM |
| --- | --- |
| 1 | 74 |
| 2 | 59 |

-continued

| example No. | IC50 (NHE1)/nM |
|---|---|
| 3 | 50 |
| 4 | 57 |
| 5 | 92 |
| 6 | 211 |
| 7 | 116 |
| 8 | 63 |
| 9 | 156 |
| 10 | 15 |
| 11 | 11 |
| 12 | 7 |
| 13 | 22 |
| 14 | 102 |
| 15 | 16 |
| 16 | 251 |
| 17 | 43 |
| 18 | 26 |
| 19 | 11 |
| 20 | 18 |
| 21 | 4.9 |
| 22 | 100 |
| 23 | 35 |
| 24 | 7.7 |
| 25 | 10 |
| 26 | 8.6 |
| 27 | 22 |
| 28 | 88 |
| 29 | 2344 |
| 30 | 450 |
| (as hydrochlorides) | 760 |
| 30 | 210 |
| (as trifluoroacetates) | 430 |
| 31 | 300 |
| (as hydrochlorides) | 1400 |
| 31 | 440 |
| (as trifluoroacetates) | 190 |
| 32 | 130 |
| (as hydrochlorides) | 1400 |
| 32 | 170 |
| (as trifluoroacetates) | 150 |
| 33 | 3600 |
|  | 4700 |
| 34 | 25 |
| 35 | 38 |
| 36 | 31 |
| 36a | 524 |
| 36b | 6 |
| 37 | 188 |
| 38a | 249 |
| 38b | 5 |
| 40 | 29 |
| 40a | 263 |
| 40b | 63 |
| 41a | 3 |
| 41b | 41 |
| 41c | 19 |
| 42 | 18 |
| 42a | 66 |
| 42b | 3 |
| 43 | 30 |
| 43a | 53 |
| 43b | 442 |
| 44a | 2 |
| 44b | 13 |
| 44c | 260 |
| 45 | 212 |
| 46a | 19 |
| 46b | 0.2 |
| 47a | 70 |
| 47b | 5794 |
| 48 | 0.2 |
| 49a | 1 |
| 49b | 13 |
| 50a | 9 |
| 50b | 6 |
| 51a | 6 |
| 51b | 171 |
| 52a | 50 |
| 52b | 671 |
| 53a | 83 |
| 53b | 16 |
| 54a | 944 |
| 54b | 48 |
| 55a | 2 |
| 55b | 20 |
| 56a | 28 |
| 56b | 18 |

The invention relates also to the use of isoindolone derivatives of the formula I and/or pharmaceutically acceptable salts thereof for the preparation of medicaments and pharmaceutical compositions as inhibitors of the NHE. Claimed is a medicine for human, veterinary or phytoprotective use, comprising an effective amount of a compound of the formula I and/or the pharmaceutically acceptable salts thereof, together with pharmaceutically acceptable carriers and additives, alone or in combination with other active pharmaceutical ingredients or medicaments.

The pharmaceutical compositions according to the invention consist of a compound of the formula I and/or the pharmaceutically acceptable salt thereof, in pure form or in the form of a composition in which it is combined with any other pharmaceutically compatible product, which may be inert or physiologically active. The medicaments according to the invention can be administered, for example, orally, parenterally, intravenously, rectally, transdermally, topically or by inhalation. The medicaments generally comprise active ingredients of the formula I and/or pharmaceutically acceptable salts thereof in an amount of from 0.001 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a pharmaceutical formulation for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

Tablets, pills, powders (gelatin capsules or cachets) or granules can be used as solid compositions for oral administration. In these compositions, the active principle according to the invention is mixed with one or more inert diluents, such as starch, cellulose, sucrose, lactose or silica, under a stream of argon. These compositions may also comprise substances other than diluents, for example one or more lubricants, such as magnesium stearate or talc, a colorant, a coating (dragees) or a varnish.

Pharmaceutically acceptable solutions, suspensions, emulsions, syrups and elixirs comprising inert diluents, such as water, ethanol, glycerol, plant oils or liquid paraffin can be used as liquid compositions for oral administration. These compositions may comprise substances other than diluents, for example wetting products, sweeteners, thickeners, flavorings or stabilizers.

The sterile compositions for parenteral administration can preferably be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also contain adjuvants, in particular wetting agents, tonicity agents, emulsifiers, dispersants and stabilizers. The sterilization can be performed in several ways, for example by aseptic filtration, by incorporating sterilizing agents into the composition, by irradiation or by heating. They can also be prepared in the form of sterile solid compositions that may be dissolved at the time of use in sterile water or any other injectable sterile medium.

The compositions for rectal administration are suppositories or rectal capsules that contain, besides the active product, excipients, such as cocoa butter, semi-synthetic glycerides or polyethylene glycols.

The compositions for topical administration can be, for example, creams, lotions, eye drops, mouthwashes, nasal drops or aerosols.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or the pharmaceutically acceptable salts thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation contains, for example, the active ingredient in a concentration of about 0.1 to 10, in particular of about 0.3 to 3% by weight.

The dosage of the active ingredient of the formula I to be administered, and the frequency of administration, depend on the desired effect, the potency and duration of action of the compounds used; additionally also on the nature and severity of the disorder to be treated and on the sex, age, weight and individual responsiveness of the mammal to be treated. In general, the doctor will determine the appropriate dosage as a function of the age and weight and all the other factors specific to the individual to be treated.

On average, the daily dose of a compound of the formula I and/or the pharmaceutically acceptable salts thereof for a patient weighing about 75 kg is at least 0.001 mg/kg, preferably 1 mg/kg, to a maximum of 1000 mg/kg, preferably 100 mg/kg, of body weight. For acute episodes of the disorder, for example immediately after suffering a myocardial infarction, higher and, in particular, more frequent dosages may also be necessary, e.g. up to 4 single doses a day. Up to 2000 mg a day may be necessary, in particular on i.v. administration, for example for a patient with infarction in the intensive care unit, and the compounds of the invention can be administered by infusion.

The following examples illustrate compositions according to the invention:

EXAMPLE A

Gel capsules containing a 50 mg dose of active product, having the composition below, are prepared according to the usual technique:

| | |
|---|---|
| Compound of the formula I | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets containing a 50 mg dose of active product, having the composition below, are prepared according to the usual technique:

| | |
|---|---|
| Compound of the formula I | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcelluse, glycerol and titanium oxide (72/3.5/24.5) qs 1 finished film-coated tablet weighing 245 mg | |

EXAMPLE C

An injectable solution comprising 10 mg of active product, having the composition below, is prepared:

| | |
|---|---|
| Compound of the formula I | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water | qs 4 ml |

What is claimed is:
1. A compound of formula I

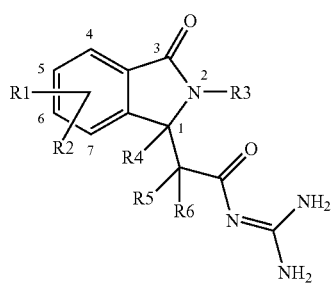

in which
R1 and R2
are, independently of one another, hydrogen, alkyl having 1, 2, 3 or 4 carbon atoms, alkenyl having 2, 3, 4, 5 or 6 carbon atoms, alkynyl having 2, 3, 4, 5 or 6 carbon atoms, aryl, heteroaryl, F, Cl, Br, I, $NO_2$, $NH_2$, alkylamino having 1, 2, 3 or carbon atoms, NRaRb, alkylcarbonylamino having 1, 2, 3 or 4 carbon atoms, OH, alkoxy having 1, 2, 3 or 4 carbon atoms, $S(O)_nR7$, $CO_2H$, alkoxycaxbonyl having 1, 2, 3 or carbon atoms, alkylcarbonyl having 1, 2, 3 or 4 carbon atoms, $CONH_2$, CONRaRb, CN, polyfluoroalkyl having 1, 2, 3 or 4 carbon atoms, polyfluoroalkoxy having 1, 2 or 3 carbon atoms or $SO_3H$;
R1 and R2 themselves optionally being substituted by a linear or branched alkyl group having 1, 2, 3 or 4 carbon atoms;
wherein
n is zero, 1 or 2;
R3 is hydrogen, aryl, heteroaryl, a group of the Alk-R8 type or cycloalkyl having 3, 4, 5, 6, 7 or 8 carbon atoms,
in which cycloalkyl is optionally substituted by one or more substituents selected from the group F, Cl, Br or I,
Alk is alkyl having of 1, 2, 3, 4 or 5 carbon atoms in a line or branched chain,
R8 is hydrogen, cycloalkyl having 3, 4, 5, 6, 7 or 8 carbon atoms, polyfluoroaflryl having 1, 2, 3 or 4 carbon atoms, aryl, heteroaryl, OH, alkoxy having 1, 2, 3 or 4 carbon atoms, $CO_2H$, $CONH_2$, CONRaRb, $NH_2$, alkylamino having 1, 2, 3 or 4 carbon atoms or NRaRb;
R4, R5 and R6
are, independently of one another, hydrogen or a linear or branched alkyl having 1, 2, 3 or 4 carbon atoms;
R7 is a linear or branched alkyl having 1, 2, 3 or 4 carbon atoms; and
Ra and Rb
are, independently of one another, defined as R7, or alternatively Ra and Rb form, together with the nitrogen atom to which they are attached, a 5- or 6-membered heterocycle optionally containing another hetero atom chosen from O, S or N;
and a racemic mixture, enantiomer and diastereomer thereof or a mixture thereof, a tautomer thereof or a pharmaceutically acceptable salt thereof.
2. A compound of formula I as claimed in claim 1, in which R1 and R2
are, independently of one another, hydrogen, alkyl having 1, 2, 3 or 4 carbon atoms, F, Cl, Br, I, $NH_2$, alkylamino having 1, 2, 3 or 4 carbon atoms, NRaRb, alkylcarbonylamino having 1, 2, 3 or 4 carbon atoms, OH, alkoxy having 1, 2, 3 or 4 carbon atoms, $CO_2H$, alkoxycarbonyl having 1, 2, 3 or 4 carbon atoms, polyfluoroalkyl having 1, 2, 3 or 4 carbon atoms, polyfluoroalkoxy having 1, 2 or 3 carbon atoms or $SO_3H$ R1 and R2 themselves optionally being substituted by a linear or branched alkyl group having 1, 2, 3 or 4 carbon atoms;
R3 is a group of the Alk-R8 type or cycloalkyl having 3, 4, 5, 6, 7 or 8 carbon atoms,
in which cycloalkyL is optionally substituted by one or mare substituents selected from the group F, Cl or Br,
Alk is an alkyl having 1, 2, 3, 4 or 5 carbon atoms in a linear branched chain,
R8 is hydrogen, cycloalkyl having 3, 4, 5, 6, 7 or 8 carbon atoms, polyfluoroalkyl having 1, 2, 3 or 4 carbon atoms, aryl or heteroaryl;
R4, R5 and R6
are, independently of one another, hydrogen or a linear or branched alkyl having 1, 2, 3 or 4 carbon atoms; and
Ra and Rb
are, independently of one another, a linear or branched alkyl having 1, 3 or 4 carbon atoms, or Ra and Rb form, together with the nitrogen atom to which they are attached, a 5- or 6-membered heterocycle optionally containing another hetero atom chosen from O, S and N;
and a racemic mixture, enantiomer and diastereomer thereof or a mixture thereof, a tautomer thereof or a pharmaceutically acceptable salt thereof.
3. A compound of formula I claimed as in claim 2, in which
R1 and R2
are, independently of one another, hydrogen, alkyl having 1, 2, 3 or 4 carbon atoms, F, Cl, Br, I, OH, alkoxy having 1, 2, 3 or 4 carbon atoms, polyfluoroalkyl having 1, 2, 3 or 4 carbon atoms or polyfluoroalkoxy having 1, 2 or 3 carbon atoms, R1 and R2 themselves optionally being substituted by a linear or branched alkyl having 1, 2, 3 or 4 carbon atoms;
R3 is a group of the Alk-R8 type or cycloalkyl having 3, 4, 5, 6, 7 or 8 carbons atoms,
in which cycloalkyl is optionally substituted by one or more substituents selected from the group F or Cl,
Alk is an alkyl having 1, 2, 3, 4 or 5 carbon atoms in a linear or branched chain,
R8 is hydrogen, cycloalkyl having 3, 4, 5, 6, 7 or 8 carbon atoms or polyfluoroalkyl having 1, 2, 3 or 4 carbon atoms; and
R4, R5 and R6
are, independently of one another, hydrogen or a linear or branched alkly having 1, 2, 3 or 4 carbon atoms;
and a racemic mixture, enantiomer and diastercomer thereof or a mixture thereof, a tautomer thereof or a pharmaceutically acceptable salt thereof.
4. A compound as claimed in claim 1, which is chosen from:
N-[2-(2-isobutyl-3-oxo-2,3-dihydro-1H-isoindol-1-yl)-2-methylpropionyl]guanidine,
N-[2-(2-cyclopropylmethyl-3-oxo-2,3-dihydro-1H-isoindol-1-yl)-2-methylpropionyl]guanidine,
N-[(3-oxo-2-(3,3,3-trifluoropropyl)-2,3-dihydro-1H-isoindol-1-yl)acetyl]guanidine, N-[(3-oxo-2-(4,4,4-trifluorobutyl)-2,3-dihydro-1H-isoindol-1-yl)acetyl]guanidine,
N-[(3-oxo-2,3-dihydro-1H-isoindol-1-yl)acetyl]guanidine,
N-[(2-isobutyl-7-methyl-3-oxo-2,3-dihydro-1H-isoindol-1-yl)acetyl]guanidine,
N-[(4-amino-2-isobutyl-3-oxo-2,3-dihydro-1H-isoindol-1-yl)acetyl]guanidine,
N-[(5-amino-2-isobutyl-3-oxo-2,3-dihydro-1H-isoindol-1-yl)acetyl]guanidine,
N-[(6-amino-2-isobutyl-3-oxo-2,3-dihydro-1H-isoindol-1-yl)acetyl]guanidine,
N-[(7-amino-2-isobutyl-3-oxo-2,3-dihydro-1H-isoindol-1-yl)acetyl]guanidine,
N-[(4-hydroxy-2-isobutyl-3-oxo-2,3-dihydro-1H-isoindol-1-yl)acetyl]guanidine,
N-[(5-hydroxy-2-isobutyl-3-oxo-2,3-dihydro-1H-isoindol-1-yl)acetyl]guanidine,
N-[(6-hydroxy-2-isobutyl-3-oxo-2,3-dihydro-1H-isoindol-1-yl)acetyl]guanidine,
N-[(7-hydroxy-2-isobutyl-3-oxo-2,3-dihydro-1H-isoindol-1-yl)acetyl]guanidine,
N-[(4,7-dichloro-2-isobutyl-3-oxo-2,3-dihydro-1H-isoindol-1-yl)acetyl]guanidine,
N-[(4-fluoro-2-isobutyl-3-oxo-2,3-dihydro-1H-isoindol-1-yl)acetyl]guanidine,
N-[(5-fluoro-2-isobutyl-3-oxo-2,3-dihydro-1H-isoindol-1-yl)acetyl]guanidine,
N-[(6-fluoro-2-isobutyl-3-oxo-2,3-dihydro-1H-isoindol-1-yl)acetyl]guanidine,
N-[(4,5-difluoro-2-isobutyl-3-oxo-2,3-dihydro-1H-isoindol-1-yl)acetyl]guanidine,
N-[(6,7-difluoro-2-isobutyl-3-oxo-2,3-dihydro-1H-isoindol-1-yl)acetyl]guanidine,
N-[(4-carboxy-2-isobutyl-3-oxo-2,3-dihydro-1H-isoindol-1-yl)acetyl]guanidine,
N-[(5-carboxy-2-isobutyl-3-oxo-2,3-dihydro-1H-isoindol-1-yl)acetyl]guanidine,
N-[(6-carboxy-2-isobutyl-3-oxo-2,3-dihydro-1H-isoindol-1-yl)acetyl]guanidine,
N-[(7-carboxy-2-isobutyl-3-oxo-2,3-dihydro-1H-isoindol-1-yl)acetyl]guanidine, and
N-[(2-isobutyl-1-methyl-3-oxo-2,3-dihydro-1H-isoindol-1-yl)acetyl]guanidine, and racemic mixtures, enantiomers and diastereomers thereof, and mixtures thereof, tautomers thereof and pharmaceutically acceptable salts thereof.

5. A compound as claimed in claim 1, which is chosen from:

N-[(2-methyl-3-oxo-2,3-dihydro-1H-isoindol-1-yl)acetyl]guanidine,
N-[(2-ethyl-3-oxo-2,3-dihydro-1H-isoindol-1-yl)acetyl]guanidine,
N-[(3-oxo-2-propyl-2,3-dihydro-1H-isoindol-1-yl)acetyl]guanidine,
N-[2-(3-oxo-2-propyl-2,3-dihydro-1H-isoindol-1-yl)propionyl]guanidine,
N-[(2-isopropyl-3-oxo-2,3-dihydro-1H-isoindol-1-yl)acetyl]guanidine,
N-[2-(2-butyl-3-oxo-2,3-dihydro-1H-isoindol-1-yl)propionyl]guanidine,
N-[(2-isobutyl-3-oxo-2,3-dihydro-1H-isoindol-1-yl)acetyl]guanidine,
N-[2-(2-isobutyl-3-oxo-2,3-dihydro-1H-isoindol-1-yl)propionyl]guanidine,
N-[(2-cyclopropylmethyl-3-oxo-2,3-dihydro-1H-isoindol-1-yl)acetyl]guanidine,
N-[(2-benzyl-3-oxo-2,3-dihydro-1H-isoindol-1-yl)acetyl]guanidine,
N-[(3-oxo-2-(2,2,2-trifluoroethyl)-2,3-dihydro-1H-isoindol-1-yl)acetyl]guanidine,
N-[(2-isobutyl-4-methyl-3-oxo-2,3-dihydro-1H-isoindol-1-yl)acetyl]guanidine,
N-[(2-isobutyl-5-methyl-3-oxo-2,3-dihydro-1H-isoindol-1-yl)acetyl]guanidine,
N-[(2-isobutyl-6-methyl-3-oxo-2,3-dihydro-1H-isoindol-1-yl)acetyl]guanidine,
N-[(5-tert-butyl-2-isobutyl-3-oxo-2,3-dihydro-1H-isoindol-1-yl)acetyl]guanidine,
N-[(6-tert-butyl-2-isobutyl-3-oxo-2,3-dihydro-1H-isoindol-1-yl)acetyl]guanidine,
N-[(2-isobutyl-5-isopropoxy-3-oxo-2,3-dihydro-1H-isoindol-1-yl)acetyl]guanidine,
N-[(5-chloro-2-isobutyl-3-oxo-2,3-dihydro-1H-isoindol-1-yl)acetyl]guanidine,
N-[(6-chloro-2-isobutyl-3-oxo-2,3-dihydro-1H-isoindol-1-yl)acetyl]guanidine,
N-[(5-chloro-2-cyclopropylmethyl-3-oxo-2,3-dihydro-1H-isoindol-1-yl)acetyl]guanidine,
N-[(6-chloro-2-cyclopropylmethyl-3-oxo-2,3-dihydro-1H-isoindol-1-yl)acetyl]guanidine,
N-[(5-chloro-3-oxo-2-(2,2,2-trifluoroethyl)-2,3-dihydro-1H-isoindol-1-yl)acetyl]guanidine,
N-[(6-chloro-3-oxo-2-(2,2,2-trifluoroethyl)-2,3-dihydro-1H-isoindol-1-yl)acetyl]guanidine,
N-[(5-chloro-3-oxo-2-(3,3,3-trifluoropropyl)-2,3-dihydro-1H-isoindol-1-yl)acetyl]guanidine,
N-[(6-chloro-3-oxo-2-(3,3,3-trifluoropropyl)-2,3-dihydro-1H-isoindol-1-yl)acetyl]guanidine,
N-[(5-chloro-3-oxo-2-(4,4,4-trifluorobutyl)-2,3-dihydro-1H-isoindol-1-yl)acetyl]guanidine,
N-[(6-chloro-3-oxo-2-(4,4,4-trifluorobutyl)-2,3-dihydro-1H-isoindol-1-yl)acetyl]guanidine,
N-[(5,6-dichloro-2-isobutyl-3-oxo-2,3-dihydro-1H-isoindol-1-yl)acetyl]guanidine,
N-[(7-fluoro-2-isobutyl-3-oxo-2,3-dihydro-1H-isoindol-1-yl)acetyl]guanidine,
N-[(4,7-difluoro-2-isobutyl-3-oxo-2,3-dihydro-1H-isoindol-1-yl)acetyl]guanidine,
N-[(5-bromo-2-isobutyl-3-oxo-2,3-dihydro-1H-isoindol-1-yl)acetyl]guanidine,
N-[(6-bromo-2-isobutyl-3-oxo-2,3-dihydro-1H-isoindol-1-yl)acetyl]guanidine,
N-[(2-isobutyl-3-oxo-5-trifluoromethyl-2,3-dihydro-1H-isoindol-1-yl)acetyl]guanidine,
N-[(2-isobutyl-3-oxo-6-trifluoromethyl-2,3-dihydro-1H-isoindol-1-yl)acetyl]guanidine,
N-[(2-cyclopropylmethyl-3-oxo-5-trifluoromethyl-2,3-dihydro-1H-isoindol-1-yl)acetyl]guanidine,
N-[(2-cyclopropylmethyl-3-oxo-6-trifluoromethyl-2,3-dihydro-1H-isoindol-1-yl)acetyl]guanidine,
N-[(3-oxo-2-(2,2,2-trifluoroethyl)-6-trifluoromethyl-2,3-dihydro-1H-isoindol-1-yl)acetyl]-guanidine,
N-[(3-oxo-2-(2,2,2-trifluoro-ethyl)-5-trifluoromethyl-2,3-dihydro-1H-isoindol-1-yl)acetyl]-guanidine, N-[(3-oxo-5-trifluoromethyl-2-(3,3,3-trifluoropropyl)-2,
3-dihydro-1H-isoindol-1-yl)acetyl]-guanidine,
N-[(3-oxo-6-trifluoromethyl-2-(3,3,3-trifluoropropyl)-2,
3-dihydro-1H-isoindol-1-yl)acetyl]-guanidine,
N-[(3-oxo-2-(4,4,4-trifluorobutyl)-5-trifluoromethyl-2,3-
dihydro-1H-isoindol-1-yl)acetyl]-guanidine,
N-[(3-oxo-2-(4,4,4-trifluorobutyl)-6-trifluoromethyl-2,3-
dihydro-1H-isoindol-1-yl)acetyl]-guanidine,
[1-(2-guanidino-1-methyl-2-oxoethyl)-3-oxo-1,3-
dihydroisoindol-2-yl]acetic acid,
N-{2-[3-oxo-2-(2-pyrrolidin-1-ylethyl)-2,3-dihydro-1H-
isoindol-1-yl]propionyl}guanidine,
N-[2-(2-hydroxyethyl)-3-oxo-2,3-dihydro-1H-isoindol-
1-yl)propionyl]guanidine,
N-{2-[6-Methanesulfonyl-3-oxo-2-(2,2,2-trifluoro-
ethyl)-2,3-dihydro-1H-isoindol-1-yl]acetyl}-
guanidine,
N-[2-(2-cyclopropylmethyl-6-methanesulfonyl-3-oxo-2,
3-dihydro-1H-isoindol-1-yl)acetyl]-guanidinium,
N-{2-[5,6-difluoro-3-oxo-2-(3,3,3-trifluoro-propyl)-2,3-
dihydro-1H-isoindol-1-yl]-acetyl}guanidine,
N-{2-[5,6-dichloro-3-oxo-2-(3,3,3-trifluoro-propyl)-2,3-
dihydro-1H-isoindol-1-yl]-acetyl}guanidine,
N-[2-(5,6-dichloro-2-cyclopropylmethyl-3-oxo-2,3-
dihydro-1H-isoindol-1-yl)-acetyl]-guanidine,
N-[2-(5,6-dichloro-2-cyclopropyl-3-oxo-2,3-dihydro-1H-
isoindol-1-yl)-acetyl]-guanidine,
N-{2-[5,6-dichloro-3-oxo-2-(2,2,2-trifluoro-ethyl)-2,3-
dihydro-1H-isoindol-1-yl]-acetyl}-guanidine, and
N-{2-[5,6-difluoro-3-oxo-2-(2,2,2-trifluoro-ethyl)-2,3-
dihydro-1H-isoindol-1-yl]-acetyl}-guanidine,
and racemic mixtures, enantiomers and diastereomers thereof, tautomers thereof and pharmaceutically acceptable salts thereof.

6. A compound as claimed in claim 1, which is chosen from:
(R)-N-{2-[6-methanesulfonyl-3-oxo-2-(2,2,2-trifluoro-
ethyl)-2,3-dihydro-1H-isoindol-1-yl]-acetyl}-
guanidine,
(S)-N-{2-[6-methanesulfonyl-3-oxo-2-(2,2,2-trifluoro-
ethyl)-2,3-dihydro-1H-isoindol-1-yl]-acetyl}-
guanidine,
(R)-N-[2-(2-cyclopropylmethyl-3-oxo-6-trifluoromethyl-
2,3-dihydro-1H-isoindol-1-yl)-acetyl]-guanidine,
(S)-N-[2-(2-cyclopropylmethyl-3-oxo-6-trifluoromethyl-
2, 3-dihydro-1H-isoindol-1-yl)acetyl]-guanidine,
(R)-N-{2-[5,6-difluoro-3-oxo-2-(3,3,3-trifluoro-propyl)-
2,3-dihydro-1H-isoindol-1-yl]-acetyl}-guanidine,
(S)-N-{2-[5,6-difluoro-3-oxo-2-(3,3,3-trifluoro-propyl)-
2,3-dihydro-1H-isoindol-1-yl]-acetyl}-guanidine,
(R)-N-{2-[5,6-dichloro-3-oxo-2-(3,3,3-trifluoro-propyl)-
2,3-dihydro-1H-isoindol-1-yl]-acetyl}-guanidine,
(S)-N-{2-[5,6-dichloro-3-oxo-2-(3,3,3-trifluoro-propyl)-
2,3-dihydro-1H-isoindol-1-yl]-acetyl}-guanidine,
(R)-N-[2-(5,6-dichloro-2-cyclopropylmethyl-3-oxo-2,3-
dihydro-1H-isoindol-1-yl)-acetyl]-guanidine,
(S)-N-[2-(5,6-dichloro-2-cyclopropyl methyl-3-oxo-2,
3-dihydro-1H-isoindol-1-yl)-acetyl]-guanidine,
(R)-N-[2-(5,6-dichloro-2-cyclopropyl-3-oxo-2,3-
dihydro-1H-isoindol-1-yl)-acetyl]-guanidine,
(S)-N-[2-(5,6-dichloro-2-cyclopropyl-3-oxo-2,3-dihydro-
1H-isoindol-1-yl)-acetyl]-guanidine,
(R)-N-{2-[5,6-dichloro-3-oxo-2-(2,2,2-trifluoro-ethyl)-2,
3-dihydro-1H-isoindol-1-yl]-acetyl}-guanidine,
(S)-N-{2-[5,6-dichloro-3-oxo-2-(2,2,2-trifluoro-ethyl)-2,
3-dihydro-1H-isoindol-1-yl]-acetyl}-guanidine,
(R)-N-{2-[3-oxo-2-(2,2,2-trifluoro-ethyl)-6-
trifluoromethyl-2,3-dihydro-1H-isoindol-1-yl]-
acetyl}-guanidine,
(S)-N-{2-[3-oxo-2-(2,2,2-trifluoro-ethyl)-6-
trifluoromethyl-2,3-dihydro-1H-isoindol-1-yl]-
acetyl}-guanidine,
(R)-N-{2-[3-oxo-2-(2,2,2-trifluoro-ethyl)-5-
trifluoromethyl-2,3-dihydro-1H-isoindol-1-yl]-
acetyl}-guanidine,
(S)-N-{2-[3-oxo-2-(2,2,2-trifluoro-ethyl)-5-
trifluoromethyl-2,3-dihydro-1H-isoindol-1-yl]-
acetyl}-guanidine,
(R)-N-[2-(6-chloro-3-oxo-2-(3,3,3-trifluoropropyl)-2,3-
dihydro-1H-isoindol-1-yl)acetyl]-guanidine,
(S)-N-[2-(6-chloro-3-oxo-2-(3,3,3-trifluoropropyl)-2,3-
dihydro-1H-isoindol-1-yl)acetyl]-guanidine,
(R)-N-[2-(5-chloro-3-oxo-2-(3,3,3-trifluoropropyl)-2,3-
dihydro-1H-isoindol-1-yl)acetyl]-guanidine,
(S)-N-[2-(5-chloro-3-oxo-2-(3,3,3-trifluoropropyl)-2,3-
dihydro-1H-isoindol-1-yl)acetyl]-guanidine,
(R)-N-{2-[3-oxo-6-trifluoromethyl-2-(3,3,3-trifluoro-
propyl)-2,3-dihydro-1H-isoindol-1-yl]-acetyl}-
guanidine,
(S)-N-{2-[3-oxo-6-trifluoromethyl-2-(3,3,3-trifluoro-
propyl)-2,3-dihydro-1H-isoindol-1-yl]-acetyl}-
guanidine,
(R)-N-{2-[3-oxo-5-trifluoromethyl-2-(3,3,3-trifluoro-
propyl)-2,3-dihydro-1H-isoindol-1-yl]-acetyl}-
guanidine,
(S)-N-{2-[3-oxo-5-trifluoromethyl-2-(3,3,3-trifluoro-
propyl)-2,3-dihydro-1H-isoindol-1-yl]-acetyl}-
guanidine,
(R)-N-{2-[6-chloro-3-oxo-2-(4,4,4-trifluoro-butyl)-2,3-
dihydro-1H-isoindol-1-yl]-acetyl}-guanidine,
(S)-N-{2-[6-chloro-3-oxo-2-(4,4,4-trifluoro-butyl)-2,3-
dihydro-1H-isoindol-1-yl]-acetyl}-guanidine,
(R)-N-{2-[5-chloro-3-oxo-2-(4,4,4-trifluoro-butyl)-2,3-
dihydro-1H-isoindol-1-yl]-acetyl}-guanidine,
(S)-N-{2-[5-chloro-3-oxo-2-(4,4,4-trifluoro-butyl)-2,3-
dihydro-1H-isoindol-1-yl]-acetyl}-guanidine,
(R)-N-[2-(6-chloro-2-cyclopropylmethyl-3-oxo-2,3-
dihydro-1H-isoindol-1-yl)-acetyl]-guanidine,
(S)-N-[2-(6-chloro-2-cyclopropylmethyl-3-oxo-2,3-
dihydro-1H-isoindol-1-yl)-acetyl]-guanidine,
(R)-N-[2-(5-chloro-2-cyclopropylmethyl-3-oxo-2,3-
dihydro-1H-isoindol-1-yl)-acetyl]-guanidine, and
(S)-N-[2-(5-chloro-2-cyclopropylmethyl-3-oxo-2,3-
dihydro-1H-isoindol-1-yl)-acetyl]-guanidine.

7. A pharmaceutical composition for human, veterinary or phytoprotective use comprising an effective amount of a compound as claimed in claim 1, or a pharmaceutically acceptable salt thereof, together with pharmaceutically acceptable carrier or additive.

8. A pharmaceutical composition for human, veterinary or phytoprotective use comprising an effective amount of a compound as claimed in claim 1, or a pharmaceutically acceptable salt thereof, together with a pharmaceutically acceptable carrier or additive, and further in combination with another pharmacologically active ingredient or medicament.

9. A process for the preparation of a compound of formula I as defined in claim 1, in which R4 and R6 are hydrogen, the process comprising
- a) reacting a complex hydride with a phthalimide of formula II, R1, R2 and R3 having the same definition as in claim 1,

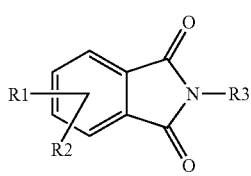

(II)

- b) reacting the product obtained with an alkoxycarbonylmethylenetriphenyl-phosphorane in toluene, or with a trialkyl phosphonoacetate and a base, and
- c) reacting the product obtained is reacted with guanidinium chloride and a base, or with guanidine in an alcohol having 1, 2, 3 or 4 carbon atoms.

10. A process for the preparation of a compound of formula I as defined in claim 1, in which R4 and R6 are hydrogen, the process comprising
- a) reacting a compound of formula II, R1 and R2 having the same definition as in claim 1, with an alkoxycarbonylmethylenetriphenyl-phosphorane in toluene, or with a trialkyl phosphonoacetate and a base,

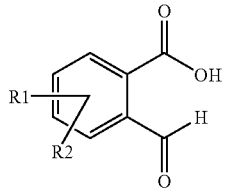

(III)

- b) reacting the product obtained with an amine of the formula R3NH$_2$, R3 having the same meaning as defined in claim 1, and a carbodiimide, and
- c) reacting the product obtained with guanidinium chloride and a base or with guanidine in an alcohol having 1, 2, 3 or 4 carbon atoms.

11. A process for the preparation of a compound of formula I as defined in claim 1, in which R4 is an alkyl and R6 is a hydrogen, the process comprising
- a) reacting a phthalimide of formula II as defined in claim 10 with an alkylmagnesium halide or an alkyllithium reagent in an ether,
- b) reacting the product obtained with an alkoxycarbonylmethylenetriphenyl phosphorane in toluene, or with 1-ethoxy-1-trimethylsiloxyethylene and a Lewis acid, and
- c) reacting the product obtained with guanidinium chloride and a base, or with guanidine in an alcohol having 1, 2, 3 or 4 carbon atoms.

12. A process for the preparation of a compound of formula I as defined in claim 1, in which R6 is an alkyl, the process comprising
- a) reacting a compound of formula IV, R1 to R5 having the same definitions as in claims 1, in the presence of lithium diisopropylamide, with an R6-Hal, where Hal is F, Cl, Br or I, and

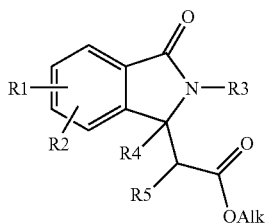

IV

- b) reacting the product obtained with guanidinium chloride and a base or with guanidine in an alcohol having 1, 2, 3 or 4 carbon atoms.

13. A compound as claimed in claim 1, which is chosen from : (R)-N-[2-(5-Chloro-2- cyclopropylmethyl-3oxo-2,3-dihydro-1H-isoiindol-1-yl)- acetyl]-guanidine and (S)-N-[2-(5-Chloro-2-cyclopropylmethyl-3oxo-2,3-dihydro-1H-isoindol-1-yl)-acetyl]-guanidine:

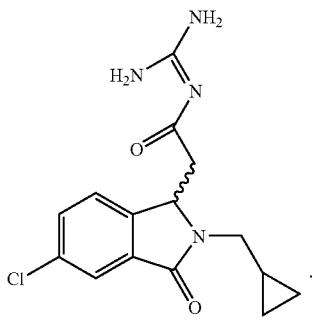

14. A compound as claimed in claim 1, which is chosen from: (R)-N-[2-(6-Chloro-2- cyclopropylmethyl-3-oxo-2,3-dihydro-1H-isoindol-1yl)-acetyl]-guanidine and (S)-N-[2-(6-Chloro-2-cyclopropylmethyl-3-oxo-2,3-dihydro-1H-isoindol-1-yl)-acetyl]-guanidine:

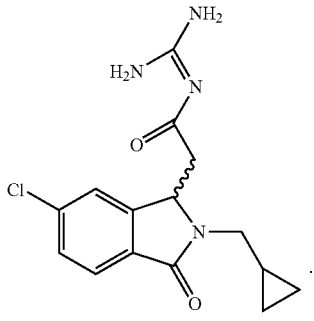

15. A compound as claimed in claim 5, which N-[2-(2-cyclopropylmethyl-6- methanesulfonyl-3-oxo-2,3-dihydro-1H-isoindol-1-yl)-acetyl]-guanidinium.

16. A compound as claimed in claim 6, which is chosen from: (R)-N-[2-(2-cyclopropylmethyl-3-oxo-6-trifluoromethyl-2,3-dihydro-1H-isoindol-1-yl)-acetyl]-guanidine, (S)-N-[2-(2-cyclopropylmethyl-3-oxo-6-trifluoromethyl-2,3-dihydro-1H-isoindol-1-yl)-acetyl]-guanidine, (R)-N-[2-(5,6-dichloro-2-cyclopropylmethyl-3-oxo-2,3-dihydro-1H-isoindol-1-yl)-acetyl]-guanidine, (S)-

N-[2-(5,6-dichloro-2-cyclopropylmethyl-3-oxo-2,3-dihydro-1H-isoindol-1-yl)-acetyl]-guanidine, (R)-N--guanidine, (S)-N--guanidine, (R)-N-[2-(6-chloro-2-cyclopropylmethyl-3-oxo-2,3-dihydro-1H-isoindol-1-yl)-acetyl]-guanidine, (S)-N-[2-(6-chloro-2-cyclopropylmethyl-3-oxo-2,3-dihydro-1H-isoindol-1-yl)-acetyl]-guanidine, (R)-N-[2-(5-chloro-2-cyclopropylmethyl-3-oxo-2,3-dihydro-1H-isoindol-1-yl)-acetyl]-guanidine, and (S)-N-[2-(5-chloro-2-cyclopropylmethyl-3-oxo-2,3-dihydro-1H-isoindol-1-yl)-acetyl]-guanidine.

17. A compound as claimed in claim 16, which is chosen from: (R)-N--guanidine and (S)-N--guanidine:

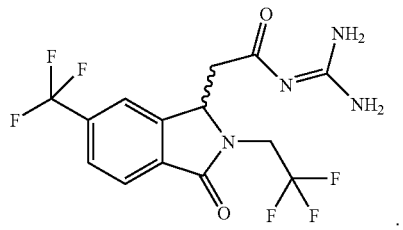

18. A compound as claimed in claim 17, which is (R)-N--guanidine.

* * * * *